(12) United States Patent
Osorio

(10) Patent No.: US 11,957,909 B2
(45) Date of Patent: Apr. 16, 2024

(54) CONTINGENT CARDIO-PROTECTION FOR EPILEPSY PATIENTS

(71) Applicant: Ivan Osorio, Leawood, KS (US)

(72) Inventor: Ivan Osorio, Leawood, KS (US)

(73) Assignee: FLINT HILLS SCIENTIFIC, L.L.C., Lawrence, KS (US)

( * ) Notice: Subject to any disclaimer, the term of this patent is extended or adjusted under 35 U.S.C. 154(b) by 1180 days.

(21) Appl. No.: 16/693,261

(22) Filed: Nov. 23, 2019

(65) Prior Publication Data

US 2020/0114152 A1 Apr. 16, 2020

Related U.S. Application Data

(60) Continuation-in-part of application No. 14/208,466, filed on Mar. 13, 2014, now Pat. No. 10,993,652, which is a continuation-in-part of application No. 14/084,513, filed on Nov. 19, 2013, now Pat. No. 11,083,407, application No. 16/693,261, filed on Nov. 23, 2019 is a continuation-in-part of application No. 15/437,155, filed on Feb. 20, 2017, now Pat. No. 10,682,515, which is a division of application No. 14/050,173, filed on Oct. 9, 2013, now Pat. No. 9,579,506, which is a continuation-in-part of application No. 13/601,099, filed on Aug. 31, 2012, now Pat. No. 9,314,633, which is a continuation-in-part of application No. 12/020,195, filed on Jan. 25, 2008, now Pat. No. 8,260,426, which is a continuation-in-part of application No. 12/020,097, filed on Jan. 25, 2008, now Pat. No. 8,565,867.

(60) Provisional application No. 61/793,292, filed on Mar. 15, 2013, provisional application No. 61/798,274, filed on Mar. 15, 2013, provisional application No. 61/801,950, filed on Mar. 15, 2013, provisional application No. 61/785,429, filed on Mar. 14, 2013.

(51) Int. Cl.
*A61N 1/36* (2006.01)
*A61N 1/05* (2006.01)

(52) U.S. Cl.
CPC ...... *A61N 1/36064* (2013.01); *A61N 1/36053* (2013.01); *A61N 1/36114* (2013.01); *A61N 1/36139* (2013.01); *A61N 1/36185* (2013.01); *A61N 1/0556* (2013.01); *A61N 1/36117* (2013.01)

(58) Field of Classification Search
CPC ............ A61N 1/36064; A61N 1/36053; A61N 1/36114; A61N 1/36139; A61N 1/36185; A61N 1/0556; A61N 1/36117
See application file for complete search history.

(56) References Cited

U.S. PATENT DOCUMENTS

2011/0270095 A1* 11/2011 Bukhman .............. A61B 5/349
607/45

* cited by examiner

Primary Examiner — Amanda K Hulbert
(74) Attorney, Agent, or Firm — CF3; Stephen Eisenmann

(57) ABSTRACT

Disclosed are methods and systems for treating epilepsy by stimulating a main trunk of a vagus nerve, or a left vagus nerve, when the patient has had no seizure or a seizure that is not characterized by cardiac changes such as an increase in heart rate, and stimulating a cardiac branch of a vagus nerve, or a right vagus nerve, when the patient has had a seizure characterized by cardiac changes such as a heart rate increase.

10 Claims, 34 Drawing Sheets

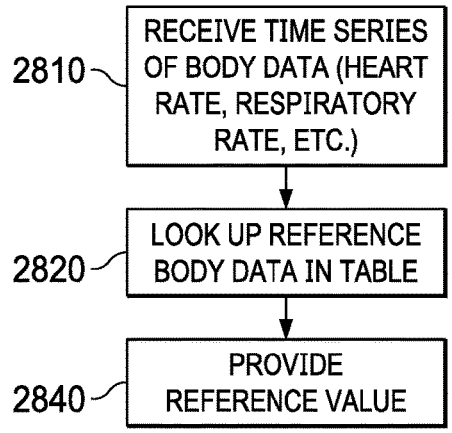

FIG. 28A

| WORK LEVELS | ACTIVITY LEVELS | FIRST BODY DATA VALUES | SECOND BODY DATA VALUES | THIRD BODY DATA VALUES | ○ ○ ○ |
|---|---|---|---|---|---|
| WORK LEVEL - 1 | ACTIVITY TYPE - A REM SLEEP | FIRST BODY DATA VALUE - A | SECOND BODY DATA VALUE - A | THIRD BODY DATA VALUE - A | ○ ○ ○ |
| WORK LEVEL - 2 | ACTIVITY TYPE - B NON-REM SLEEP | FIRST BODY DATA VALUE - B | SECOND BODY DATA VALUE - B | THIRD BODY DATA VALUE - B (e.g., RESPIRATION RATE = 11 BrPM) | ○ ○ ○ |
| WORK LEVEL - 3 | ACTIVITY TYPE - C WALKING | FIRST BODY DATA VALUE - C (e.g., HEART RATE = 82 BPM) | SECOND BODY DATA VALUE - C | THIRD BODY DATA VALUE - C | ○ ○ ○ |
| WORK LEVEL - 4 | ACTIVITY TYPE - D RUNNING | FIRST BODY DATA VALUE - D | SECOND BODY DATA VALUE - D | THIRD BODY DATA VALUE - D | ○ ○ ○ |
| ○ ○ ○ | ○ ○ ○ | ○ ○ ○ | ○ ○ ○ | ○ ○ ○ | |

FIG. 28B

CONTINGENT CARDIO-PROTECTION FOR EPILEPSY PATIENTS

CROSS-REFERENCE TO RELATED APPLICATIONS

This presently being filed application is a continuation-in-part of and claims priority to co-pending U.S. patent application Ser. No. 14/208,466 entitled "Epileptic Event Detection Based on Correlation of Body Signals", filed on Mar. 13, 2014, U.S. patent application Ser. No. 14/208,466 is a continuation-in-part of and claims priority to U.S. patent application Ser. No. 14/084,513 entitled "Pathological State Detection Using Dynamically Determined Body Index Range Values", filed on Nov. 19, 2013 and claims priority to U.S. Provisional Application No. 61/793,292 filed on Mar. 15, 2013, U.S. Provisional Application No. 61/798,274 filed on Mar. 15, 2013, U.S. Provisional Application No. 61/801,950 filed on Mar. 15, 2013, and U.S. Provisional Application No. 61/785,429 filed on Mar. 14, 2013 and this presently being filed application is a continuation-in-part of and claims priority to co-pending U.S. patent application Ser. No. 15/437,155 entitled "Contingent Cardio-Protection For Epilepsy Patients", filed on Feb. 20, 2017, which claims priority to and is a divisional application of U.S. patent application Ser. No. 14/050,173 entitled "Contingent Cardio-Protection For Epilepsy Patients", filed on Oct. 9, 2013 (now U.S. Pat. No. 9,579,506), which claims priority to and is a continuation-in-part of U.S. patent application Ser. No. 13/601,099 entitled "Contingent Cardio-Protection For Epilepsy Patients", filed on Aug. 31, 2012 (now U.S. Pat. No. 9,314,633), which claims priority to and is a continuation-in-part of U.S. patent application Ser. No. 12/020,195 entitled "Method, Apparatus and System for Bipolar Charge Utilization during Stimulation by an Implantable Medical Device", filed on Jan. 25, 2008 (now U.S. Pat. No. 8,260,426) and claims priority to and is a continuation-in-part of U.S. patent application Ser. No. 12/020,097 entitled "Changeable Electrode Polarity Stimulation by an Implantable Medical Device", filed on Jan. 25, 2008 (now U.S. Pat. No. 8,565,867) all of which are incorporated herein by reference in their entireties.

BACKGROUND OF THE DISCLOSURE

This disclosure relates generally to medical devices, and, more particularly, to methods, apparatus, and systems for performing vagus nerve stimulation (VNS) for treating epileptic seizures characterized by cardiac changes, including ictal tachycardia.

DESCRIPTION OF THE RELATED ART

While seizures are the best known and most studied manifestation of epilepsy, cardiac alterations are prevalent and may account for the high rate of sudden unexpected death (SUDEP) in these patients. These alterations may include changes in rate (most commonly tachycardia, rarely bradycardia or asystole), rhythm (PACs, PVCs,), conduction (e.g., bundle branch block) and repolarization abnormalities (e.g., Q-T prolongation, which occurs primarily during (ictal) but also between seizures (inter-ictally). In addition, S-T segment depression (a sign of myocardial ischemia) is observed during epileptic seizures. Significant elevations in heart-type fatty acid binding protein (H-FABP), a cytoplasmic low-molecular weight protein released into the circulation during myocardial injury have been documented in patients with epilepsy and without evidence of coronary artery disease, not only during seizures but also during free-seizure periods. H-FABP is a more sensitive and specific marker of myocardial ischemia than troponin I or CK-MB. Elevations in H-FABP appear to be un-correlated with duration of illness, of the recorded seizures, or with the Chalfont severity score of the patients.

The cardiac alterations in epilepsy patients, both during and between seizures, have a multi-factorial etiology, but a vago-sympathetic imbalance seems to play a prominent role in their generation. The majority of epileptic seizures enhance the sympathetic tone (plasma noradrenaline and adrenaline rise markedly after seizure onset) causing tachycardia, arterial hypertension and increases in the respiratory rate, among others. Recurrent and frequent exposure to the outpouring of catecholamines associated with seizures in patients with pharmaco-resistant epilepsies may, for example, account for abnormalities that increase the risk of sudden death such as prolongation of the Q-T interval which leads to often fatal tachyarrhythmias such as torsade de pointe. Further evidence in support of the role of catecholamines in SUDEP is found in autopsies of SUDEP victims, revealing interstitial myocardial fibrosis (a risk factor for lethal arrhythmias), myocyte vacuolization, atrophy of cardiomyocytes, leukocytic infiltration, and perivascular fibrosis. Restoration of the sympathetic-parasympathetic tone to normal levels, a therapeutic objective that may be accomplished by enhancing parasympathetic activity through among others, electrical stimulation of the vagus nerve, may decrease the rate and severity of cardiac and autonomic co-morbidities in these patients.

While there have been significant advances over the last several decades in treatments for epileptic seizures, the management of co-morbidities—in particular the cardiac alterations associated with seizures—remains largely unaddressed. There is a need for improved epilepsy treatments that address cardiac impairments associated with seizures. Pharmacological therapies for neurological diseases (including epilepsy) have been available for many decades. A more recent treatment for neurological disorders involves electrical stimulation of a target tissue to reduce symptoms or effects of the disorder. Such therapeutic electrical signals have been successfully applied to brain, spinal cord, and cranial nerves tissues improve or ameliorate a variety of conditions. A particular example of such a therapy involves applying an electrical signal to the vagus nerve to reduce or eliminate epileptic seizures, as described in U.S. Pat. Nos. 4,702,254, 4,867,164, and 5,025,807, which are hereby incorporated herein by reference in their entirety.

The endogenous electrical activity (i.e., activity attributable to the natural functioning of the patient's own body) of a neural structure may be modulated in a variety of ways. One such way is by applying exogenous (i.e., from a source other than the patient's own body) electrical, chemical, or mechanical signals to the neural structure. In some embodiments, the exogenous signal ("neurostimulation" or "neuromodulation") may involve the induction of afferent action potentials, efferent action potentials, or both, in the neural structure. In some embodiments, the exogenous (therapeutic) signal may block or interrupt the transmission of endogenous (natural) electrical activity in the target neural structure. Electrical signal therapy may be provided by implanting an electrical device underneath the skin of a patient and delivering an electrical signal to a nerve such as a cranial nerve.

In one embodiment, the electrical signal therapy may involve detecting a symptom or event associated with the patient's medical condition, and the electrical signal may be delivered in response to the detection. This type of stimulation is generally referred to as "closed-loop," "active," "feedback," "contingent" or "triggered" stimulation. Alternatively, the system may operate according to a predetermined program to periodically apply a series of electrical pulses to the nerve intermittently throughout the day, or over another predetermined time interval. This type of stimulation is generally referred to as "open-loop," "passive," "non-feedback," "non-contingent" or "prophylactic," stimulation.

In other embodiments, both open- and closed-loop stimulation modes may be used. For example, an open-loop electrical signal may operate as a "default" program that is repeated according to a programmed on-time and off-time until a condition is detected by one or more body sensors and/or algorithms. The open-loop electrical signal may then be interrupted in response to the detection, and the closed-loop electrical signal may be applied—either for a predetermined time or until the detected condition has been effectively treated. The closed-loop signal may then be interrupted, and the open-loop program may be resumed. Therapeutic electrical stimulation may be applied by an implantable medical device (IMD) within the patient's body or, in some embodiments, externally.

Closed-loop stimulation of the vagus nerve has been proposed to treat epileptic seizures. Many patients with intractable, refractory seizures experience changes in heart rate and/or other autonomic body signals near the clinical onset of seizures. In some instances the changes may occur prior to the clinical onset, and in other cases the changes may occur at or after the clinical onset. Where the changes involves heart rate, most often the rate increases, although in some instances a drop or a biphasic change (up-then-down or down-then-up) may occur. It is possible using a heart rate sensor to detect such changes and to initiate therapeutic electrical stimulation (e.g., VNS) based on the detected change. The closed-loop therapy may be a modified version of an open-loop therapy. See, e.g., U.S. Pat. Nos. 5,928,272, and 6,341,236, each hereby incorporated by reference herein. The detected change may also be used to warn a patient or third party of an impending or occurring seizure.

VNS therapy for epilepsy patients typically involves a train of electrical pulses applied to the nerve with an electrode pair including a cathode and an anode located on a left or right main vagal trunk in the neck (cervical) area. Only the cathode is capable of generating action potentials in nerve fibers within the vagus nerve; the anode may block some or all of the action potentials that reach it (whether endogenous or exogenously generated by the cathode). VNS as an epilepsy therapy involves modulation of one or more brain structures. Therefore, to prevent the anode from blocking action potentials generated by the cathode from reaching the brain, the cathode is usually located proximal to the brain relative to the anode. For vagal stimulation in the neck area, the cathode is thus usually the upper electrode and the anode is the lower electrode. This arrangement is believed to result in partial blockage of action potentials distal to or below the anode (i.e., those that would travel through the vagus nerve branches innervating the lungs, heart and other viscerae). Using an upper-cathode/lower-anode arrangement has also been favored to minimize any effect of the vagus nerve stimulation on the heart.

Stimulation of the left vagus nerve, for treatment of epilepsy has complex effects on heart rate (see Frei & Osorio, Epilepsia 2001), one of which includes slowing of the heart rate, while stimulation of the right vagus nerve has a more prominent bradycardic effect. Electrical stimulation of the right vagus nerve has been proposed for use in the operating room to slow the heart during heart bypass surgery, to provide a surgeon with a longer time period to place sutures between heartbeats (see, e.g., U.S. Pat. No. 5,651,373). Some patents discussing VNS therapy for epilepsy treatment express concern with the risk of inadvertently slowing the heart during stimulation. In U.S. Pat. No. 4,702,254, it is suggested that by locating the VNS stimulation electrodes below the inferior cardiac nerve, "minimal slowing of the heart rate is achieved" (col. 7 lines 3-5), and in U.S. Pat. No. 6,920,357, the use of a pacemaker to avoid inadvertent slowing of the heart is disclosed.

Cranial nerve stimulation has also been suggested for disorders outside the brain such as those affecting the gastrointestinal system, the pancreas (e.g., diabetes, which often features impaired production of insulin by the islets of Langerhans in the pancreas), or the kidneys. Electrical signal stimulation of either the brain alone or the organ alone may have some efficacy in treating such medical conditions, but may lack maximal efficacy.

While electrical stimulation has been used for many years to treat a number of conditions, a need exists for improved VNS methods of treating epilepsy and its cardiac co-morbidities as well as other brain and non-brain disorders.

SUMMARY OF THE DISCLOSURE

In one aspect, the present disclosure relates to a method of treating a patient having epilepsy comprising receiving at least one body data stream, analyzing the at least one body data stream using a seizure or event detection algorithm to detect whether or not the patient is having and/or has had an epileptic seizure, receiving a cardiac signal of the patient, applying a first electrical signal to a vagus nerve of the patient based on a determination that the patient is not having and/or has not had an epileptic seizure characterized by a decrease in the patient's heart rate, wherein the first electrical signal is not a vagus nerve conduction blocking electrical signal, and applying a second electrical signal to a vagus nerve of the patient based on a determination that the patient is having and/or has had an epileptic seizure characterized by a decrease in the patient's heart rate, wherein the second electrical signal is a pulsed electrical signal that blocks action potential conduction in the vagus nerve.

In one aspect, the present disclosure relates to a method of treating a patient having epilepsy comprising sensing a cardiac signal and a kinetic signal of the patient, analyzing at least one of the cardiac signal and the kinetic signal; determining whether or not the patient has had an epileptic seizure based on the analyzing; in response to a determination that the patient has had an epileptic seizure, determining whether or not the seizure is characterized by a decrease in the patient's heart rate, applying a first electrical signal to a vagus nerve of the patient based on a determination that the patient has had an epileptic seizure characterized by a decrease in the patient's heart rate, wherein the first electrical signal is a pulsed electrical signal that blocks action potential conduction in the vagus nerve; and applying a second electrical signal to a vagus nerve of the patient based on one of a) a determination that the patient has not had an epileptic seizure, and b) a determination that the patient has had an epileptic seizure that is not characterized by a decrease in the patient's heart rate, wherein the second electrical signal is not a vagus nerve conduction blocking electrical signal.

In one aspect, the present disclosure relates to a system for treating a medical condition in a patient, comprising at least one electrode coupled to a vagus nerve of the patient, a programmable electrical signal generator, a sensor for sensing at least one body data stream, a seizure detection module capable of analyzing the at least one body data stream and determining, based on the analyzing, whether or not the patient is having and/or has had an epileptic seizure, a heart rate determination unit capable of determining a heart rate of a patient proximate in time to an epileptic seizure detected by the seizure detection module, and a logic unit for applying a first electrical signal to the vagus nerve using the at least one electrode based on a determination by the seizure detection module that the patient is having and/or has had an epileptic seizure characterized by a decrease in the patient's heart rate, wherein the first electrical signal is a pulsed electrical signal that blocks action potential conduction in the vagus nerve, and for applying a second electrical signal to the vagus nerve using the at least one electrode as a cathode based upon one of a) a determination that the patient is not having and/or has not had an epileptic seizure, and b) a determination that the patient is having and/or has had an epileptic seizure that is not characterized by a decrease in the patient's heart rate, wherein the second electrical signal is not a vagus nerve conduction blocking electrical signal. In one embodiment, the seizure detection module may comprise the heart rate determination unit.

In one aspect, the present disclosure relates to a method of treating a patient having epilepsy comprising applying a first electrical signal to a vagus nerve of the patient, wherein the first electrical signal is an open-loop electrical signal having a programmed on-time and a programmed off-time, sensing at least one body signal of the patient, determining the start of an epileptic seizure based on the at least one body signal, determining whether or not the seizure is characterized by a decrease in the patient's heart rate, applying a second, closed-loop electrical signal to a vagus nerve of the patient based on a determination that the epileptic seizure is not characterized by a decrease in the patient's heart rate, and applying a third, closed-loop electrical signal to a vagus nerve of the patient based on a determination that the seizure is characterized by a decrease in the patient's heart rate, wherein the third electrical signal is applied to block action potential conduction on the vagus nerve.

In one aspect, the present disclosure relates to a method of controlling a heart rate of an epilepsy patient comprising sensing a kinetic signal of the patient; analyzing said kinetic signal to determine at least one kinetic index; receiving a cardiac signal of the patient; analyzing the cardiac signal to determine the patient's heart rate; determining if the patient's heart rate is commensurate with the at least one kinetic index; and applying a first electrical signal to a vagus nerve of the patient based on a determination that the patient's heart rate is not commensurate with the kinetic index. In one embodiment, the at least one kinetic index comprises at least one of an activity level or an activity type of the patient, and determining if the heart rate is commensurate with the kinetic index comprises determining if the heart rate is commensurate with the at least one of an activity level or an activity type.

In one aspect, the present disclosure relates to a method of controlling a heart rate of an epilepsy patient comprising sensing at least one of a kinetic signal and a metabolic (e.g., oxygen consumption) signal of the patient; receiving a cardiac signal of the patient; analyzing the cardiac signal to determine the patient's heart rate; determining if the patient's heart rate is commensurate with the at least one of a kinetic and a metabolic signal of the patient; and applying a first electrical signal to a vagus nerve of the patient based on a determination that the patient's heart rate is not commensurate with the at least one of a kinetic signal and a metabolic signal. In one embodiment, the method further comprises determining at least one of an activity level or an activity type of the patient based on the at least one of a kinetic and a metabolic signal, and determining if the heart rate is commensurate with the kinetic signal comprises determining if the heart rate is commensurate with the at least one of an activity level or an activity type.

In one aspect, the present disclosure relates to a method of treating a patient having epilepsy comprising sensing at least one body signal of the patient; determining whether or not the patient is having or has had an epileptic seizure based on the at least one body signal; sensing a cardiac signal of the patient; determining whether or not the seizure is associated with a change in the patient's cardiac signal; applying a first therapy to a vagus nerve of the patient based on a determination that the patient is having or has had an epileptic seizure that is not associated with a change in the patient's cardiac signal, wherein the first therapy is selected from an electrical, chemical, mechanical (e.g., pressure) or thermal signal. The method further comprises applying a second therapy to a vagus nerve of the patient based on a determination that the patient has had an epileptic seizure associated with a change in the patient's cardiac signal, wherein the second therapy is selected from an electrical, chemical, mechanical (e.g., pressure) or thermal signal. In some embodiments, a third therapy may be applied to a vagus nerve based a determination that the patient has not had an epileptic seizure, wherein the third therapy is selected form an electrical, chemical, mechanical or thermal signal.

BRIEF DESCRIPTION OF THE DRAWINGS

The disclosure may be understood by reference to the following description taken in conjunction with the accompanying drawings, in which like reference numerals identify like elements, and in which:

FIG. 28A shows a flowchart depiction of a method, according to some embodiments of the present disclosure; and FIG. 28B depicts an exemplary work level, activity type, and body data value table usable in the method of FIG. 28A, according to some embodiments of the present disclosure.

Figure 1A:
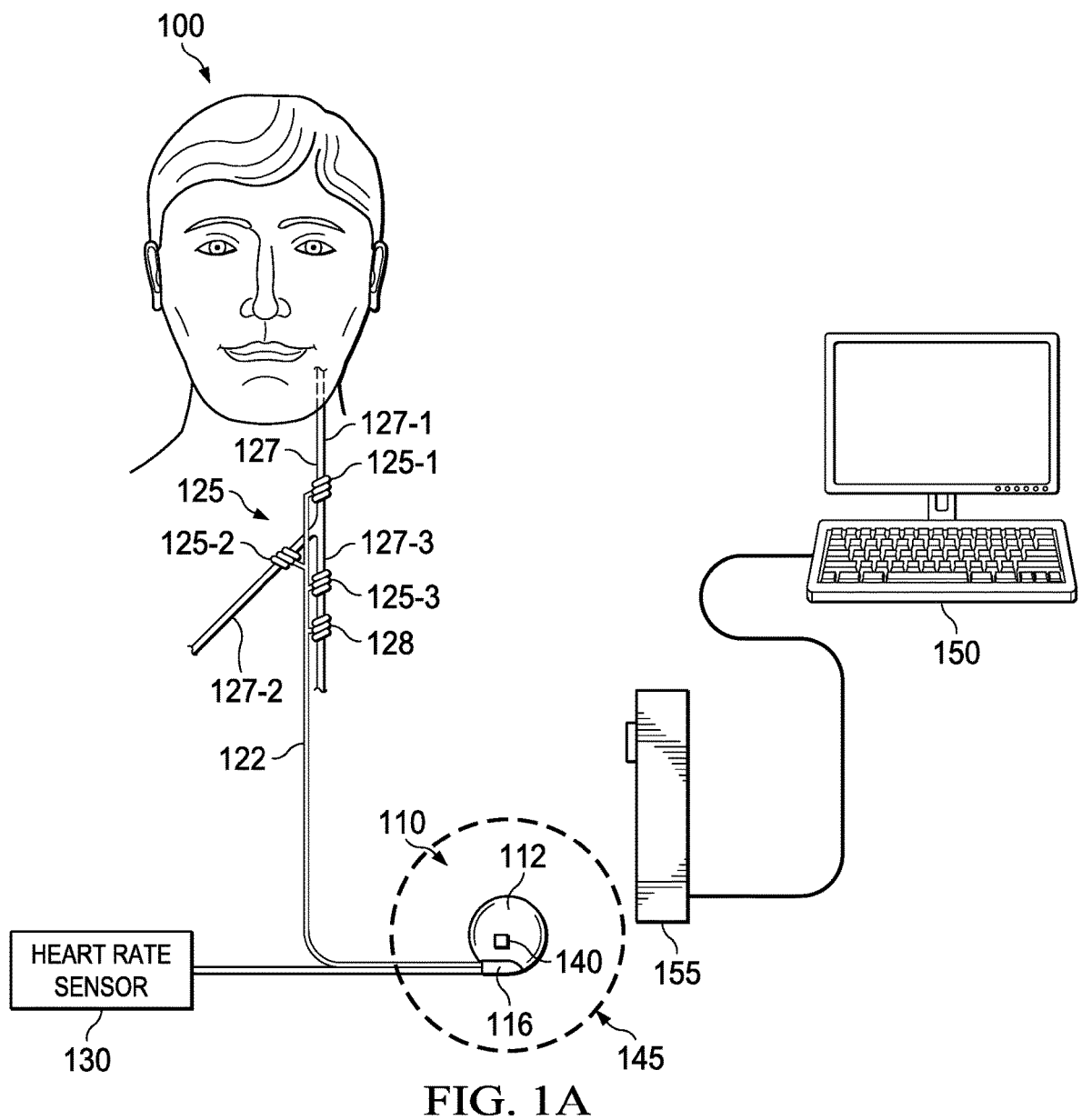
FIGS. 1A-1E provide stylized diagrams of an implantable medical device implanted into a patient's body for providing first and second electrical signals to a vagus nerve of a patient for treating epileptic seizures, in accordance with one illustrative embodiment of the present disclosure.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

DETAILED DESCRIPTION OF SPECIFIC EMBODIMENTS

Illustrative embodiments of the disclosure are described herein. For clarity, not all features of an actual implementation are provided in detail. In any actual embodiment, numerous implementation-specific decisions must be made to achieve the design-specific goals. Such a development effort, while possibly complex and time-consuming, would nevertheless be a routine task for persons of skill in the art given this disclosure.

This application does not intend to distinguish between components that differ in name but not function. "Including" and "includes" are used in an open-ended fashion, and should be interpreted to mean "including, but not limited to." "Couple" or "couples" are intended to mean either a direct or an indirect electrical connection. "Direct contact," "direct attachment," or providing a "direct coupling" indicates that a surface of a first element contacts the surface of a second element with no substantial attenuating medium there between. Small quantities of substances, such as bodily fluids, that do not substantially attenuate electrical connections do not vitiate direct contact. "Or" is used in the inclusive sense (i.e., "and/or") unless a specific use to the contrary is explicitly stated.

"Electrode" or "electrodes" may refer to one or more stimulation electrodes (i.e., electrodes for applying an electrical signal generated by an IMD to a tissue), sensing electrodes (i.e., electrodes for sensing a body signal), and/or electrodes capable of either stimulation or sensing. "Cathode" and "anode" have their standard meanings, as the electrode at which current leaves the IMD system and the electrode at which current enters the IMD system, respectively. Reversing the polarity of the electrodes can be effected by any switching technique known in the art.

A "pulse" is used herein to refer to a single application of electrical charge from the cathode to target neural tissue. A pulse may include both a therapeutic portion (in which most or all of the therapeutic or action-potential-generating effect occurs) and a charge-balancing portion in which the polarity of the electrodes are reversed and the electrical current is allowed to flow in the opposite direction to avoid electrode and/or tissue damage. Individual pulses are separated by a time period in which no charge is delivered to the nerve, which can be called the "interpulse interval." A "burst" is used herein to refer to a plurality of pulses, which may be separated from other bursts by an interburst interval in which no charge is delivered to the nerve. The interburst intervals have a duration exceeding the interpulse interval duration. In one embodiment, the interburst interval is at least twice as long as the interpulse interval. The time period between the end of the last pulse of a first burst and the initiation of the first pulse of the next subsequent burst can be called the "interburst interval." In one embodiment, the interburst interval is at least 100 msec.

A plurality of pulses can refer to any of (a) a number of consecutive pulses within a burst, (b) all the pulses of a burst, or (c) a number of consecutive pulses including the final pulse of a first burst and the first pulse of the next subsequent burst.

"Stimulate," "stimulating" and "stimulator" may generally refer to applying a signal, stimulus, or impulse to neural tissue (e.g., a volume of neural tissue in the brain or a nerve) for affecting it neuronal activity. While the effect of such stimulation on neuronal activity is termed "modulation," for simplicity, the terms "stimulating" and "modulating", and variants thereof, are sometimes used interchangeably herein. The modulation effect of a stimulation signal on neural tissue may be excitatory or inhibitory, and may potentiate acute and/or long-term changes in neuronal activity. For example, the modulation effect of a stimulation signal may comprise: (a) initiating action potentials in the target neural tissue; (b) inhibition of conduction of action potentials (whether endogenous or exogenously generated, or blocking their conduction (e.g., by hyperpolarizing or collision blocking), (c) changes in neurotransmitter/neuromodulator release or uptake, and (d) changes in neuroplasticity or neurogenesis of brain tissue. Applying an electrical signal to an autonomic nerve may comprise generating a response that includes an afferent action potential, an efferent action potential, an afferent hyperpolarization, an efferent hyperpolarization, an afferent sub-threshold depolarization, and/or an efferent sub-threshold depolarization. The terms tachycardia and bradycardia are used here in a relative (i.e., any decrease or decrease in heart rate relative to a reference value) or in an absolute sense (i.e., a pathological change relative to a normative value). In particular, "tachycardia is used interchangeably with an increase heart rate and "bradycardia" may be used interchangeably with a decrease in heart rate.

A variety of stimulation therapies may be provided in embodiments of the present disclosure. Different nerve fiber types (e.g., A, B, and C-fibers that may be targeted) respond differently to stimulation from electrical signals because they have different conduction velocities and stimulation threshold. Certain pulses of an electrical stimulation signal, for example, may be below the stimulation threshold for a particular fiber and, therefore, may generate no action potential. Thus, smaller or narrower pulses may be used to avoid stimulation of certain nerve fibers (such as C-fibers) and target other nerve fibers (such as A and/or B fibers, which generally have lower stimulation thresholds and higher conduction velocities than C-fibers). Additionally, techniques such as a pre-pulse may be employed wherein axons of the target neural structure may be partially depolarized (e.g., with a pre-pulse or initial phase of a pulse) before a greater current is delivered to the target (e.g., with a second pulse or an initial phase such a stair step pre-pulse to deliver a larger quantum of charge). Furthermore, opposing polarity phases separated by a zero current phase may be used to excite particular axons or postpone nerve fatigue during long term stimulation.

Cranial nerve stimulation, such as vagus nerve stimulation (VNS), has been proposed to treat a number of medical conditions, including epilepsy and other movement disorders, depression and other neuropsychiatric disorders, dementia, traumatic brain injury, coma, migraine headache, obesity, eating disorders, sleep disorders, cardiac disorders (such as congestive heart failure and atrial fibrillation), hypertension, endocrine disorders (such as diabetes and hypoglycemia), and pain, among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the variety of disorders for which cranial nerve stimulation has been proposed or suggested, the fact that detailed neural pathways for many (if not all) cranial nerves remain relatively unknown, makes predictions of efficacy for any given disorder difficult or impossible. Even if such pathways were known, the precise stimulation parameters that would modulate particular pathways relevant to a particular disorder generally cannot be predicted.

Cardiac signals suitable for use in embodiments of the present disclosure may comprise one or more of an electrical (e.g., EKG), acoustic (e.g., phonocardiogram or ultrasound/ECHO), force or pressure (e.g., apexcardiogram), arterial pulse pressure and waveform or thermal signals that may be recorded and analyzed to extract features such as heart rate, heart rate variability, rhythm (regular, irregular, sinus, ventricular, ectopic, etc.), morphology, etc.

It appears that sympatho-vagal imbalance (lower vagal and higher sympathetic tone) plays an important role in generation of a wide spectrum of ictal and interictal alterations in cardiac dynamics, ranging from rare unifocal PVCs to cardiac death. Without being bound by theory, restoration of the vagal tone to a level sufficient to counteract the pathological effects of elevated catecholamines may serve a cardio-protective purpose that would be particularly beneficial in patients with pharmaco-resistant epilepsies, who are at highest risk for SUDEP.

In one embodiment, the present disclosure provides methods and apparatus to increase cardiac vagal tone in epilepsy patients by timely delivering therapeutic electrical currents to the trunks of the right or left vagus nerves or to their cardiac rami (branches), in response to increases in sympathetic tone, by monitoring among others, heart rate, heart rhythm, EKG morphology, blood pressure, skin resistance, catecholamine or their metabolites and neurological signals such as EEG/ECoG, kinetic (e.g., amplitude velocity, direction of movements) and cognitive (e.g., complex reaction time).

In one embodiment, the present disclosure provides a method of treating a medical condition selected from the group consisting of epilepsy, neuropsychiatric disorders (including but not limited to depression), eating disorders/obesity, traumatic brain injury, addiction disorders, dementia, sleep disorders, pain, migraine, endocrine/pancreatic disorders (including but not limited to diabetes), motility disorders, hypertension, congestive heart failure/cardiac capillary growth, hearing disorders, angina, syncope, vocal cord disorders, thyroid disorders, pulmonary disorders, gastrointestinal disorders, kidney disorders, and reproductive endocrine disorders (including infertility).

Figure 1B:
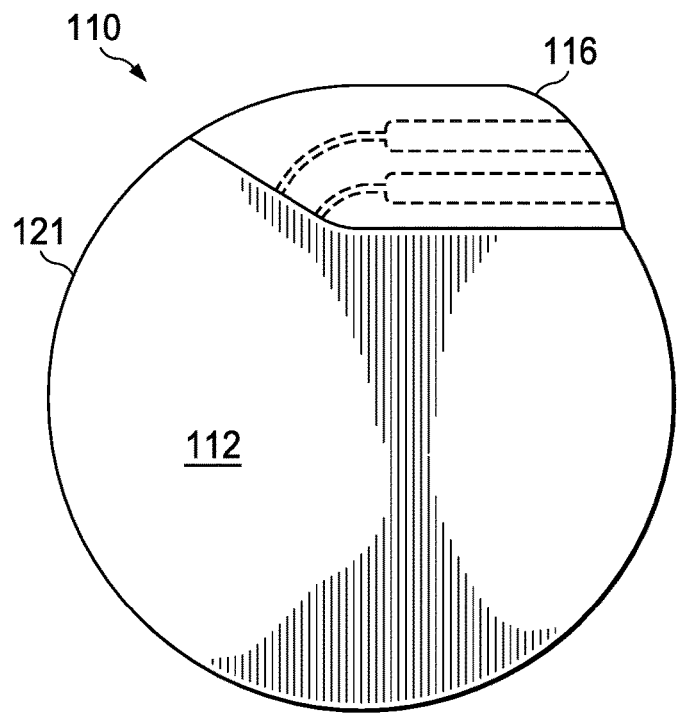

FIGS. 1A-1E depict a stylized implantable medical system 100 for implementing one or more embodiments of the present disclosure. FIGS. 1A and 1B illustrate an electrical signal generator 110 having main body 112 comprising a case or shell (commonly referred to as a "can") 121 (FIG. 1B) with a header 116 for connecting to a lead assembly 122. An electrode assembly 125, preferably comprising at least an electrode pair, is conductively connected to the distal end of an insulated, electrically conductive lead assembly 122, which preferably comprises a plurality of lead wires (at least one wire for each electrode of the electrode assembly 125). Lead assembly 122 is attached at its proximal end to one or more connectors on header 116 (FIG. 1B).

Electrode assembly 125 may be surgically coupled to a target tissue for delivery of a therapeutic electrical signal, which may be a pulsed electrical signal. The target tissue may be a cranial nerve, such as a vagus nerve 127 (FIGS. 1A, 1C-E) or another cranial nerve such as a trigeminal nerve. Electrode assembly 125 includes one or more electrodes 125-1, 125-2, 125-3, which may be coupled to the target tissue. The electrodes may be made from any of a variety of conductive metals known in the art, e.g., platinum, iridium, oxides of platinum or iridium, or combinations of the foregoing. In one embodiment, the target tissue is a vagus nerve 127, which may include an upper main trunk portion 127-1 above a cardiac branch 127-2, and a lower main trunk portion 127-3 below the cardiac branch.

Figure 1C:
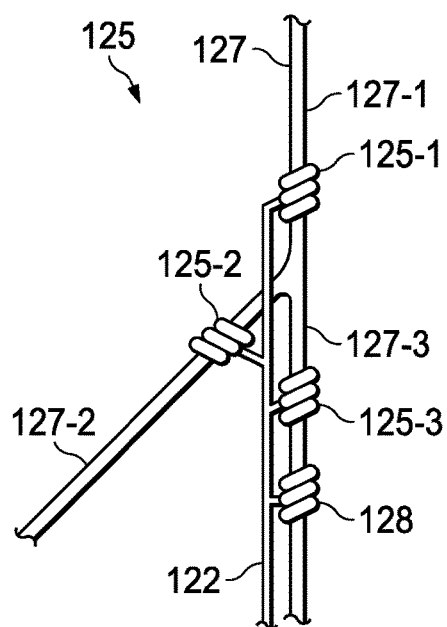

In one embodiment, at least one electrode may be coupled to the main trunk of the vagus nerve, and at least one electrode 125-2 may be coupled to a cardiac branch 127-2 of the vagus nerve (FIG. 1C). The at least one main trunk electrode may be coupled to an upper main trunk 127-1 (e.g., electrode 125-1, FIG. 1C) or a lower main trunk 127-3 (e.g., electrode 125-3). The at least one main trunk electrode (125-1, 125-3) may be used as a cathode to provide a first electrical signal to the upper (127-1) or lower (127-3) main trunk. Cardiac branch electrode 125-2 may be used as a cathode to provide a second electrical signal to cardiac branch 127-2. An additional electrode to function as the anode may be selected from one or more of the other electrodes in electrode assembly 125, can 121, or a dedicated anode.

In some embodiments (FIGS. 1D, 1E), electrode assembly 125 may include a main trunk electrode pair comprising a cathode 125-1a and an anode 125-1b for coupling to a main trunk of a vagus nerve 127. The main trunk electrode pair 125-1a, 125-1b may be coupled to an upper main trunk 127-1 of a vagus nerve (FIG. 1D), or to a lower main trunk 127-3 (FIG. 1E) for delivering a first electrical signal. Without being bound by theory, it is believed that few or no vagal afferent fibers in the lower main trunk 127-3 pass into cardiac branch 127-2 and, accordingly, that effects of the first electrical signal on cardiac function may be minimized by coupling electrode pair 125-1a and 125-1b to the lower main trunk 127-3 instead of upper main trunk 127-1. Cardiac effects may also be minimized by alternative embodiments in which the first electrical signal is applied to a lower main trunk 127-3 using a single electrode (e.g., 125-3, FIG. 1C) as a cathode and an anode that is not coupled to the vagus nerve 127 (e.g., by using can 121 as an anode).

In some embodiments (FIGS. 1D, 1E), electrode assembly 125 may include a cardiac branch electrode pair comprising a cathode 125-2a and an anode 125-2b for coupling to a cardiac branch of a vagus nerve. The second cardiac branch electrode pair may be used to provide a second electrical signal to a cardiac branch of the nerve to affect the cardiac function of the patient.

Referring again to FIGS. 1C-1E, a first electrical signal may be provided to generate afferent action potentials in a main trunk of a vagus nerve to modulate electrical activity of the patient's brain without significantly affecting the patient's heart rate. The second electrical signal may generate efferent action potentials to module the cardiac activity of the patient, and in particular to slow the patient's heart rate (e.g., to treat an epilepsy patient having seizures characterized by ictal tachycardia) and maintain or restore a sympathetic/parasympathetic balance to a non-pathological state. The first electrical signal may be applied to the main trunk of the vagus nerve in a variety of ways, so long as at least one electrode is coupled to the main trunk as a cathode. As noted, the cathode may be coupled to either an upper (127-1) or lower (127-3) main trunk, and an anode may be provided by any of the other electrodes on the vagus nerve (e.g., 125-1b, 125-2b, 125-3, FIGS. 1C-1E) or by a separate anode not coupled to the vagus nerve (e.g., can 121). In one alternative embodiment, an electrode 125-3 may be coupled to a lower main trunk 127-3 of the vagus nerve to function as an anode. In yet another embodiment, each individual electrode element in FIGS. 1A-E (e.g., 125-1, 125-2, 125-3, 125-1a, 125-1g, 125-2a, 125-2b) may comprise an electrode pair comprising both an anode and a cathode. In an additional embodiment, each individual electrode element may comprise three electrodes (e.g., one serving as cathode and the other two as anodes). Suitable electrode assemblies are available from Cyberonics, Inc., Houston, Texas, USA as the Model 302, PerenniaFlex and PerenniaDura electrode assemblies. In view of the present disclosure, persons of skill in the art will appreciate that many electrode designs could be used in embodiments of the present disclosure including unipolar electrodes.

Embodiments of the present disclosure may comprise electrical signals with either charge-balanced or non-charge-balanced pulses (e.g., monopolar/monophasic, direct current (DC)). Charge-balanced pulses involve a first phase in which the stimulation occurs (i.e., action potentials are induced in target nerve fibers), and a second phase in which the polarity of the electrodes are reversed (i.e., the stimulation phase cathode becomes the charge-balancing phase anode, and vice versa). The result is a pulse having two opposite-polarity phases of equal charge, such that no net charge flows across the electrode during a pulse. Charge-balancing is often used to avoid damage to the electrodes that may result if a pulse results in a net charge flowing across the electrodes.

In some instances, charge-balancing may involve a passive discharge phase as illustrated in, e.g., FIG. 1A of US Publication 2006/0173493, which is hereby incorporated by reference in its entirety. In passive charge-balancing, the charge-balancing phase typically involves allowing a capacitor having a charge equal to the charge applied to the nerve during the stimulation phase to discharge through the polarity-reversed electrodes. Passive charge-balancing typically uses much lower initial current than the stimulation phase, with the current declining to zero over a much longer time period than the pulse width of the stimulation phase. A lower current is typically selected in the charge-balancing phase so as to avoid or minimize nerve recruitment during the charge-balancing phase. In active charge-balancing, the charge-balancing phase is not accomplished by the passive discharge of a capacitor, but by providing a second phase having an opposite polarity but the same charge magnitude (pulse width multiplied by current) as the first phase. As is usually the case with passive charge-balancing, active charge-balancing typically involves a much lower current that is applied over a longer time period than the stimulation phase, so as to avoid nerve recruitment. In some instances, however, the active charge-balancing phase may be used as a second stimulation phase by selecting a current magnitude of the cathode in the charge-balancing phase (typically a second electrode, which may be the anode of the initial stimulation phase) that is sufficient to generate action potentials in nerve fibers of the target tissue.

Embodiments of the present disclosure may be implemented using passive charge balancing or active charge-balancing, and the latter may be provided as a stimulation phase or a non-stimulation phase. Some embodiments may be implemented with non-charge-balanced pulses. Persons of skill in the art, having the benefit of the present disclosure, may select the type of charge balancing (if desired) based upon a number of factors including but not limited to whether or not the charge-balancing is intended to affect the cardiac cycle or not, whether afferent or efferent stimulation is desired, the number and location of available electrodes for applying the electrical signal, the fibers intended to be recruited during a particular phase and their physiological effects, among many other factors.

In the discussion of electrical signals in the present disclosure, unless otherwise stated, references to electrodes as cathodes or anodes refers to the polarities of the electrodes during a stimulation phase of a pulse, whether the pulse is a charge-balanced pulse or a non-charge-balanced pulse (e.g., monopolar/monophasic or DC). It will be appreciated that where charge-balanced pulses are employed, the polarities will be reversed during a charge-balancing phase. Where active charge-balancing is used, cardiac effects may be further amplified or ameliorated, depending upon the location of the electrodes being used.

Returning to FIG. 1A, in some embodiments, a heart rate sensor 130, and/or a kinetic sensor 140 (e.g., a triaxial accelerometer) may be included in the system 100 to sense one or more of a cardiac signal or data stream and a kinetic data stream of the patient. In one embodiment, the heart rate sensor may comprise a separate element 130 that may be coupled to generator 110 through header 116 as illustrated in FIG. 1A. In another embodiment, the electrodes 125-1, 125-2, 125-3 and/or the can 121 may be used as sensing electrodes to sense heart rate. An accelerometer may be provided inside generator 110 in one embodiment to sense a kinetic signal (e.g., body movement) of the patient. One or more of the heart rate sensor 130 and the kinetic sensor 140 may be used by a seizure detection algorithm in the system 100 to detect epileptic seizures. In alternative embodiments, other body signals (e.g., blood pressure, brain activity, blood oxygen/$CO_2$ concentrations, temperature, skin resistivity, etc.) of the patient may be sensed and used by the seizure detection algorithm to detect epileptic seizures. Signal generator 110 may be implanted in the patient's chest in a pocket or cavity formed by the implanting surgeon below the skin (indicated by line 145, FIG. 1A).

Returning to FIGS. 1A and 1C, a first electrode 125-1 may be wrapped or otherwise electrically coupled to an upper main trunk 127-1 of a vagus nerve 127 of the patient, and a second electrode 125-2 may be wrapped or coupled to a cardiac branch 127-2 of the vagus nerve. In one embodiment, a third electrode 125-3 may be coupled to a lower main trunk 127-3 of the vagus nerve below the cardiac branch 127-2 of the vagus nerve, instead of or in addition to first electrode 125-1 coupled to the upper main trunk above the cardiac branch. In some embodiments, third electrode 125-3 may be omitted. Electrode assembly 125 may be secured to the nerve by a spiral anchoring tether 128 (FIG. 1C), which in one embodiment does not include an electrode but in alternative embodiments may contain up to three electrodes that serve as cathode(s) and anode(s) in any possible combination. Lead assembly 122 may further be secured, while retaining the ability to flex, by a suture connection 130 to nearby tissue (FIG. 1C). In particular embodiments, any of first, second and third electrodes 125-1, 125-2, and 125-3 may be used as either a cathode or as an anode. In general, the foregoing electrodes may be used as a cathode when the particular electrode is the closest electrode (among a plurality of electrodes) to the target organ (e.g., heart, brain, stomach, liver, etc.) to be stimulated. While a single electrode (e.g., 125-1, 125-2, or 125-3) is illustrated in connection with upper main trunk 127-1, cardiac branch 127-2, and lower main trunk 127-3 in FIGS. 1A and 1C for simplicity, it will be appreciated that one or more additional electrodes can be provided on each of the foregoing neural structures to provide greater flexibility in stimulation.

In one embodiment, the open helical design of the electrodes 125-1, 125-2, 125-3, is self-sizing, flexible, minimize mechanical trauma to the nerve and allow body fluid interchange with the nerve. The electrode assembly 125 preferably conforms to the shape of the nerve, providing a low stimulation threshold by allowing a large stimulation contact area with the nerve. Structurally, the electrode assembly 125 comprises an electrode ribbon (not shown) for each of electrodes 125-1, 125-2, 125-3, made of a conductive material such as platinum, iridium, platinum-iridium alloys, and/or oxides thereof. The electrode ribbons are individually bonded to an inside surface of an elastomeric body portion of the spiral electrodes 125-1, 125-2, 125-3 (FIG. 1C), which may comprise spiral loops of a multi-loop helical assembly. Lead assembly 122 may comprise three distinct lead wires or a triaxial cable that are respectively coupled to one of the conductive electrode ribbons. One suitable method of coupling the lead wires to the electrodes 125-1, 125-2, 125-3 comprises a spacer assembly such as that disclosed in U.S. Pat. No. 5,531,778, although other known coupling methods may be used.

The elastomeric body portion of each loop may be composed of silicone rubber or other biocompatible elastomeric compounds, and the fourth loop 128 (which may have no electrode in some embodiments) acts as the anchoring tether for the electrode assembly 125.

In one embodiment, electrical pulse generator 110 may be programmed with an external computer 150 using programming software known in the art for stimulating neural structures, and a programming wand 155 to facilitate radio frequency (RF) communication between the external computer 150 (FIG. 1A) and the implanted pulse generator 110. In one embodiment, wand 155 and software permit wireless, non-invasive communication with the generator 110 after surgical implantation. Wand 155 may be powered by internal batteries, and provided with a "power on" light to indicate sufficient power for communications. Another indicator light may be provided to show that data transmission is occurring between the wand and the generator. In other embodiments, wand 155 may be omitted, e.g., where communications occur in the 401-406 MHz bandwidth for Medical Implant Communication Service (MICS band).

In some embodiments of the disclosure, a body data stream may be analyzed to determine whether or not a seizure has occurred. Many different body data streams and seizure detection indices have been proposed for detecting epileptic seizures. Additional details on method of detecting seizure from body data are provided in U.S. Pat. Nos. 8,337,404 and 8,382,667, both issued in the name of the present applicant and both entitled, "Detecting, Quantifying, and/or Classifying Seizures Using Multimodal Data," as well as in co-pending U.S. patent application Ser. No. 13/288,886, filed Nov. 3, 2011, each hereby incorporated by reference in its entirety herein. Seizure detection based on the patient's heart rate (as sensed by implanted or external electrodes), movement (as sensed by, e.g., a triaxial accelerometer), responsiveness, breathing, blood oxygen saturation, skin resistivity/conductivity, temperature, brain activity, and a number of other body data streams are provided in the foregoing patents and co-pending applications.

In one embodiment, the present disclosure provides a method for treating a patient with epilepsy in which a body data stream is analyzed using a seizure detection algorithm to determine whether or not the patient has had an epileptic seizure. As used herein, the term "has had an epileptic seizure" includes instances in which a seizure onset has been detected, as well as instances in which the seizure onset has been detected and the seizure is still ongoing (i.e., the seizure has not ended). If the analysis results in a determination that the patient has not had an epileptic seizure, a signal generator may apply a first electrical signal to a main trunk of a vagus nerve of the patient. If the analysis results in a determination that the patient has had an epileptic seizure, the signal generator may apply a second electrical signal to a cardiac branch of a vagus nerve of the patient. In some embodiments, the application of the first electrical signal to the main trunk is terminated, and only the second electrical signal to the cardiac branch is provided once a seizure is detected.

In alternative embodiments, both the first and second electrical signals may be applied to the main trunk and cardiac branch, respectively, of the vagus nerve in response to a determination that the patient has had a seizure (i.e., the first electrical signal continues to be applied to the main trunk of the vagus nerve and the second signal is initiated). Where both the first and second electrical signals are provided, the two signals may be provided sequentially, or in alternating fashion to the main trunk and the cardiac branch. In one embodiment, the first signal may be provided to the main trunk by using one of the upper main trunk electrode 125-1 or the lower main trunk electrode 125-3 as the cathode and the cardiac branch electrode 125-2 as the anode, or by using both of the upper main trunk electrode and the lower main trunk electrode as the cathode and the anode. The second signal may be provided (e.g., by rapidly changing the polarity of the electrodes) by using the cardiac branch electrode 125-2 as the cathode and a main trunk electrode 125-1 or 125-3 as the anode.

In still other embodiments, the second electrical signal is applied to the cardiac branch of the vagus nerve only if the analysis results in a determination that the patient is having and/or has had an epileptic event that is accompanied by an increase in heart rate, and the second electrical signal is used to lower the heart rate back towards a rate that existed prior to the seizure onset. Without being bound by theory, the present inventors believe that slowing the heart rate at the onset of seizures—particularly where the seizure is accompanied by an increase in heart rate—may improve the ability of VNS therapy to provide cardio-protective benefits.

Prior patents describing vagus nerve stimulation as a medical therapy have cautioned that undesired slowing of the heart rate may occur, and have proposed various methods of avoiding such a slowing of the heart rate. In U.S. Pat. No. 6,341,236, it is suggested to sense heart rate during delivery of VNS and if a slowing of the heart rate is detected, either suspending delivery of the VNS signal or pacing the heart using a pacemaker. The present application discloses a VNS system that detects epileptic seizures, particularly epileptic seizures accompanied by an increase in heart rate, and intentionally applies an electrical signal to slow the heart rate in response to such a detection. In another aspect, the present application discloses VNS systems that provide a first electrical signal to modulate only the brain during periods in which no seizure has been detected, and either 1) a second electrical signal to modulate only the heart (to slow its rate) or 2) both a first electrical signal to the brain and a second electrical signal to the heart, in response to a detection of the onset of an epileptic seizure. These electrical signals may be delivered simultaneously, sequentially (e.g., delivery of stimulation to the brain precedes delivery of stimulation to the heart or vice versa), or delivery of the first and second signals may be interspersed or interleaved.

The first electrode may be used as a cathode to provide an afferent first electrical signal to modulate the brain of the patient via main trunk electrode 125-1. Electrode 125-1 may generate both afferent and efferent action potentials in vagus nerve 127. One or more of electrodes 125-2 and 125-3 are used as anodes to complete the circuit. Where this is the case, some of the action potentials may be blocked at the anode(s), with the result that the first electrical signal may predominantly modulate the brain by afferent actions traveling toward the brain, but may also modulate one or more other organs by efferent action potentials traveling toward the heart and/or lower organs, to the extent that the efferent action potentials are not blocked by the anode(s).

The second electrode may be used as a cathode to provide an efferent second electrical signal to slow the heart rate of the patient via cardiac branch electrode 125-2. Either first electrode 125-1 or a third electrode 125-3 (or can 121) may be used as an anode to complete the circuit. In one embodiment, the first electrical signal may be applied to the upper (127-1) or lower (127-3) main trunk of the vagus nerve in an open-loop manner according to programmed parameters including an off-time and an on-time. The on-time and off-time together establish the duty cycle determining the fraction of time that the signal generator applies the first electrical. In one embodiment, the off-time may range from 7 seconds to several hours or even longer, and the on-time may range from 5 seconds to 300 seconds. It should be noted that the duty cycle does not indicate when current is flowing through the circuit, which is determined from the on-time together with the pulse frequency (usually 10-200, Hz, and more commonly 20-30 Hz) and pulse width (typically 0.1-0.5 milliseconds). The first electrical signal may also be defined by a current magnitude (e.g., 0.25-3.5 milliamps), and possibly other parameters (e.g., pulse width, and whether or not a current ramp-up and/or ramp-down is provided, a frequency, and a pulse width.

In one embodiment, a seizure detection may result in both applying the first electrical signal to provide stimulation to the brain in close proximity to a seizure detection (which may interrupt or terminate the seizure), as well as application of the second electrical signal which may slow the heart, thus exerting a cardio-protective effect. In a particular embodiment, the second electrical signal is applied only in response to a seizure detection that is characterized by (or accompanied or associated with) an increase in heart rate, and is not applied in response to seizure detections that are not characterized by an increase in heart rate. In this manner, the second electrical signal may help interrupt the seizure by restoring the heart to a pre-seizure baseline heart rate when the patient experiences ictal tachycardia (elevated heart rate during the seizure), while leaving the heart rate unchanged if the seizure has no significant effect on heart rate.

In still further embodiments, additional logical conditions may be established to control when the second electrical signal is applied to lower the patient's heart rate following a seizure detection. In one embodiment, the second electrical signal is applied only if the magnitude of the ictal tachycardia rises above a defined level. In one embodiment, the second electrical signal is applied to the cardiac branch only if the heart rate increases by a threshold amount above the pre-ictal baseline heart rate (e.g., more than 20 beats per minute above the baseline rate). In another embodiment, the second electrical signal is applied to the cardiac branch only if the heart rate exceeds an absolute heart rate threshold (e.g., 100 beats per minute, 120 beats per minute, or other programmable threshold). In a further embodiment, a duration constraint may be added to one or both of the heart rate increase or absolute heart rate thresholds, such as a requirement that the heart rate exceed the baseline rate by 20 beats per minute for more than 10 seconds, or exceed 110 beats per minute for more than 10 seconds, before the second electrical signal is applied to the cardiac branch in response to a seizure detection.

In another embodiment, the heart rate sensor continues to monitor the patient's heart rate during and/or after application of the second electrical signal, and the second electrical signal is interrupted or terminated if the patient's heart rate is reduced below a low heart rate threshold, which may be the baseline heart rate that the patient experienced prior to the seizure, or a rate lower or higher than the baseline pre-ictal heart rate. The low rate threshold may provide a measure of safety to avoid undesired events such as bradycardia and/or syncope.

In yet another embodiment, heart rate sensor 130 may continue to monitor heart rate and/or kinetic sensor 140 may continue to monitor body movement in response to applying the second electrical signal, and the second electrical signal may be modified (e.g., by changing one or more parameters such as pulse frequency, or by interrupting and re-initiating the application of the second electrical signal to the cardiac branch of the vagus nerve) to control the heart rate below an upper heart rate threshold and/or body movement exceeds one or more movement thresholds. For example, the frequency or duration of the second electrical signal applied to the cardiac branch of the vagus nerve may be continuously modified based the instantaneous heart rate as monitored during the course of a seizure to control what would otherwise be an episode of ictal tachycardia below an upper heart rate threshold. In one exemplary embodiment, the second electrical signal may be programmed to provide a 30-second pulse burst at 30 Hz, with the pulses having a pulse width of 0.25 milliseconds and a current of 1.5 milliamps. If, at the end of the 30 second burst, the heart rate remains above 120 beats per minute, and is continuing to rise, the burst may be extended to 1 minute instead of 30 seconds, the frequency may be increased to 50 Hz, the pulse width may be increased to 350 milliseconds, or combinations of the foregoing. In still further embodiments, additional therapies (e.g., oxygen delivery, drug delivery, cooling therapies, etc.) may be provided to the patient if the body data (heart rate, kinetic activity, etc.) indicates that the patient's seizure is not under control or terminated.

Abnormalities or changes in EKG morphology or rhythm relative to an interictal morphology or rhythm may also trigger delivery of current to the heart via the trunks of vagi or its cardiac rami. In other embodiments, pharmacological agents such as beta-blockers may be automatically released into a patient's blood stream in response to the detection of abnormal heart activity during or between seizures.

In one embodiment, the first electrical signal and the second electrical signal are substantially identical. In another embodiment, the first electrical signal may vary from the second electrical signal in terms of one or more of pulse width, number of pulses, amplitude, frequency, inter-pulse-interval, stimulation on-time, and stimulation off-time, among other parameters and degree, rate or type of charge balancing.

The number of pulses applied to the main trunk or cardiac branch, respectively, before changing the polarity of the first and second electrodes need not be one. Thus, two or more pulses may be applied to the main trunk before applying pulses to the cardiac branch of the vagus nerve. More generally, the first and second signals can be independent of one another and applied according to timing and programming parameters controlled by the controller 210 and stimulation unit 220.

In one embodiment, one or more pulse bursts of the first electrical signal are applied to the main trunk of the vagus nerve in response to a detected seizure before applying one or more bursts of the second electrical signal to the cardiac branch. In another embodiment, the first and second signals are interleaved on a pulse-by-pulse basis under the control of the controller 210 and stimulation unit 220.

Typically, VNS can be performed with pulse frequency of 20-30 Hz (resulting in a number of pulses per burst of 140-1800, at a burst duration from 7-60 sec). In one embodiment, at least one of the first electrical signal and the second electrical signal comprises a microburst signal. Microburst neurostimulation is discussed by U.S. Ser. No. 11/693,451, filed Mar. 2, 2007 and published as United States patent Publication No. 20070233193, and incorporated herein by reference in its entirety. In one embodiment, at least one of the first electrical signal, the second electrical signal, and the third electrical signal is characterized by having a number of pulses per microburst from 2 pulses to about 25 pulses, an interpulse interval of about 2 msec to about 50 msec, an interburst period of at least 100 msec, and a microburst duration of less than about 1 sec.

Cranial nerves such as the vagus nerve include different types of nerve fibers, such as A-fibers, B-fibers and C-fibers. The different fiber types propagate action potentials at different velocities. Each nerve fiber is directional—that is, endogenous or natural action potentials can generally propagate action potentials in only one direction (e.g., afferently to the brain or efferently to the heart and/or viscera). That direction is referred to as the orthodromic direction. Exogenous stimulation (e.g., by electrical pulses) may induce action potentials in both the orthodromic direction as well as the antidromic direction. Depending upon the desired effects of stimulation (e.g., afferent modulation of the brain, efferent modulation of the heart, etc.) certain measures (e.g., cooling, pressure, etc.) may be taken to block propagation in either the efferent or the afferent direction. It is believed that the anode may block at least some action potentials traveling to it from the cathode. For example, referring to FIG. 1, both afferent and efferent action potentials may be generated in an upper main trunk of vagus nerve 127-1 by applying a pulse to the nerve using upper main trunk electrode 125-1 as a cathode. Action potentials generated at upper main trunk electrode 125-1 and traveling toward the heart on cardiac branch 127-2 may be blocked by cardiac branch anode 125-2. Action potentials traveling from the upper main trunk 127-1 to the lower organs in lower main trunk 127-3 may be either blocked (by using lower main trunk electrode 125-3 as an anode either with or instead of cardiac branch electrode 125-2) or allowed to travel to the lower organs (by not using electrode structure 125-3 as an electrode).

Action potentials may be generated and allowed to travel to the heart by making the electrode 125-2 the cathode. If cardiac branch electrode 125-2 is used as a cathode, action potentials will reach the heart in large numbers, while action potentials traveling afferently toward the brain may be blocked in the upper trunk if upper electrode 125-1 is made the anode.

In a further embodiment of the disclosure, rapid changes in electrode polarity may be used to generate action potentials to collision block action potentials propagating in the opposite direction. To generalize, in some embodiments, the vagus nerve can be selectively stimulated to propagate action potentials either afferently (i.e., to the brain) or efferently (i.e., to the heart and/or lower organs/viscerae).

Figure 2:
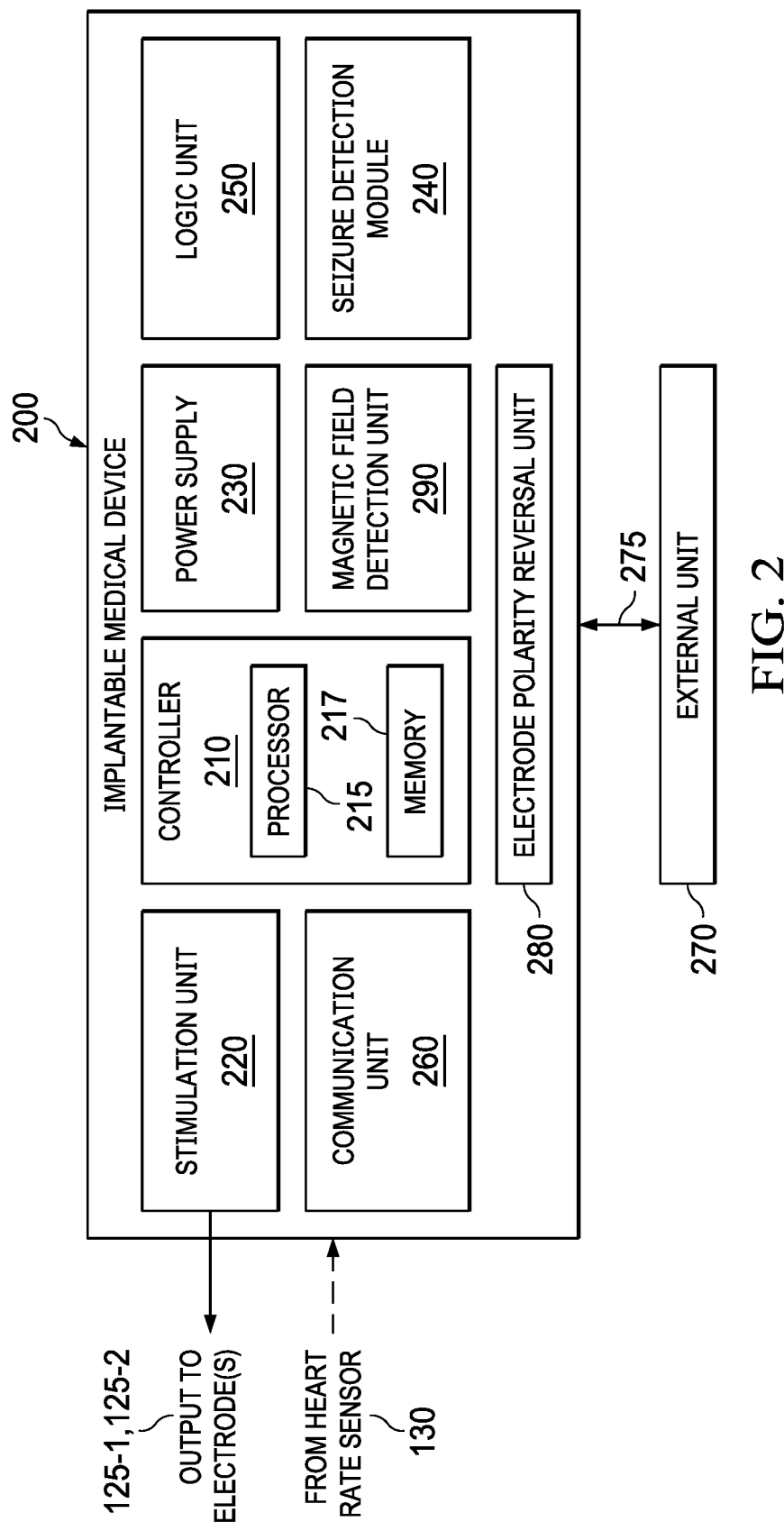
FIG. 2 illustrates a block diagram depiction of an implantable medical device of FIG. 1, in accordance with one illustrative embodiment of the present disclosure.

Turning now to FIG. 2, a block diagram depiction of an implantable medical device, in accordance with one illustrative embodiment of the present disclosure is illustrated. The IMD 200 may be coupled to various electrodes 125 and/or 127 via lead(s) 122 (FIGS. 1A, 1C). First and second electrical signals used for therapy may be transmitted from the IMD 200 to target areas of the patient's body, specifically to various electrodes associated with the leads 122. Stimulation signals from the IMD 200 may be transmitted via the leads 122 to stimulation electrodes (electrodes that apply the therapeutic electrical signal to the target tissue) associated with the electrode assembly 125, e.g., 125-1, 125-2, 125-3 (FIG. 1A).

The IMD 200 may comprise a controller 210 capable of controlling various aspects of the operation of the IMD 200. The controller 210 is capable of receiving internal data and/or external data and controlling the generation and delivery of a stimulation signal to target tissues of the patient's body. For example, the controller 210 may receive manual instructions from an operator externally, may perform stimulation based on internal calculations and programming, and may receive and/or process sensor data received from one or more body data sensors such as electrodes 125-1, 125-2, 125-3, or heart rate sensor 130. The controller 210 is capable of affecting substantially all functions of the IMD 200.

The controller 210 may comprise various components, such as a processor 215, a memory 217, etc. The processor 215 may comprise one or more micro controllers, microprocessors, etc., that are capable of executing a variety of software components. The processor may receive, pre-condition and/or condition sensor signals, and may control operations of other components of the IMD 200, such as stimulation unit 220, seizure detection module 240, logic unit 250, communication unit, 260, and electrode polarity reversal unit 280. The memory 217 may comprise various memory portions, where a number of types of data (e.g., internal data, external data instructions, software codes, status data, diagnostic data, etc.) may be stored. The memory 217 may store various tables or other database content that could be used by the IMD 200 to implement the override of normal operations. The memory 217 may comprise random access memory (RAM) dynamic random access memory (DRAM), electrically erasable programmable read-only memory (EEPROM), flash memory, etc.

The IMD 200 may also comprise a stimulation unit 220. The stimulation unit 220 is capable of generating and delivering a variety of electrical signal therapy signals to one or more electrodes via leads. The stimulation unit 220 is capable of delivering a programmed, first electrical signal to the leads 122 coupled to the IMD 200. The electrical signal may be delivered to the leads 122 by the stimulation unit 220 based upon instructions from the controller 210. The stimulation unit 220 may comprise various types of circuitry, such as stimulation signal generators, impedance control circuitry to control the impedance "seen" by the leads, and other circuitry that receives instructions relating to the type of stimulation to be performed.

Signals from sensors (electrodes that are used to sense one or more body parameters such as temperature, heart rate, brain activity, etc.) may be provided to the IMD 200. The body signal data from the sensors may be used by a seizure detection algorithm embedded or processed in seizure detection module 240 to determine whether or not the patient is having and/or has had an epileptic seizure. The seizure detection algorithm may comprise hardware, software, firmware or combinations thereof, and may operate under the control of the controller 210. Although not shown, additional signal conditioning and filter elements (e.g., amplifiers, D/A converters, etc., may be used to appropriately condition the signal for use by the seizure detection module 240. Sensors such as heart sensor 130 and kinetic sensor 140 may be used to detect seizures, along with other autonomic, neurologic, or other body data.

The IMD 200 may also comprise an electrode polarity reversal unit 280. The electrode polarity reversal unit 280 is capable of reversing the polarity of electrodes (125-1, 125-2, 125-3) associated with the electrode assembly 125. The electrode polarity reversal unit 280 is shown in more detail in FIG. 3. In preferred embodiments, the electrode polarity reversal unit is capable of reversing electrode polarity rapidly, i.e., in about 10 microseconds or less, and in any event at a sufficiently rapid rate to permit electrode polarities to be changed between adjacent pulses in a pulsed electrical signal.

The IMD 200 may also comprise a power supply 230. The power supply 230 may comprise a battery, voltage regulators, capacitors, etc., to provide power for the operation of the IMD 200, including delivering the stimulation signal. The power supply 230 comprises a power-source battery that in some embodiments may be rechargeable. In other embodiments, a non-rechargeable battery may be used. The power supply 230 provides power for the operation of the IMD 200, including electronic operations and the stimulation function. The power supply 230 may comprise a lithium/thionyl chloride cell or a lithium/carbon monofluoride (LiCFx) cell. Other battery types known in the art of implantable medical devices may also be used.

The IMD 200 also comprises a communication unit 260 capable of facilitating communications between the IMD 200 and various devices. In particular, the communication unit 260 is capable of providing transmission and reception of electronic signals to and from an external unit 270. The external unit 270 may be a device that is capable of programming various modules and stimulation parameters of the IMD 200. In one embodiment, the external unit 270 comprises a computer system that is capable of executing a data-acquisition program. The external unit 270 may be controlled by a healthcare provider, such as a physician, at a base station in, for example, a doctor's office. The external unit 270 may be a computer, preferably a handheld computer or PDA, but may alternatively comprise any other device that is capable of electronic communications and programming. The external unit 270 may download various parameters and program software into the IMD 200 for programming the operation of the implantable device. The external unit 270 may also receive and upload various status conditions and other data from the IMD 200. The communication unit 260 may be hardware, software, firmware, and/or any combination thereof. Communications between the external unit 270 and the communication unit 260 may occur via a wireless or other type of communication, illustrated generally by line 275 in FIG. 2.

In one embodiment, the communication unit 260 can transmit a log of stimulation data and/or seizure detection data to the patient, a physician, or another party.

Figure 1D:
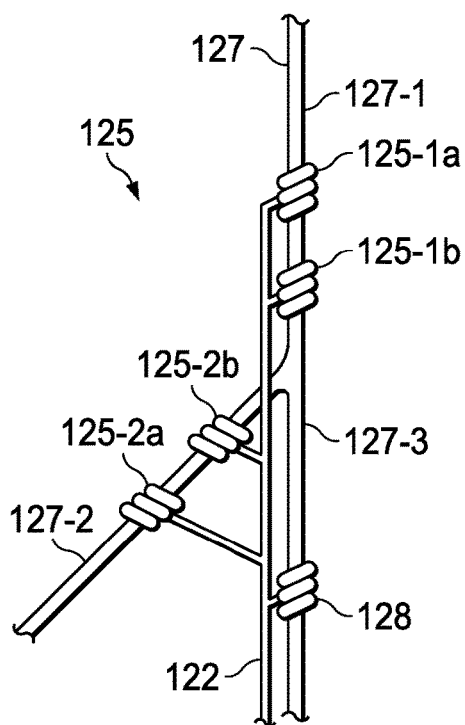
Figure 1E:
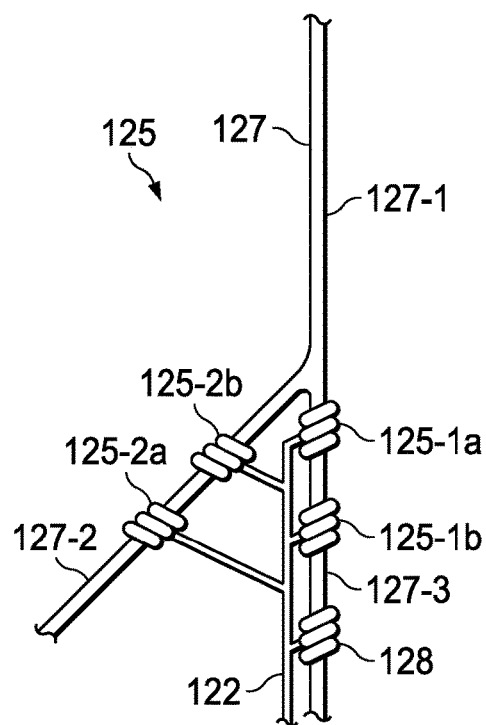

In one embodiment, a method of treating an epileptic seizure is provided that involves providing simultaneously both a first electrical signal to a main trunk of a vagus nerve and a second electrical signal to a cardiac branch of the vagus nerve. As used herein "simultaneously" refers to the on-time of the first and second signals, and does not require that individual pulses of the first signal and the second signal be simultaneously applied to target tissue. The timing of pulses for the first electrical signal and the second electrical signal may be determined by controller 210 in conjunction with stimulation unit 220. Where active charge-balancing is used, it may be possible to use the active charge-balancing phase of pulses of the first electrical signal as the stimulation phase of the second electrical signal by selecting a current magnitude of the cathode in the charge-balancing phase (typically a second electrode, which may be the anode of the initial stimulation phase) that is sufficient to generate action potentials in nerve fibers of the target tissue. Controller 210 may in some embodiments provide simultaneous delivery of first and second electrical signals by interleaving pulses for each of the first and second electrical signals based upon the programmed timing of pulses for each signal and the appropriate polarity of each of first and second electrodes 125-1 and 125-2. In some embodiments, additional electrodes may be used to minimize the induction of action potentials to the heart or the brain provided by the first electrical signal or the second electrical signal. This may be accomplished, in one embodiment, by using an anode located on either the upper main trunk or the cardiac branch to block impulse conduction to the heart or brain from the cathode, or by providing dedicated electrode pairs on both the main trunk and cardiac branches (FIGS. 1D, 1E). When beneficial, steps to avoid collisions of actions potentials travelling in opposite directions may be implemented, while steps to promote collisions may be taken when clinically indicated. In some embodiments, the method further includes sensing a cardiac signal and a kinetic signal of the patient, and detecting a seizure event with a seizure detection algorithm.

In one embodiment, a first electrical signal is applied to a main trunk of a vagus nerve and a second electrical signal is simultaneously applied to a cardiac branch of a vagus nerve. A pulse of the first electrical signal is generated with the electrical signal generator 110 and applied to the main trunk of the vagus nerve using a first electrode (e.g., 125-1, 125-1a) as a cathode and a second electrode (e.g., 125-1b, 125-3, or 125-2) as an anode. The method includes sensing a cardiac signal and a kinetic signal of the patient, and detecting a seizure event with a seizure detection algorithm. A pulse of the second electrical signal (having the appropriate pulse width and current) is generated and applied (under appropriate timing control by controller 110 and stimulation unit 220) to the cardiac branch of the vagus nerve using a second electrode (e.g., 125-2, 125-2a) as a cathode and another electrode (e.g., 125-3, 125-1, 125-2b) as an anode. Another pulse of the first electrical signal may thereafter be generated and applied to the main trunk under timing and parameter control of controller 210 and stimulation unit 220. By appropriate selection of cathodes and anodes, the first and second electrical signals may be interleaved and provided simultaneously to the main trunk and cardiac branches of the vagus nerve. In some embodiments, the number of electrodes may be minimized by provided a polarity reversal unit that may rapidly change the polarity of particular electrodes to allow their use in delivering both the first and second signals.

The IMD 200 is capable of delivering stimulation that can be contingent, periodic, random, coded, and/or patterned. The stimulation signals may comprise an electrical stimulation frequency of approximately 0.1 to 10,000 Hz. The stimulation signals may comprise a pulse width in the range of approximately 1-2000 micro-seconds. The stimulation signals may comprise current amplitude in the range of approximately 0.1 mA to 10 mA. Appropriate precautions may be taken to avoid delivering injurious current densities to target neural tissues, e.g., by selecting current, voltage, frequency, pulse width, on-time and off-time parameters to maintain current density below thresholds for damaging tissues.

The IMD 200 may also comprise a magnetic field detection unit 290. The magnetic field detection unit 290 is capable of detecting magnetic and/or electromagnetic fields of a predetermined magnitude. Whether the magnetic field results from a magnet placed proximate to the IMD 200, or whether it results from a substantial magnetic field encompassing an area, the magnetic field detection unit 290 is capable of informing the IMD of the existence of a magnetic field. The changeable electrode polarity stimulation described herein may be activated, deactivated, or alternatively activated or deactivated using a magnetic input.

The magnetic field detection unit 290 may comprise various sensors, such as a Reed Switch circuitry, a Hall Effect sensor circuitry, and/or the like. The magnetic field detection unit 290 may also comprise various registers and/or data transceiver circuits that are capable of sending signals that are indicative of various magnetic fields, the time period of such fields, etc. In this manner, the magnetic field detection unit 290 is capable of detecting whether the detected magnetic field relates to an input to implement a particular first or second electrical signal (or both) for application to the main trunk of cardiac branches, respectively, of the vagus nerve.

One or more of the blocks illustrated in the block diagram of the IMD 200 in FIG. 2, may comprise hardware units, software units, firmware units, or any combination thereof. Additionally, one or more blocks illustrated in FIG. 2 may be combined with other blocks, which may represent circuit hardware units, software algorithms, etc. Additionally, one or more of the circuitry and/or software units associated with the various blocks illustrated in FIG. 2 may be combined into a programmable device, such as a field programmable gate array, an ASIC device, etc.

Figure 3:
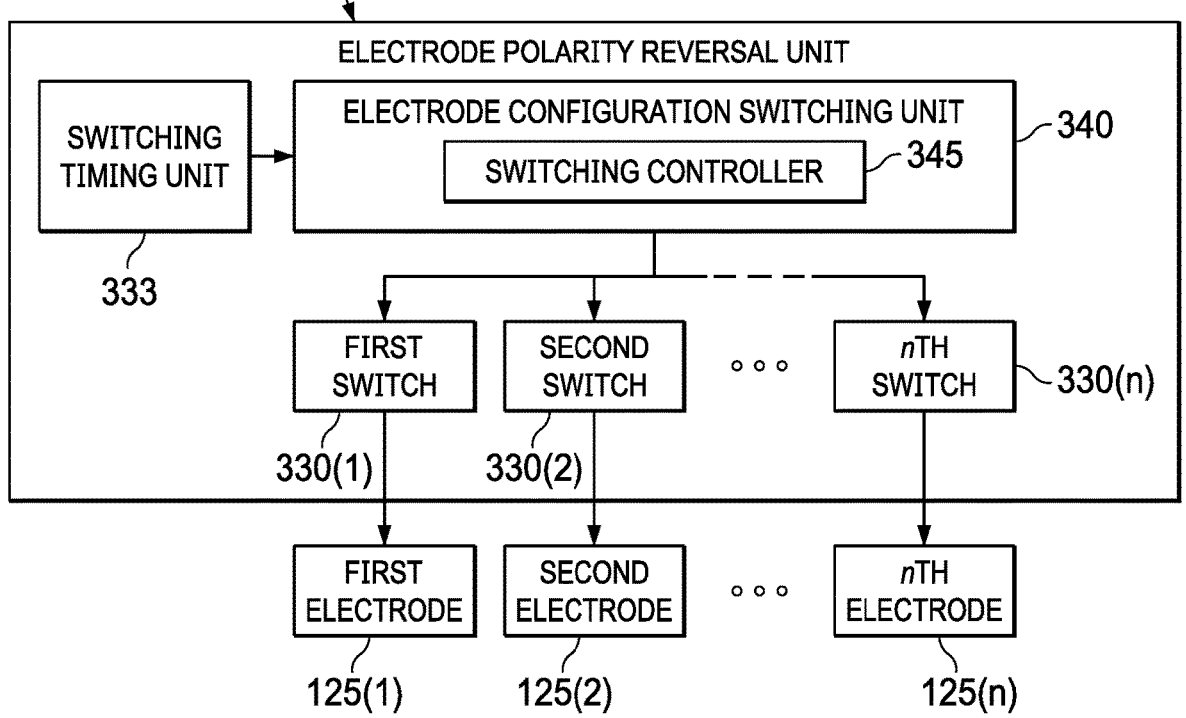
FIG. 3 illustrates a block diagram depiction of an electrode polarity reversal unit shown in FIG. 2, in accordance with one illustrative embodiment of the present disclosure.

FIG. 3 shows in greater detail an electrode polarity reversal unit 280 (FIG. 2) in one embodiment. The electrode polarity reversal unit 280 comprises an electrode configuration switching unit 340, which includes a switching controller 345. The switching controller 345 transmits signals to one or more switches, generically, n switches 330(1), 330(2), . . . 330(n) which effect the switching of the configuration of two or more electrodes, generically, n electrodes 125(1), 125(2), . . . 125(n). Although FIG. 3 shows equal numbers of switches 330 and electrodes 125, persons of skill in the art having the benefit of the present disclosure will understand that the number of switches 330 and their connections with the various electrodes 125 can be varied as a matter of routine optimization. A switching timing unit 333 can signal to the electrode configuration switching unit 340 that a desired time for switching the electrode configuration has been reached.

Instructions for implementing two or more stimulation regimens, which may include at least one open-loop electrical signal and at least one closed-loop electrical signal, may be stored in the IMD 200. These stimulation signals may include data relating to the type of stimulation signal to be implemented. In one embodiment, an open-loop signal may be applied to generate action potentials for modulating the brain of the patient, and a closed-loop signal may be applied to generate either action potentials for slowing the heart rate of the patient, or both action potentials to modulate the brain of the patient as well as action potentials for slowing the heart rate of the patient. In some embodiments, the open-loop and closed-loop signals may be provided to different target portions of a vagus nerve of the patient by switching the polarity of two or more electrodes using an electrode polarity reversal unit as described in FIG. 3 above. In alternative embodiments, additional electrodes may be provided to generate each of the open-loop and closed-loop signals without electrode switching.

In one embodiment, a first open-loop mode of stimulation may be used to provide an electrical signal to a vagus nerve using a first electrode as a cathode on a main trunk (e.g., 127-1 or 127-3 using electrodes 125-1 or 125-3, respectively) of a vagus nerve, and a second electrode as an anode on either a main trunk (e.g., electrode 125-3, when electrode 125-1 is used as a cathode) or cardiac branch (e.g., electrode 125-2) of a vagus nerve. The first open-loop signal may include a programmed on-time and off-time during which electrical pulses are applied (the on-time) and not-applied (the off-time) in a repeating sequence to the vagus nerve.

A second, closed-loop signal may be provided in response to a detected event (such as an epileptic seizure, particularly when accompanied by an increase in the patient's heart rate) using a different electrode configuration than the first, open-loop signal. In one embodiment, the second, closed-loop signal is applied to a cardiac branch using the second electrode 125-2 as a cathode and the first electrode on the main trunk (e.g., 125-1 or 125-3) as an anode. The second, closed-loop signal may involve generating efferent action potentials on the cardiac branch of the vagus nerve to slow the heart rate. In some embodiments, the first, open-loop signal may be interrupted/suspended in response to the detected event, and only the second, closed-loop signal is applied to the nerve. In other embodiments, the first, open loop signal may not be interrupted when the event is detected, and both the first, open-loop signal and the second, closed-loop signal are applied to the vagus nerve. In another embodiment, a third, closed-loop signal may also be provided in response to the detected event. The third, closed-loop signal may involve an electrical signal using the same electrode configuration as the first, open-loop electrical signal, but may provide a different electrical signal to the main trunk of the vagus nerve than either the first, open-loop signal or the second, closed-loop signal. The first, open-loop signal may be interrupted, terminated or suspended in response to the detected event, and the third, closed-loop signal may be applied to the nerve either alone or with the second, closed-loop signal. In some embodiments, both the second and third closed-loop signals may be provided in response to a detected epileptic seizure by rapidly changing the polarity of the first (125-1) and second (125-2) electrodes from cathode to anode and back, as pulses are provided as part of the second and third electrical signals, respectively. In one embodiment, the third electrical signal may involve modulating the brain by using a main trunk electrode (e.g., upper main trunk electrode 125-1) as a cathode and another electrode (e.g., cardiac branch electrode 125-2 or lower main trunk electrode 125-3) as an anode. The third electrical signal may comprise, for example, a signal that is similar to the first electrical signal but which provides a higher electrical current than the first electrical signal, and for a longer duration than the first signal or for a duration that is adaptively determined based upon a sensed body signal (in contrast, for example, to a fixed duration of the first electrical signal determined by a programmed on-time). By rapidly changing polarity of the electrodes, pulses for each of the second and third electrical signals may be provided such that the second and third signals are provided simultaneously to the cardiac branch and main trunk of the vagus nerve. In other embodiments, the first, second and third electrical signals may be provided sequentially rather than simultaneously.

In some embodiments, one or more of the first, second and third electrical signals may comprise a microburst signal, as described more fully in U.S. patent application Ser. Nos. 11/693,421, 11/693,451, and 11/693,499, each filed Mar. 29, 2007 and each hereby incorporated by reference herein in their entirety.

In one embodiment, each of a plurality of stimulation regimens may respectively relate to a particular disorder, or to particular events characterizing the disorder. For example, different electrical signals may be provided to one or both of the main trunk and cardiac branches of the vagus nerve depending upon what effects accompany the seizure. In a particular embodiment, a first open-loop signal may be provided to the patient in the absence of a seizure detection, while a second, closed-loop signal may be provided when a seizure is detected based on a first type of body movement of the patient as detected by, e.g., an accelerometer, a third, closed-loop signal may be provided when the seizure is characterized by a second type of body movement, a fourth, closed-loop signal may be provided when the seizure is characterized by an increase in heart rate, a fifth, closed-loop signal may be provided when the seizure is characterized by a decrease in heart rate, and so on. More generally, stimulation of particular branches or main trunk targets of a vagus nerve may be provided based upon different body signals of the patient. In some embodiments, additional therapies may be provided based on different events that accompany the seizure, e.g., stimulation of a trigeminal nerve or providing a drug therapy to the patient through a drug pump. In one embodiment, different regimens relating to the same disorder may be implemented to accommodate improvements or regressions in the patient's present condition relative to his or her condition at previous times. By providing flexibility in electrode configurations nearly instantaneously, the present disclosure greatly expands the range of adjustments that may be made to respond to changes in the patient's underlying medical condition.

The switching controller 345 may be a processor that is capable of receiving data relating to the stimulation regimens. In an alternative embodiment, the switching controller may be a software or a firmware module. Based upon the particulars of the stimulation regimens, the switching timing unit 333 may provide timing data to the switching controller 345. The first through nth switches 330(1-n) may be electrical devices, electro-mechanical devices, and/or solid state devices (e.g., transistors).

Figure 4:
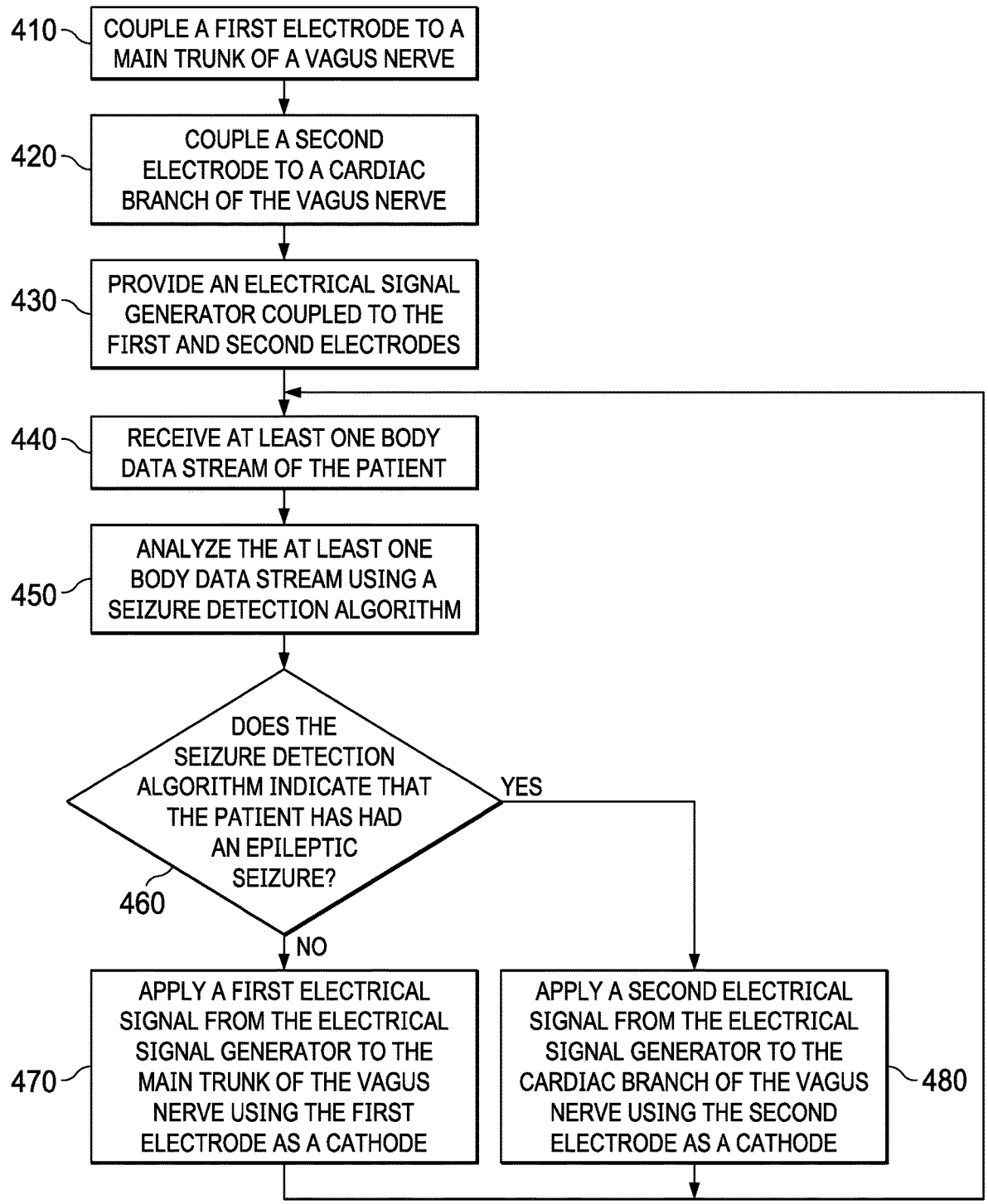
FIG. 4 illustrates a flowchart depiction of a method for providing first and second electrical signals to a main trunk and a cardiac branch of a vagus nerve, respectively, based upon whether or not the patient is having and/or has had an epileptic seizure, in accordance with an illustrative embodiment of the present disclosure.

FIG. 4 shows one embodiment of a method of treating a patient having epilepsy according to the present disclosure. In this embodiment, a first electrode is coupled to a main trunk of a vagus nerve of the patient (410) and a second electrode is coupled to a cardiac branch of the vagus nerve (420). An electrical signal generator is coupled to the first and second electrodes (430).

The method further involves receiving at least one body data stream of the patient (440). The data may be sensed by a sensor such as heart rate sensor 130 (FIG. 1A) or a sensor that is an integral part of, or coupled to, an IMD 200 (FIG. 2) such as electrical pulse generator 110 (FIG. 1A), and the IMD may also receive the data from the sensor. The at least one body data stream is then analyzed using a seizure detection algorithm (450), and the seizure detection algorithm determines whether or not the patient is having and/or has had an epileptic seizure (460).

If the algorithm indicates that the patient is not having and/or has not had an epileptic seizure, the method comprises applying a first electrical signal from the electrical signal generator to the main trunk of a vagus nerve using the first electrode as a cathode (470). In one embodiment, applying the first electrical signal comprises continuing to apply a programmed, open-loop electrical signal periodically to the main trunk of the vagus nerve according a programmed on-time and off-time.

If the algorithm indicates that the patient is having and/or has had an epileptic seizure, the method comprises applying a second electrical signal from the electrical signal generator to the cardiac branch of the vagus nerve using the second electrode as a cathode (480). Depending upon which electrical signal (first or second) is applied, the method may involve changing the polarity of one or both of the first electrode and the second electrode. In one embodiment, the method may comprise suspending the first electrical and applying the second electrical signal. In one embodiment, the method comprises continuing to receive at least one body data stream of the patient at 440 after determining whether or not the patient is having and/or has had an epileptic seizure.

In an alternative embodiment, if the seizure detection algorithm indicates that the patient is having and/or has had an epileptic seizure, both the first electrical signal and the second electrical signal are applied to the main trunk and cardiac branches of a vagus nerve of the patient, respectively, at step 480. In a specific implementation of the alternative embodiment, pulses of the first and second electrical signal are applied to the main trunk and cardiac branch of the vagus nerve under the control of controller 210 by rapidly changing the polarity of the first and second electrodes using the electrode polarity reversal unit 280 to apply the first electrical signal to the main trunk using the first electrode as a cathode and the second electrode as an anode, changing the polarity of the first and second electrodes, and applying the second electrical signal to the cardiac branch using the second electrode as a cathode and the first electrode as an anode. Additional pulses for each signal may be similarly applied by rapidly changing the polarity of the electrodes.

In some embodiments, the first electrical signal and the second electrical signal are applied unilaterally, i.e., to a vagal main trunk and a cardiac branch on the same side of the body. In other embodiments, the first and second electrical signals are applied bilaterally, i.e., the second electrical signal is applied to a cardiac branch on the opposite side of the body from the main vagal trunk to which the first electrical signal is applied. In one embodiment, the first electrical signal is applied to a left main trunk to minimize cardiac effects of the first electrical signal, and the second electrical signal is applied to a right cardiac branch, which modulates the sinoatrial node of the heart to maximize cardiac effects of the second electrical signal.

In alternative embodiments, both the first electrode and the second electrode may be coupled to a cardiac branch of a vagus nerve, with the first electrode (e.g., anode) being proximal to the brain relative to the second electrode, and the second electrode (e.g., cathode) being proximal to the heart relative to the first electrode.

Figure 5:
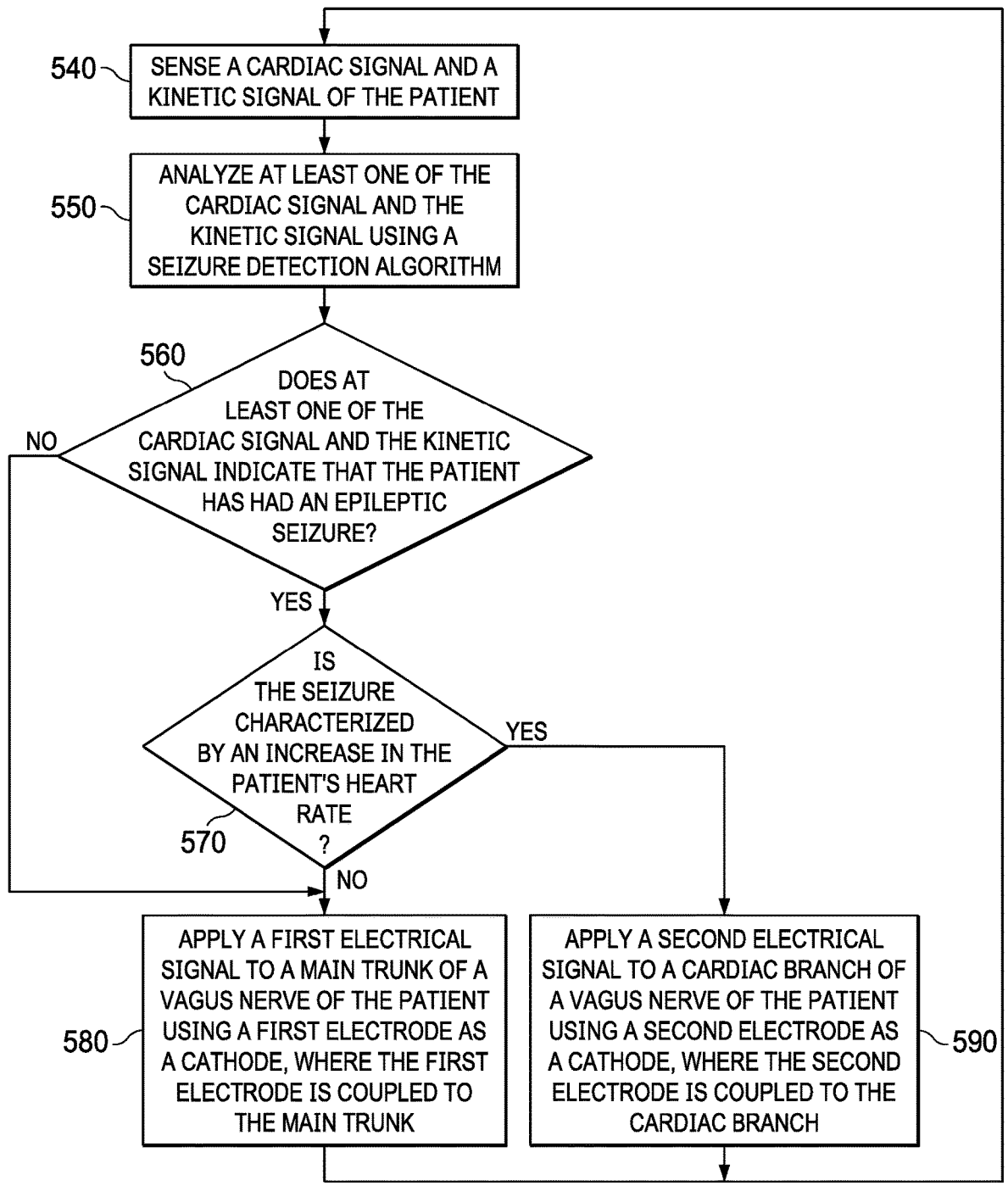
FIG. 5 illustrates a flowchart depiction of a method for providing first and second electrical signals to a main trunk and a cardiac branch of a vagus nerve, respectively, based upon whether or not at least one of a cardiac signal and a kinetic signal indicates that the patient is having and/or has had an epileptic seizure, and whether the seizure is characterized by an increase in heart rate, in accordance with an illustrative embodiment of the present disclosure.

FIG. 5 is a flow diagram of another method of treating a patient having epilepsy according to the present disclosure. A sensor is used to sense a cardiac signal and a kinetic signal of the patient (540). In a particular embodiment, the cardiac sensor may comprise an electrode pair for sensing an ECG (electrocardiogram) or heart beat signal, and the kinetic signal may comprise a triaxial accelerometer to detect motion of at least a portion of the patient's body. The method further comprises analyzing at least one of the cardiac signal and the kinetic signal using seizure detection algorithm (550), and the output of the algorithm is used to determine whether at least one of the cardiac signal and the kinetic signal indicate that the patient is having and/or has had an epileptic seizure (560).

If the patient is not having and/or has not had an epileptic seizure, the method comprises applying a first electrical signal to a main trunk of a vagus nerve of the patient using a first electrode, coupled to the main trunk, as a cathode (580). In one embodiment, the first electrical signal is an open-loop electrical signal having an on-time and off-time.

If the patient is having and/or has had an epileptic seizure, a determination is made whether the seizure is characterized by an increase in the patient's heart rate (570). If the seizure is not characterized by an increase in the patient's heart rate, the method comprises applying the first electrical signal to the main trunk of a vagus nerve using the first electrode as a cathode (580). In one embodiment, the cathode comprises an upper main trunk electrode 125-1 and the anode is selected from a cardiac branch electrode 125-2 and a lower main trunk electrode 125-3. Conversely, if the seizure is characterized by an increase in the patient's heart rate, the method comprises applying a second electrical signal to a cardiac branch of a vagus nerve of the patient using a second electrode, coupled to the cardiac branch, as a cathode (590). The anode is an upper main trunk electrode 125-1 or a lower main trunk electrode 125-3. In one embodiment, the method may comprise suspending the first electrical and applying the second electrical signal.

The method then continues the sensing of the cardiac and kinetic signals of the patient (540) and resumes the method as outlined in FIG. 5.

Figure 6:
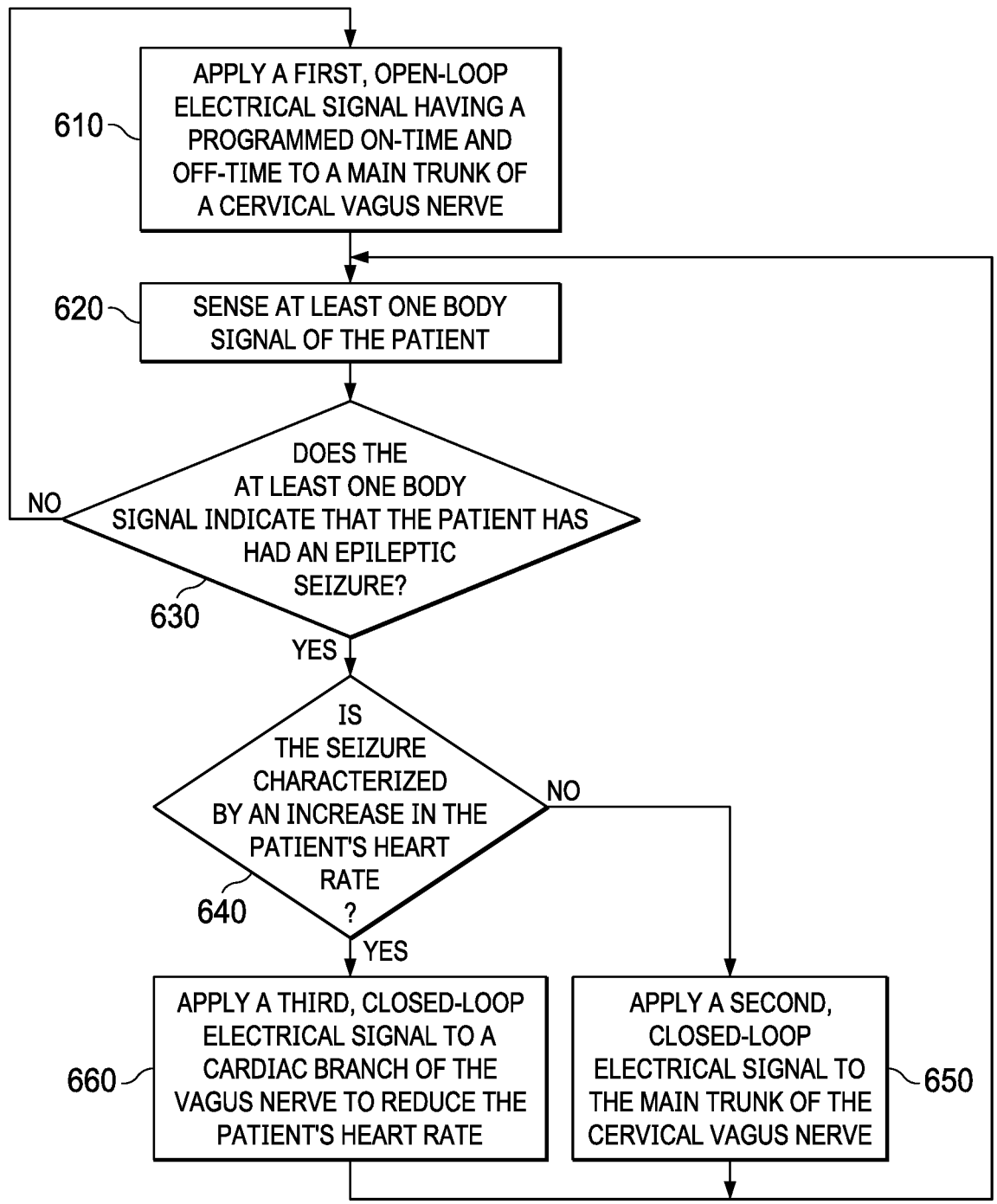
FIG. 6 illustrates a flowchart depiction of a method for providing a first, open-loop electrical signal to a main trunk of a vagus nerve, a second, closed-loop electrical signal to the main trunk of the vagus nerve based upon the patient having had an epileptic seizure not characterized by an increase in heart rate, and a third, closed-loop electrical signal to a cardiac branch of a vagus nerve based upon the patient having had an epileptic seizure characterized by an increase in heart rate, in accordance with an illustrative embodiment of the present disclosure.

FIG. 6 is a flow diagram of a further method of treating a patient having epilepsy according to the present disclosure. The method includes applying a first, open-loop electrical signal to a main trunk of a vagus nerve (610). The open-loop signal is characterized by an off-time in which electrical pulses are applied to the nerve, and an off-time in which electrical pulses are not applied to the nerve.

A sensor is used to sense at least one body signal of the patient (620), and a determination is made whether the at least one body signal indicates that the patient is having and/or has had an epileptic seizure (630). If the patient is not having and/or has not had a seizure, the method continues applying the first, open-loop electrical signal to a main trunk of a vagus nerve (610). If the patient is having and/or has had an epileptic seizure, a determination is made whether the seizure is characterized by an increase in the patient's heart rate (640). In one embodiment, the increase in heart rate is measured from a baseline heart rate existing prior to the seizure, e.g., a median heart rate for a prior period such as the 300 beats prior to the detection of the seizure event, or the 5 minutes prior to the detection of the seizure.

If the seizure is not characterized by an increase in the patient's heart rate, the method comprises applying a second, closed-loop electrical signal to the main trunk of the vagus nerve 650). In one embodiment, the second, closed-loop electrical signal is the same signal as the open-loop electrical signal, except that the second signal (as defined, e.g., by a current intensity, a pulse frequency, a pulse width and an on-time) is applied at a time different from the programmed timing of the first electrical signal. For example, if the first electrical signal comprises an on-time of 30 seconds and an off-time of 5 minutes, but a seizure is detected 1 minute after the end of a programmed on-time, the second electrical signal may comprise applying a 30 second pulse burst at the same current intensity, frequency, and pulse width as the first signal, but four minutes earlier than would have occurred absent the detected seizure. In another embodiment, the second, closed-loop electrical signal is a different signal than the first, open-loop electrical signal, and the method may also comprise suspending the first electrical before applying the second electrical signal. For example, the second, closed-loop electrical signal may comprise a higher current intensity, frequency, pulse width and/or on-time than the first, open-loop electrical signal, and may not comprise an off-time (e.g., the second electrical signal may be applied for a predetermined duration independent of the on-time of the first, open-loop electrical signal, such as a fixed duration of 1 minute, or may continue for as long as the body signal indicates the presence of the seizure event).

Returning to FIG. 6, if the seizure is characterized by an increase in the patient's heart rate, the method comprises applying a third, closed-loop electrical signal to a cardiac branch of a vagus nerve to reduce the patient's heart rate (660). The method may comprise suspending the first electrical as well as applying the third, closed-loop electrical signal. In one embodiment of the disclosure, each of the first, open-loop electrical signal, the second, closed-loop electrical signal, and the third, closed-loop electrical signal are applied unilaterally (i.e., to vagus nerve structures on the same side of the body) to the main trunk and cardiac branch of the vagus nerve. For example, the first, open-loop electrical signal and the second, closed-loop electrical signal may be applied to a left main trunk of the patient's cervical vagus nerve, and the third, closed-loop electrical signal may be applied to the left cardiac branch of the vagus nerve. Similarly, the first, second and third electrical signals may all be applied to the right vagus nerve of the patient. In alternative embodiments, one or more of the first, second and third electrical signals may be applied bilaterally, i.e., one of the first, second and third electrical signals is applied to a vagal structure on the opposite side of the body from the other two signals. For example, in a particular embodiment the first, open-loop signal and the second, closed-loop signal may be applied to a left main trunk of the patient's cervical vagus nerve, and the third, closed-loop electrical signal may be applied to a right cardiac branch of the patient's vagus nerve. Because the right cardiac branch modulates the sinoatrial node of the patient's heart, which is the heart's "natural pacemaker," the third electrical signal may have more pronounced effect in reducing the patient's heart rate if applied to the right cardiac branch.

After applying one of the second (650) and third (660) electrical signals to a vagus nerve of the patient, the method then continues sensing at least one body signal of the patient (620) and resumes the method as outlined in FIG. 6.

In the methods depicted in FIGS. 4-6, one or more of the parameters defining the first, second, and third electrical signals (e.g., number of pulses, pulse frequency, pulse width, On time, Off time, interpulse interval, number of pulses per burst, or interburst interval, among others) can be changed by a healthcare provided using a programmer 150.

Figure 7:
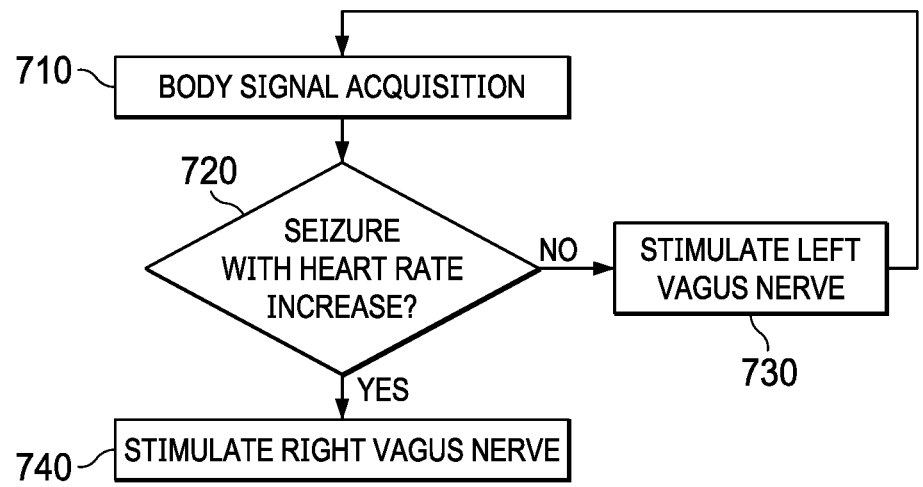
FIG. 7 is a flowchart depiction of a method for providing closed-loop vagus nerve stimulation for a patient with epilepsy by stimulating a right vagus nerve in response to detecting a seizure with tachycardia and stimulating a left vagus nerve in the absence of such a detection. For example if a recumbent person's heart rate is 55 bpm and it increases to 85 during a seizure, this is not clinical/pathological tachycardia, but may be considered tachycardia within the meaning of some embodiments of the present disclosure.

FIG. 7 is a flow diagram of a method of treating patients having seizures accompanied by increased heart rate. In one embodiment, tachycardia is defined as a neurogenic increase in heart rate, that is, an elevation in heart rate that occurs in the absence of motor activity or that if associated with motor activity, the magnitude of the increase in heart rate is larger than that caused by motor activity alone. In one embodiment, a body signal is acquired (710). The body signal may comprise one or more body signals that may be altered, changed or influenced by an epileptic seizure. As non-limiting examples, the body signal may comprise one or more of a cardiac signal such as heart rate, heart rate variability, or EKG complex morphology, a kinetic signal such as an accelerometer signal, a postural signal or body position signal), blood pressure, blood oxygen concentration, skin resistivity or conductivity, pupil dilation, eye movement, EEG, reaction time or other body signals. The body signal may be a real-time signal or a stored signal for delayed or later analysis. It may be acquired, for example, from a sensor element (e.g., coupled to a processor), from a storage device in which the signal data is stored.

The method further comprises determining whether or not the patient is having and/or has had a seizure accompanied by an increase in heart rate (720). In one embodiment, the method comprises a seizure detection algorithm that analyzes the acquired body signal data and determines whether or not a seizure has occurred. In a particular embodiment, the method comprises an algorithm that analyzes one or more of a cardiac signal, a kinetic signal, a cognitive signal, blood pressure, blood oxygen concentration, skin resistivity or conductivity, pupil dilation, and eye movement to identify changes in the one or more signals that indicate a seizure has occurred. The method may comprise an output signal or data flag that may be asserted or set when the detection algorithm determines from the body signal(s) that the patient is having and/or has had a seizure.

The method also comprises determining (720) whether or not the seizure is accompanied by an increase in heart rate. In one embodiment, the body data signal comprises a heart beat signal that may be analyzed to determine heart rate. In some embodiments, the heart beat signal may be used by the seizure detection algorithm to determine whether a seizure has occurred, while in other embodiments seizures are not detected using heart rate. Regardless of how the seizure is detected, however, the method of FIG. 7 comprises determining whether a detected seizure event is accompanied by an increase in heart rate. The increase may be determined in a variety of ways, such as by an increase in an instantaneous heart rate above a reference heart rate (which may be a predetermined interictal value such as 72 beats per minute (bpm), or a real-time measure of central tendency for a time window, such as a 5 minute median or moving average heart rate). Additional details about identifying increases in heart rate in the context of epileptic seizures are provided in U.S. Pat. Nos. 5,928,272, 6,341,236, 6,587,727, 6,671,556, 6,961,618, 6,920,357, 7,457,665, as well as U.S. patent application Ser. Nos. 12/770,562, 12/771,727, 12/771,783, 12/884,051, 12/886,419, 12/896,525, 13/098,262, and 13/288,886, each of which is hereby incorporated by reference in its entirety herein.

If the body data signal does not indicate that the patient is having and/or has had a seizure accompanied by tachycardia, the method comprises applying a first electrical signal to a left vagus nerve. If the body signal does indicate that the patient has experienced a seizure accompanied by tachycardia, the method comprises applying a second electrical signal to a right vagus nerve.

Without being bound by theory, it is believed that stimulation of the right vagus nerve, which enervates the right sinoatrial nerve that functions as the heart's natural pacemaker, will have a more prominent effect in slowing the heart rate than stimulation of the left vagus nerve. The present disclosure takes advantage of this electrical asymmetry of the left and right vagus nerves to minimize the effect of VNS on heart rate except where there is a need for acute intervention to slow the heart rate, i.e., when the patient has experienced and epileptic seizure, and the seizure is accompanied by an increase in heart rate. This may result in, for example, stimulation of the left vagus nerve either when there is no seizure (such as when an open-loop stimulation program off-time has elapsed and the program initiates stimulation in accordance with a programmed signal on-time), or when there is a detected seizure event that is not accompanied by an increase in heart rate (such as absence seizures); and stimulation of the right vagus nerve when there is a detected seizure event accompanied by a heart rate increase. In one embodiment, a programmed, open-loop electrical signal is applied to the left vagus nerve except when an algorithm analyzing the acquired body signal detects a seizure accompanied by a heart rate increase. In response to such a detection, a closed-loop electrical signal is applied to the right vagus nerve to slow the patient's (increased) heart rate. In some embodiments, the response to detecting a seizure accompanied by a heart rate increase may also include interrupting the application of the programmed-open-loop electrical signal to the left vagus nerve. The interrupted open-loop stimulation of the left vagus nerve may be resumed either when the seizure ends or the heart rate returns to a desired, lower heart rate.

In an additional embodiment of the disclosure, electrode pairs may be applied to each of the left and right vagus nerves of the patient, and used depending upon whether or not seizures accompanied by cardiac changes such as tachycardia are detected.

Figure 8:
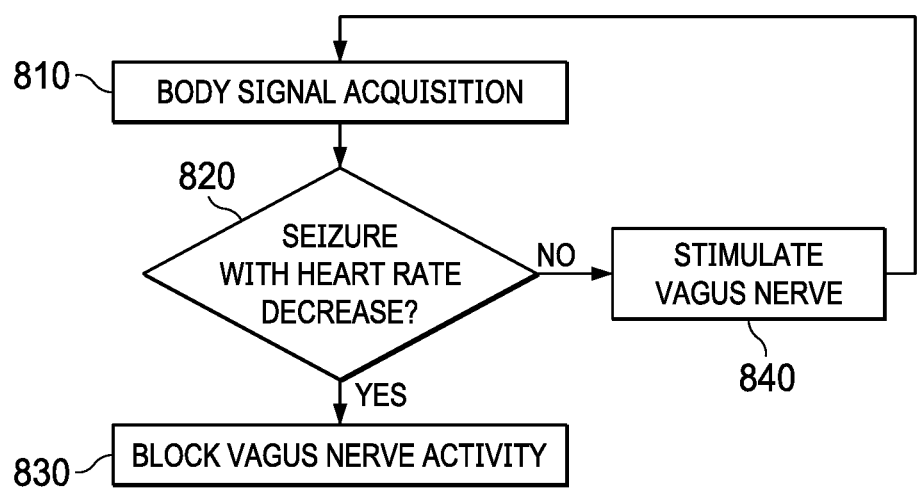
FIG. 8 is a flowchart depiction of a method for providing a closed-loop therapy to a vagus nerve of a patient with epilepsy in response to detecting a seizure associated with a heart rate decrease, wherein said therapy blocks impulse conduction along at least one vagus nerve.

FIG. 8 is a flowchart depiction of a method of treating patients having seizures accompanied by a relative or absolute decrease in heart rate (i.e., a bradycardia episode). Epileptic seizures originating from certain brain regions may trigger decreases in heart rate of a magnitude sufficient to cause loss of consciousness and of postural tone (i.e., syncope). In some subjects the cerebral ischemia associated with the bradycardia may in turn lead to convulsions (i.e., convulsive syncope). If bradycardia-inducing seizures are not controllable by medications, the current treatment is implantation of a demand cardiac pacemaker. In one embodiment of the present disclosure, ictal bradycardia may be treated by preventing vagal nerve impulses from reaching the heart, either by preventing impulses traveling through all fiber types contained in the trunk of the nerve or in one of its branches, or by only blocking impulses within a certain fiber type. In another embodiment, the degree of the nerve impulse blocking within a vagus nerve may be determined based upon the magnitude of bradycardia (e.g., the larger the bradycardia change from the pre-existing baseline heart rate, the larger the magnitude of the block) so as to prevent tachycardia from occurring.

In one embodiment, a body signal is acquired (810). The body signal may comprise one or more body signals that may be altered, changed or influenced by an epileptic seizure. Changes in the body signal may be used to detect the onset or impending onset of seizures. As noted with reference to FIG. 7, the body signal may comprise one or more measure derived from a cardiac signal (e.g., heart rate, heart rate variability, change in EKG morphology), a kinetic signal (e.g., an accelerometer, force of muscle contraction, posture or body position signal), blood pressure, blood oxygen concentration, skin resistivity/conductivity, pupil dilation, eye movement, or other body signals. The body signal may be a real-time signal, a near-real-time signal, or a non-real-time signal, although in preferred embodiments, the signal is a real-time signal or a near-real-time signal. The signal may be acquired from a sensor element (e.g., coupled to a processor) or from a storage device.

Referring again to FIG. 8, the method further comprises determining whether or not the patient is having and/or has had a seizure that is accompanied by a decrease in heart rate (820). In one embodiment, the method comprises using a seizure detection algorithm using one or more of a cardiac, kinetic, neurologic, endocrine, metabolic or tissue stress marker to detect seizures, and to determine if the seizure is associated with a decrease in heart rate. In a particular embodiment, an algorithm—which may comprise software and/or firmware running in a processor in a medical device—analyzes one or more of a cardiac signal, a kinetic signal, blood pressure, blood oxygen concentration, skin resistivity or conductivity, pupil dilation, and eye movement to identify changes in the one or more signals that indicate the occurrence of an epileptic seizure. Such changes may be identified by determining one or more indices from the foregoing signals, such as a cardiac index (e.g., a heart rate), a kinetic index (e.g., a kinetic level or motion type, a magnitude of an acceleration or force, or other indices that may be calculated from an accelerometer signal). The method may include providing an output signal or setting a data flag when the detection algorithm determines from the body signal(s) that the patient is having and/or has had a seizure. In a preferred embodiment, the seizure detection occurs in real time and the output signal or data flag is set immediately upon detection of the seizure.

Once it is determined that the patient is having and/or has had a seizure, the method also comprises determining if the seizure is accompanied by a decrease in heart rate. In one embodiment, the acquired body data signal (810) comprises a heart beat signal that may be analyzed to determine heart rate. In some embodiments, the acquired heart beat signal may be used by the seizure detection algorithm to determine whether a seizure has occurred, while in other embodiments seizures are determined without regard to the patient's heart rate. Regardless of how the seizure is determined, the method of FIG. 8 comprises determining whether a detected seizure event is accompanied by a decrease in heart rate (820). The decrease in heart rate may be determined in a variety of ways, such as by a decrease in an instantaneous heart rate below a reference heart rate value (which may be a predetermined interictal value such as 72 beats per minute (bpm), or a real-time measure of central tendency for a time window or number-of-beats window (e.g., a 5 minute median or moving average heart rate, or a media heart rate for a window selected from 3-300 beats such as a 5, 10, or 300 beat window)). Additional details about identifying decreases in heart rate in the context of epileptic seizures are provided in U.S. patent application Ser. Nos. 12/770,562, 12/771,727, 12/771,783, 12/884,051, 12/886,419, 13/091,033, each of which is hereby incorporated by reference in its entirety herein.

In one embodiment, if the acquired body data signal does not indicate that the patient is having and/or has had a seizure accompanied by a HR decrease, the method comprises applying a first electrical signal to a vagus nerve (840), wherein the first electrical signal is sufficient to generate exogenous action potentials in fibers of the vagus nerve. The second electrical signal is a therapeutic electrical signal to treat the seizure. It may be applied to either the left or right vagus nerves, or both. The first electrical signal may be a signal defined by, among other parameters, an on-time during which electrical pulses are applied to the nerve, and an off-time during which no pulses are applied to the nerve. In some embodiments, the on-time may be determined by the duration and intensity of the change in heart rate, while in other embodiments it may be pre-programmed Cathode(s) and anode(s) may be placed on the nerve trunks or branches to maximize flow of exogenously generated nerve impulses in a caudal direction (for control of heart rate changes) and a cephalic direction for seizure treatment.

If the body signal indicates that the patient is having and/or has had a seizure accompanied by a decrease in heart rate, the method comprises applying an action to decrease vagal/parasympathetic tone. In one embodiment, the method comprises blocking the passage of impulses through at least one of a vagus nerve trunk or branch. This may be accomplished by applying one or more of a second electrical signal (e.g., a high frequency electrical signal), a thermal signal (e.g., cooling), a chemical signal (e.g., applying a local anesthetic), and/or a mechanical signal (e.g., applying pressure or a vibration) to a vagus nerve of the patient (830). In another embodiment, the method comprises delivering at least one of an anti-cholinergic drug or a sympatho-mimetic drug.

As used herein, blocking vagus nerve activity means blocking intrinsic or native vagal activity (i.e., blocking action potentials not artificially or exogenously induced by an electrical signal generated by a device). The blocking signal may block the conduction of action potentials in all or at least some portion or fraction of the axons of a vagus nerve. In general, such blocking signals are incapable of inducing exogenous action potentials in the axons of the vagus nerve. In one embodiment, the blocking signal may comprise a high frequency, pulsed electrical signal, the pulse frequency being sufficient to inhibit propagation of at least some action potentials in vagus nerve fibers. The electrical signal may comprise a signal in excess of 300 Hz, or other frequency, so long as the frequency and other stimulation signal parameters (such as pulse width and pulse current or voltage) provide a signal capable of inhibiting some or all of the action potentials propagating along fibers of the vagus nerve. In alternative embodiments, the electrical signal may comprise generating unidirectional action potentials for collision blocking of endogenous action potentials.

High frequency vagus nerve stimulation (or other blocking signals such as collision blocking) may inhibit pathological vagus nerve activity associated with the seizure that may be acting to slow the patient's heart rate. By providing such stimulation only when the patient experiences a seizure accompanied by a reduced heart rate (e.g., bradycardia), a therapy may be provided that acts to maintain the patient's heart rate when the patient experiences a seizure involving excessive vagal activity—and consequent undesired slowing of—the heart. In one embodiment, the blocking electrical signal (830) is provided to a right vagus nerve. Without being bound by theory, because the right vagus nerve innervates the right sinoatrial node that functions as the heart's natural pacemaker, it is believed that right-side VNS will have a more significant effect upon the heart rate than stimulation of the left vagus nerve. In alternative embodiments, the blocking signal may be applied to the left vagus nerve, to both the right and left vagus nerves, or to one or both of the left and right cardiac branches of the vagus nerves.

In one embodiment, the method comprises applying a first electrical signal that may be a conventional vagus nerve stimulation signal defined by a plurality of parameters (e.g., a pulse width, a current magnitude, a pulse frequency, an on-time and an off-time). A seizure detection algorithm (e.g., using one or more of a cardiac, kinetic, metabolic, EEG, or other body signal) may be used to detect seizures, and the patient's heart rate may be determined proximate the seizure detection to determine if the seizure is accompanied by a decrease in the patient's heart rate. If the seizure is accompanied by a slowing of the patient's heart rate, the first electrical signal may be suspended, and a second electrical signal may be applied to slow the patient's heart rate. The method may further include sensing the patient's heart rate during or after application of the second electrical signal. In one embodiment, the second electrical signal may be modified (e.g., by changing current magnitude, pulse width, or pulse frequency), or suspended (and possibly resumed) to maintain the patient's heart rate between an upper heart rate threshold and a lower heart rate threshold. In some embodiments, the upper and lower heart rate thresholds may be dynamically set (e.g., as no more than 5 bpm above or below the baseline HR prior to the seizure detection).

Figure 9:
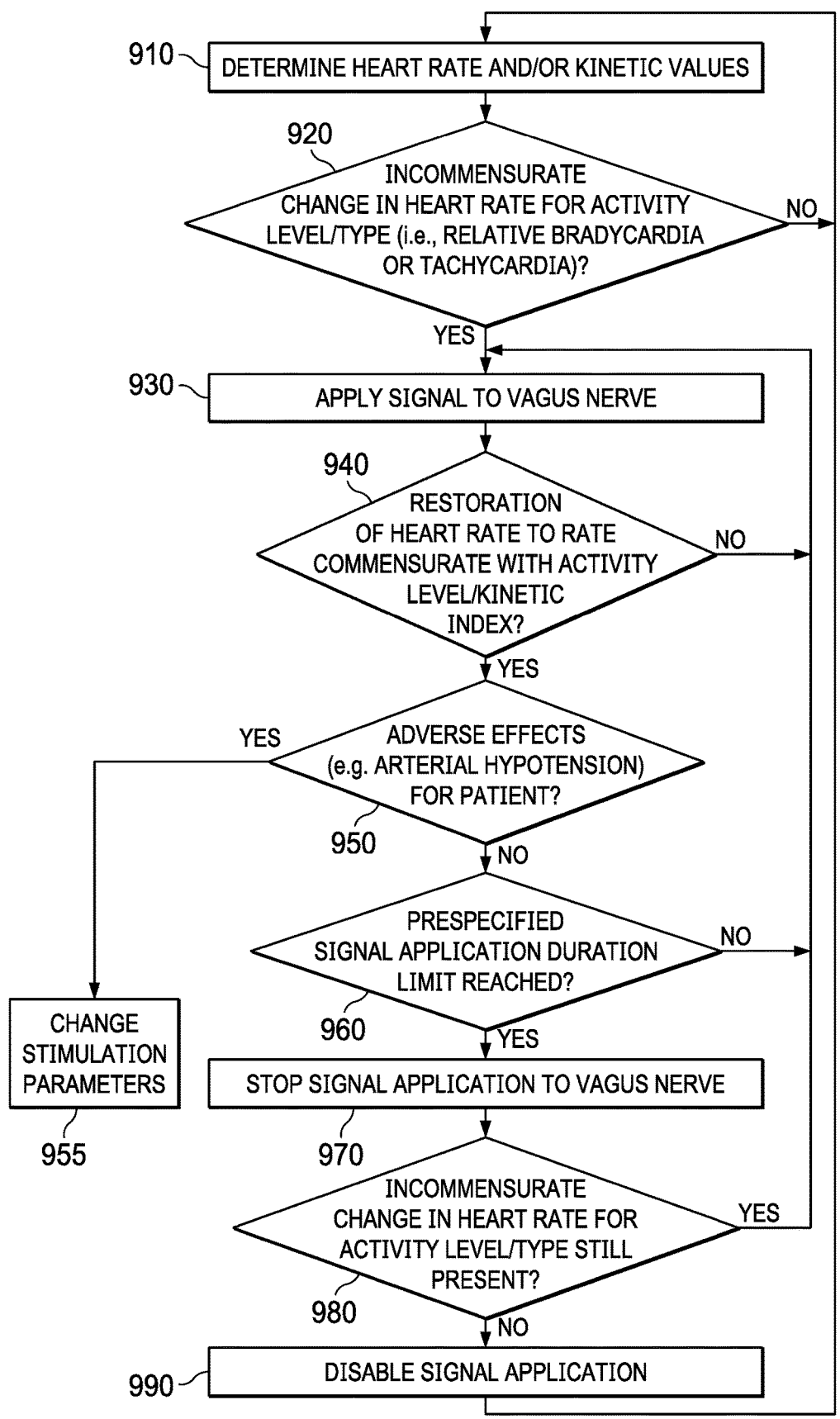
FIG. 9 is a flowchart depicting a method for providing closed-loop vagus nerve stimulation based on an assessment of whether the patient's heart rate is commensurate with the patient's activity level or activity type.

FIG. 9 is a flow diagram of a method of treating a patient with epilepsy by providing closed-loop vagus nerve intervention (e.g., stimulation or blockage of impulse conduction) to maintain the patient's heart rate within a range that is both safe and also commensurate with the activity type or level and state of the patient (e.g., as determined from a kinetic signal from a sensing element such as a triaxial accelerometer or by measuring oxygen consumption). In one embodiment, the method comprises providing vagus nerve stimulation in response to determining that a heart rate is incommensurate with the kinetic signal of the patient, to restore cardiac function to a rate that is commensurate with the patient's kinetic signal. In one embodiment, the stimulation may comprise stimulating a right vagus nerve to slow the patient's heart rate to a level that is safe and/or commensurate with activity level. In another embodiment, the stimulation may comprise providing a blocking signal to increase a slow heart rate to a rate that is safe and/or commensurate with the activity level. Pharmacologic compounds (e.g., drugs) with sympathetic or parasympathetic effects (e.g., enhancing or blocking sympathetic or parasympathetic activity) may be used to restore heart rate to a rate commensurate with kinetic activity of the patient in still other embodiments. In one embodiment, the method involves determining a heart rate and one or more kinetic or metabolic (e.g., oxygen consumption) indices for the patient (910). Heart rate may be determined from an acquired cardiac signal (e.g., from a sensor or stored data). Kinetic and/or metabolic indices may likewise be determined from a kinetic sensor (e.g., an accelerometer, a positional sensor, a GPS device coupled to a clock, or a postural sensor), a metabolic sensor, or from stored data. Sensor data may be subjected to one or more operations such as amplifying, filtering, A/D conversion, and/or other pre-processing and processing operations to enable determination of heart rate (and in some embodiments other cardiac indices such as heart rate variability) and kinetic indices.

The activity level of the patient may be determined from multiple kinetic indications such as an activity level, a type of activity, a posture, a body position, a trunk or limb acceleration or force, or a duration of one of the foregoing, and may be adapted or modified as a function of age, gender, body mass index, fitness level or time of day or other indices of the patient's condition or environment. For example, the kinetic signal may be processed to provide indices that indicate moderate ambulatory motion for an upright patient, vigorous physical exercise (in which the patient may be upright as in running or in a prone position as in some calisthenics exercises), a fall (e.g., associated with a seizure), reclining, resting or sleeping, among other activity levels and kinetic states.

The one or more kinetic indices may then be used to determine (e.g., by retrieving stored data from a lookup table or by calculation using an algorithm) one or more heart rate ranges or values that would be commensurate with the kinetic activity and/or kinetic state, duration, time of day, etc. associated with the indices. In some embodiments, heart rate ranges may be established for particular levels or types of activity (e.g., running, walking), that may be adaptively adjusted depending upon various factors such as the duration of the activity, the patient's fitness level, the time of day, a level of fatigue, an environmental temperature, etc. A commensurate heart rate is one that is within expected ranges or values for the person's effort, and for factors inherent to the patient and the environment.

Returning to FIG. 9, the determined heart rate may be compared to the range(s)/value(s) identified as commensurate with the kinetic indices (920) at a given time point. If the actual heart rate of the patient is within the expected/ commensurate range or value associated with the kinetic or metabolic indices at the time point, or is within a specified proximity of a particular range or value, no action may be taken, and the method may involve continuing to analyze the patient's cardiac and kinetic signals or metabolic signals. On the other hand, if the heart rate is outside the expected value or range of values for the kinetic or metabolic indices for that time point, then the heart rate is not commensurate with the kinetic signal of the patient, and a therapy may be provided to the patient by applying one of an electrical, thermal, mechanical or chemical signal to a vagus nerve of the patient (930) or administering to the patient (e.g., intravenously, through mucosae) a drug with cholinergic or anti-cholinergic or adrenergic actions, depending on the case or situation. In one embodiment, the method may comprise applying the signal to a main trunk of a vagus nerve of the patient, and in another embodiment, the signal may be applied to a cardiac branch of a vagus nerve.

In one embodiment, the heart rate of the patient may be higher than a value commensurate with the activity level or kinetic indices of the patient. In this case, the patient is having relative tachycardia. Where this is the case, as previously noted, vagus nerve stimulation may be applied to one or more of a right cardiac branch, left cardiac branch, or right main trunk of the patient's vagus nerve to reduce the patient's heart rate to a rate that is commensurate with the activity level. Embodiments of the disclosure may be used to treat epileptic seizures associated with tachycardia, and other medical conditions associated with tachycardia given the patient's activity level. Therapies (e.g., electrical, chemical, mechanical, thermal) delivered to a patient via the vagus nerves may be employed for tachyarrythmias, angina pectoris or pain in regions innervated by a vagus nerve.

In another embodiment, the patient's heart rate may be lower than a value commensurate with the patient's activity level or kinetic indices, that is, the patient is having relative or absolute bradycardia. High frequency (>>300 Hz) electrical pulses may be applied to the left or right vagus nerves (e.g., a main trunk of the right and/or left vagus nerves or to their cardiac branches) to block propagation of transmission of nerve impulses through their fibers. High-frequency VNS may be applied to block impulses traveling to the heart to abate neurogenic, cardiogenic or iatrogenic bradycardia, or to minimize the cumulative effects on the heart's conduction system and myocardium of epileptic seizures, especially in status epilepticus. Selective blockage of impulses traveling through a vagus nerve to the heart may be accomplished with electrical stimulation to treat adverse cardiac effects associated with disorders such as epilepsy, depression, diabetes or obesity. By blocking vagus nerve conduction to the heart, when the patient's heart rate is incommensurate with the activity level or kinetic indices, a therapy may be provided to revert the change in heart rate (whether the change involves bradycardia or tachycardia). In one embodiment, an electrical signal generator may be used to apply a first therapy signal to a vagus nerve of the patient, and an electrical signal generator (which may be the same or a different electrical signal generator) may apply a vagus nerve conduction blocking electrical signal to a vagus nerve (e.g., a cardiac branch of the vagus nerve) to block cardiac effects that would result from the first electrical signal, absent the vagus nerve conduction blocking electrical signal.

Referring again to FIG. 9, the method may comprise determining the patient's heart rate in response the therapy to determine whether the heart rate has been restored to a rate that is with commensurate with the patient's activity level/kinetic index (940). If not, then the therapy (e.g., VNS to reduce or increase heart rate to an appropriate value) may be continued, with or without parameter modification, or re-initiated after a delay period or confirmation period.

If the heart rate has returned to a range/value commensurate with the activity level of the patient, the method may, in some embodiments, further involve determining whether or not an adverse event has occurred (950). Adverse events may include, without limitation, side effects such as voice alteration, pain, difficulty breathing or other respiratory effects, adverse cardiac effects such as bradycardia (following a determination of relative tachycardia in step 920), tachycardia (following a determination of bradycardia in step 920), and alteration in blood pressure or gastro-intestinal activity.

If an adverse event has occurred, the method may involve changing one or more stimulation parameters to eliminate, reduce or ameliorate the adverse event (955). If no adverse event has occurred, the method may comprise continuing to apply a signal the vagus nerve until a predetermined signal application duration has been reached (960), at which time the signal application may be stopped (970). The method may further comprise determining, after the therapy has been stopped, if the patient's heart rate remains incommensurate with the patient's activity level or type (980), in which case the signal application may be resumed or other appropriate action may be taken (e.g., local or remote alarms or alerts, notification of caregivers/healthcare providers, etc.). If the heart rate has returned to a value that is commensurate or appropriate for the patient's activity level, the signal application may be discontinued (990).

Figure 10:
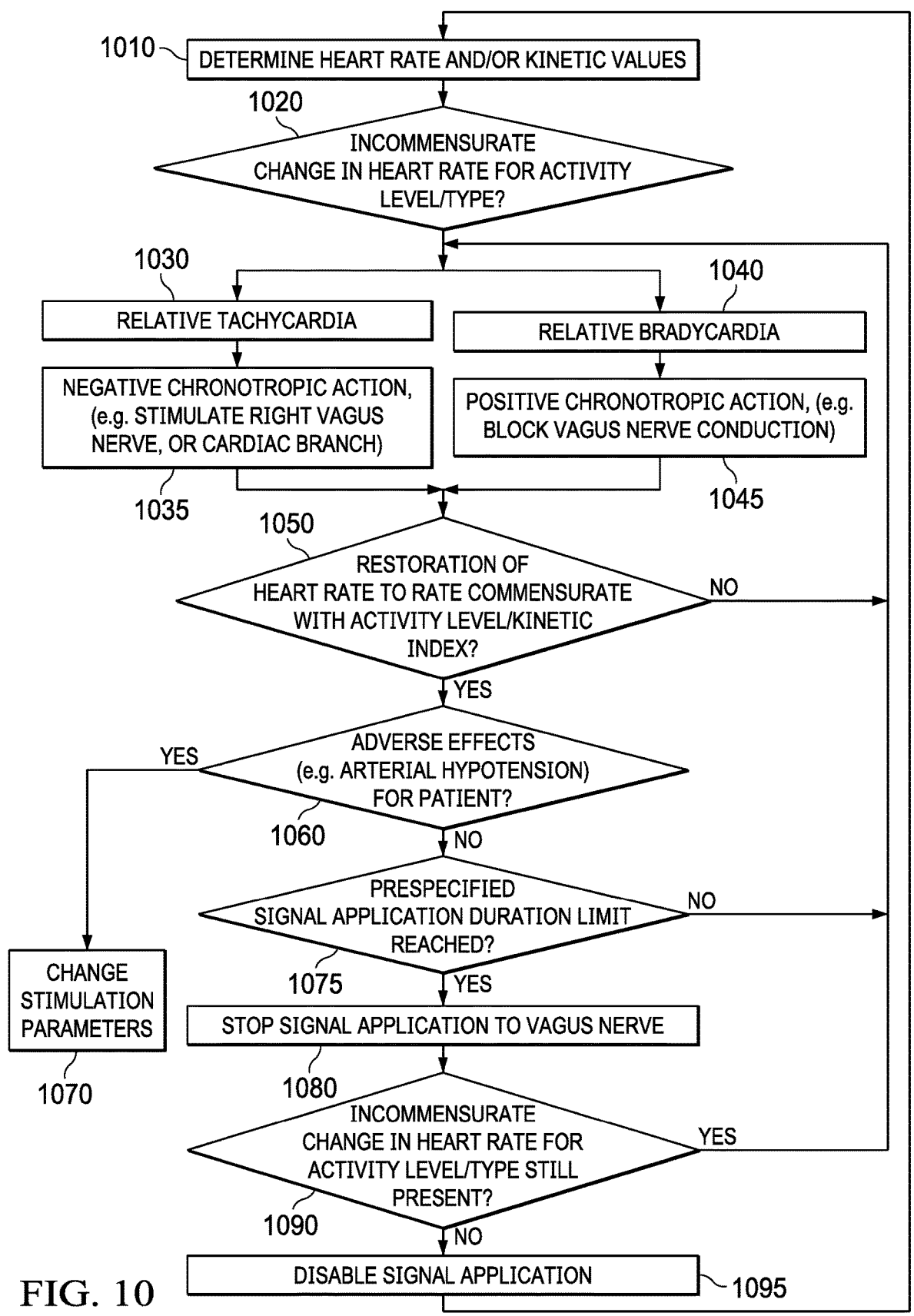
FIG. 10 is a flowchart depicting a method for providing closed-loop vagus nerve stimulation based on a determination that the patient's heart rate is incommensurate with the patient's activity level or activity type, and further in view of whether the incommensurate changes involves relative tachycardia or relative bradycardia.

FIG. 10 is a flow diagram of a method of treating a patient to with epilepsy by providing closed-loop vagus nerve stimulation to treat relative tachycardia or relative bradycardia by restoring the patient's heart rate to a rate that is commensurate with the activity type or level of the patient (e.g., as determined from a kinetic signal from a sensing element such as a triaxial accelerometer or by measuring oxygen consumption). In one embodiment, the method comprises identifying instances of relative tachycardia or relative bradycardia and responding with negative or positive chronotropic actions to restore the heart rate to a level commensurate with the patient's activity type or level.

In one embodiment, the method involves determining a heart rate and an activity type or level for the patient (1010). The patient's heart rate may be determined from an acquired cardiac signal or from stored data. The activity level or type of the patient may be determined from one or more sensor or from stored data. Sensors may include, for example, accelerometers, positional sensors, GPS devices coupled to a clock, postural sensors, and metabolic sensors. Sensor data may be subject to conventional signal processing, and may in addition be adapted or modified as a function of age, gender, body mass index, fitness level or time of day or other indices of the patient's condition or environment.

The patient's activity type or level may then be used to determine one or more heart rate ranges or values that are commensurate with the activity type or level (1020). In some embodiments, heart rate ranges may be established for particular levels or types of activity (e.g., running, walking), that may be adaptively adjusted depending upon various factors such as the duration of the activity, the patient's fitness level, the time of day, a level of fatigue, an environmental temperature, etc. A commensurate heart rate is one that is within expected ranges or values for the person's effort, and for factors inherent to the patient and the environment.

If the heart rate is commensurate with the activity level, in one embodiment no action may be taken, and the method may involve continuing to analyze the patient's cardiac and activity. On the other hand, if the heart rate is outside the identified value or range of values appropriate for the patient's activity type or level then the heart rate is not commensurate with the kinetic signal of the patient. Where this is the case, the method may further comprise determining whether the patient is experiencing relative tachycardia or is experiencing relative bradycardia (1030, 1040).

Where the heart rate of the patient is higher than a value commensurate with the activity level or type, the patient is experiencing relative tachycardia (1030), and the method may comprise initiating a negative chronotropic action (1035) to slow the heart rate to a rate that is commensurate with the activity level or type. In one embodiment, this may involve applying stimulation to one or more of a left or right main vagal trunk or cardiac branch of the patient. In other embodiments, the method may comprise providing a drug to enhance the parasympathetic tone of the patient. In still other embodiments, the method may comprise reducing the patient's sympathetic tone, such as by applying high-frequency stimulation to a sympathetic nerve trunk or ganglion or administering an anti-cholinergic drug. Negative chronotropic actions may be used to treat epileptic seizures associated with tachycardia, and other medical conditions associated with relative tachycardia given the patient's activity level.

Where the heart rate of the patient is lower than a value commensurate with the activity level or type, the patient is experiencing relative bradycardia (1040), and the method may comprise initiating a positive chronotropic action (1045) to increase the heart rate to a rate that is commensurate with the activity level or type. In one embodiment, this may involve applying high-frequency (>>300 Hz) electrical stimulation to one or more of a left or right main vagal trunk or cardiac branch of the patient to reduce the transmission of intrinsic vagus nerve action potentials in at least some vagal fibers. In other embodiments, the method may comprise providing a drug to reduce the parasympathetic tone of the patient. In still other embodiments, the method may comprise increasing the patient's sympathetic tone, such as by applying electrical signals to a sympathetic nerve trunk or ganglion or by administering a sympatho-mimetic drug. Positive chronotropic actions may be used to treat epileptic seizures associated with bradycardia, and other medical conditions associated with relative bradycardia given the patient's activity level.

The method may further comprise, after initiating the negative or positive chronotropic action, determining whether the patient's heart rate has been restored to a rate that is with commensurate with the patient's activity level/kinetic index (1050). If not, then the therapy (e.g., VNS to reduce or increase heart rate to an appropriate value) may be continued, with or without parameter modification, or re-initiated after a delay period or confirmation period.

If the heart rate has returned to a range/value commensurate with the activity level of the patient, the method may, in some embodiments, further involve determining whether or not an adverse event has occurred (1060). Adverse events may include, without limitation, side effects such as voice alteration, pain, difficulty breathing or other respiratory effects, adverse cardiac effects such as bradycardia (following a determination of relative tachycardia in step 1030), or tachycardia (following a determination of bradycardia in step 1040), and alteration in blood pressure or gastric activity.

If an adverse event has occurred, the method may involve changing one or more stimulation parameters to eliminate, reduce or ameliorate the adverse event (1070). If no adverse event has occurred, the method may comprise continuing to stimulate the vagus nerve (or a chemical, thermal or mechanical therapy) until a predetermined stimulation duration has been reached (1075), at which time the stimulation may be stopped (1080). The method may further comprise determining, after the therapy has been stopped, if the patient's heart rate remains incommensurate with the patient's activity level or type (1090), in which case the stimulation may be resumed or other appropriate action may be taken (e.g., local or remote alarms or alerts, notification of caregivers/healthcare providers, use of other forms of therapy, etc.). If the heart rate has returned to a value that is commensurate or appropriate for the patient's activity level, the stimulation may be discontinued (1095).

Additional embodiments consistent with the foregoing description and figures may be made. Non-limiting examples of some such embodiments are provided in the numbered paragraphs below.

100. A method of controlling a heart rate of an epilepsy patient comprising:
    sensing at least one of a kinetic signal and a metabolic signal of the patient;
    analyzing the at least one of a kinetic and a metabolic signal to determine at least one of a kinetic index and a metabolic index;
    receiving a cardiac signal of the patient;
    analyzing the cardiac signal to determine the patient's heart rate;
    determining if the patient's heart rate is commensurate with the at least one of a kinetic index and a metabolic index; and
    applying an electrical signal to a vagus nerve of the patient based on a determination that the patient's heart rate is not commensurate with the at least one of a kinetic signal and a metabolic signal of the patient.

101. The method of numbered paragraph 100, wherein determining at least one of a kinetic index and a metabolic index comprises determining at least one of an activity level or an activity type of the patient based on the at least one of a kinetic index and a metabolic index, and wherein determining if the patient's heart rate is commensurate with the at least one of a kinetic index and a metabolic index of the patient comprises determining if the heart rate is commensurate with the at least one of an activity level or an activity type.

102. The method of numbered paragraph 101, wherein determining if the patient's heart rate is commensurate with the at least one of a kinetic index and a metabolic index comprises determining if the patient's heart rate is above or below a rate that is commensurate with the one or more of a kinetic index and a metabolic index.

103. A method of treating a patient having epilepsy comprising
    sensing at least one body signal of the patient;
    determining whether or not the patient is having or has had an epileptic seizure based on the at least one body signal;
    sensing a cardiac signal of the patient;
    determining whether or not the seizure is associated with a change in the patient's cardiac signal;
    applying a first therapy to a vagus nerve of the patient based on a determination that the patient is having or has had an epileptic seizure that is not associated with a change in the patient's cardiac signal, wherein the first therapy is selected from an electrical, chemical, mechanical, or thermal signal; and
    applying a second therapy to a vagus nerve of the patient based on a determination that the patient is having or has had an epileptic seizure associated with a change in the patient's cardiac signal, wherein the second therapy is selected from an electrical, chemical, mechanical (e.g., pressure) or thermal signal.

104. The method of numbered paragraph 103, further comprising applying a third therapy to a vagus nerve of the patient based a determination that the patient is not having or has not had an epileptic seizure, wherein the third therapy is selected from an electrical, chemical, mechanical or thermal signal.

105. A method of treating a patient having epilepsy comprising:
    coupling a first set of electrodes to a main trunk of the left vagus nerve of the patient;
    coupling a second set of electrodes to a main trunk of the right vagus nerve of the patient;
    providing an electrical signal generator coupled to the first electrode set and the second electrode set;
    receiving at least one body data stream;
    analyzing the at least one body data stream using a seizure detection algorithm to determine whether or not the patient is having and/or has had an epileptic seizure;
    applying a first electrical signal from the electrical signal generator to the main trunk of the left vagus nerve, based on a determination that the patient is having and/or has had an epileptic seizure without a heart rate change; and
    applying a second electrical signal from the electrical signal generator to the main trunk of the right vagus nerve, based on a determination that the patient is having or has had an epileptic seizure with a heart rate change.

106. A method of treating a patient having epilepsy comprising:
    receiving at least one body data stream;
    analyzing the at least one body data stream using a seizure detection algorithm to detect whether or not the patient has had an epileptic seizure;
    receiving a cardiac signal of the patient;
    analyzing the cardiac signal to determine a first cardiac feature;
    applying a first electrical signal to a vagus nerve of the patient, based on a determination that the patient has not had an epileptic seizure characterized by a change in the first cardiac feature, wherein the first electrical signal is not a vagus nerve conduction blocking electrical signal; and
    applying a second electrical signal to a vagus nerve of the patient, based on a determination that the patient has had an epileptic seizure characterized by a change in the cardiac feature, wherein the second electrical signal is a pulsed electrical signal that blocks action potential conduction in the vagus nerve.

107. A method of treating a patient having epilepsy comprising:
    receiving at least one body data stream;
    analyzing the at least one body data stream using a seizure detection algorithm to detect whether or not the patient has had an epileptic seizure;
    receiving a cardiac signal of the patient;
    analyzing the cardiac signal to determine a first cardiac feature;
    applying a first electrical signal to a vagus nerve of the patient, based on a determination that the patient has not had an epileptic seizure characterized by a change in the first cardiac feature, wherein the first electrical signal is a pulsed electrical signal that blocks action potential conduction in the vagus nerve; and applying a second electrical signal to a vagus nerve of the patient, based on a determination that the patient has had an epileptic seizure characterized by a change in the cardiac feature, wherein the second electrical signal is not a vagus nerve conduction blocking electrical signal.

Figure 11:
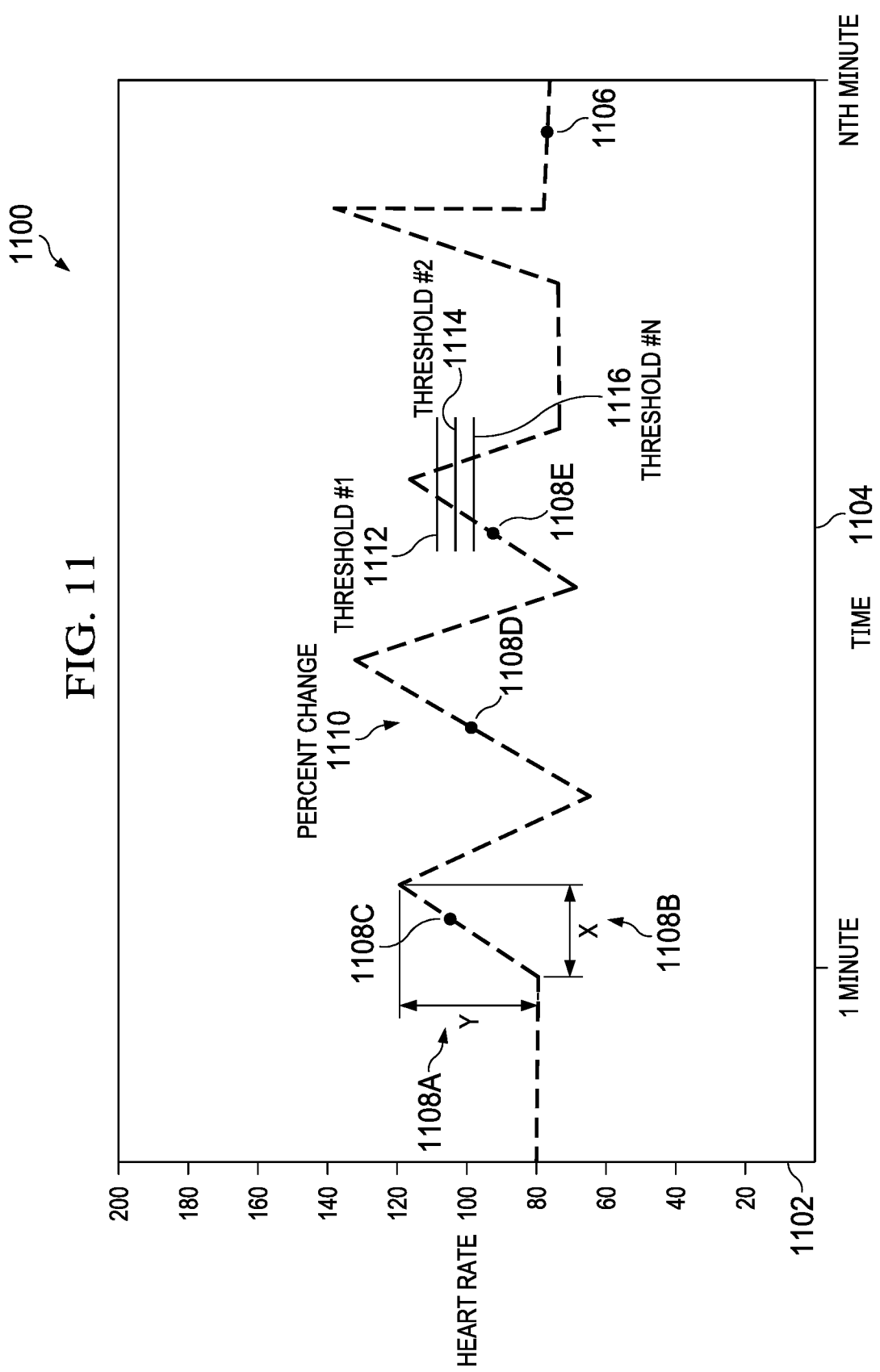
FIG. 11 is a graph of heart rate versus time, according to one embodiment.

In FIG. 11, a graph of heart rate versus time is shown, according to one embodiment. A first graph 1100 includes a y-axis 1102 which represents heart rate where the heart rate goes from a zero value to an Nth value (e.g., 200 heart beats, etc.). Further, the first graph 1100 includes an x-axis 1104 which represents time from 1 minute to Nth minutes (and/or 0.001 seconds to Nth seconds). In this example, a first heart rate versus time line 1106 for the patient is shown. In this example, the patient's heart rate goes from 80 heart beats per minute to 118 heart beats per minute with a first rise 1108A and a first run 1108B during a first event 1108C. In addition, the patient's heart rate goes from 70 heart beats per minute to 122 heart beats per minute during a second event 1108D which has a first percentage change 1110 associated with the second event 1108D. Further, the patient's heart rate goes from 70 beats per minute to 113 beats per minute during an nth event 1108E which surpasses a first threshold amount 1112, and/or a second threshold amount 1114, and/or an Nth threshold amount 1116. In one example, only the Nth threshold amount 1116 needs to be reached to trigger a therapy and/or an alert. In another example, only the second threshold amount 1114 needs to be reached to trigger a therapy and/or an alert. In another example, only the first threshold 1112 needs to be reached to trigger a therapy and/or an alert. In another example, both the Nth threshold 1116 and the second threshold 1114 need to reached to trigger a therapy and/or an alert. In another example, all of the Nth threshold 1116, the second threshold 1114 and the first threshold 1112 need to reached to trigger a therapy and/or an alert. In one example, only the Nth threshold amount 1116 needs to be reached during a specific time period to trigger a therapy and/or an alert. In another example, only the second threshold amount 1114 needs to be reached during a specific time period to trigger a therapy and/or an alert. In another example, only the first threshold 1112 needs to be reached during a specific time period to trigger a therapy and/or an alert. In another example, both the Nth threshold 1116 and the second threshold 1114 need to reached during a specific time period to trigger a therapy and/or an alert. In another example, all of the Nth threshold 1116, the second threshold 1114 and the first threshold 1112 need to reached during a specific time period to trigger a therapy and/or an alert. In these examples, one or more triggering events may occur based on a determination of the rise and run of a change in heart rate, a percentage change in heart rate, a threshold amount being reached or exceeded (or within any percentage of the threshold), and/or any combination thereof. A triggering event may initiate one or more actions to increase and/or decrease the patient's heart rate. For example, if the patient's heart rate is increasing which determines the triggering event, then the system, device, and/or method may initiate one or more actions to decrease the heart rate of the patient to help reduce, dampen, eliminate, and/or buffer the increase in the patient's heart rate. Further, the system, device, and/or method may oscillate between decreasing the patient's heart rate and increasing the patient's heart rate depending on any changes to the patient's heart rate. For example, the system, device, and/or method may initiate one or more actions to decrease a patient's heart rate based on the patient's heart rate going from 80 heart beats per minute to 130 heart beats per minute which results in the patient's heart rate falling from 130 heart beats per minute to 65 heart beats per minute in a first time period. Based on the change in the heart rate from 130 heart beats per minute to 65 heart beats per minute in the first time period, the system, device, and/or method may initiate one or more actions to increase the patient's heart rate and/or stabilize the patient's heart rate. In another example, the system, method, and/or device may stop and/or modify any initiated action based on one or more feedback signals. In addition, one or more warnings may be transmitted to the patient, a caregiver, a doctor, a medical professional, and/or logged.

Figure 12:
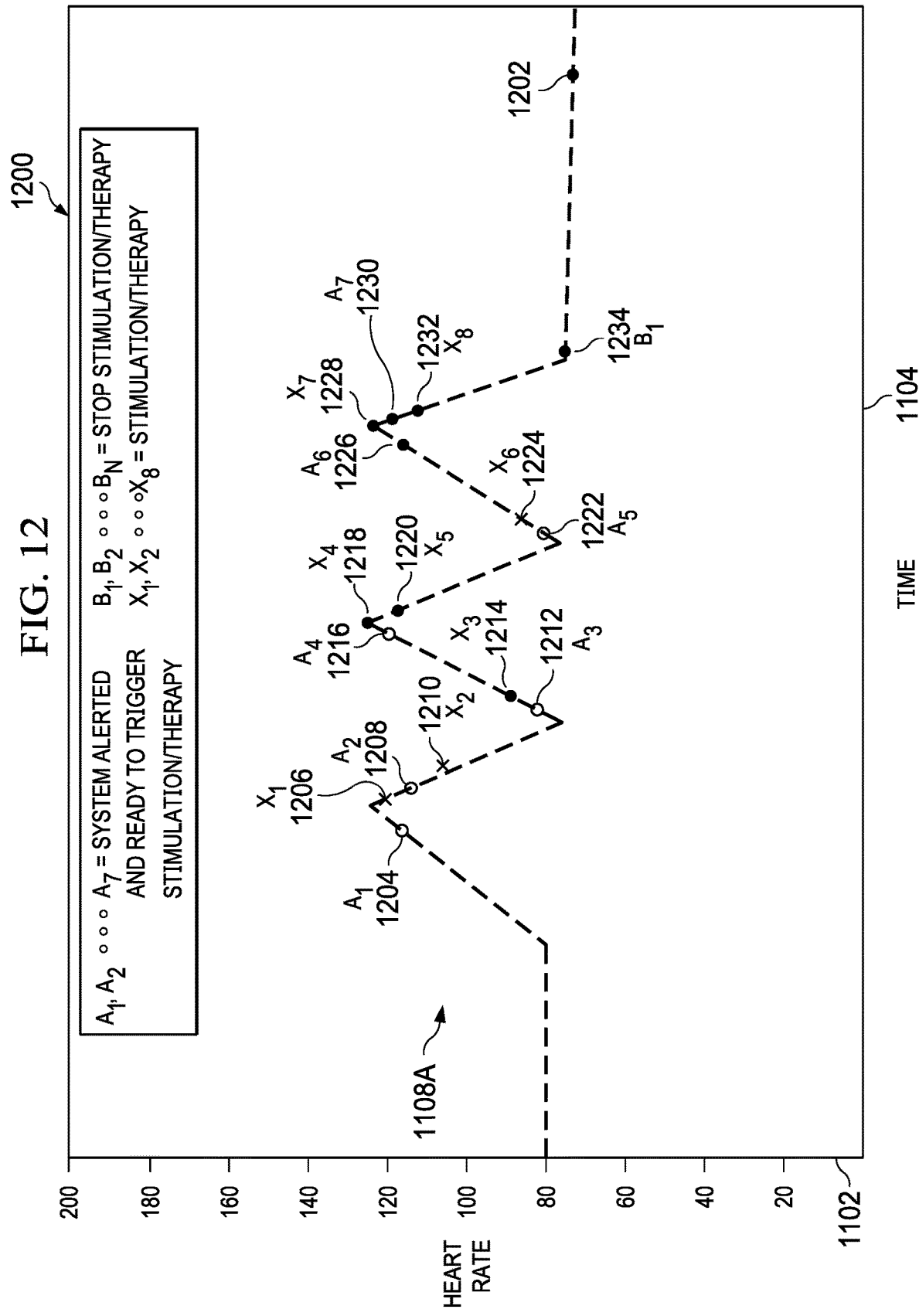
FIG. 12 is another graph of heart rate versus time, according to one embodiment.

In FIG. 12, another graph of heart rate versus time is shown, according to one embodiment. A second graph 1200 illustrating a second heart rate versus time line 1202 for the patient is shown. In this example, the patient's heart rate goes from 80 heart beats per minute to 120 heart beats per minute which creates a first system alert event 1204 (e.g., A1). Further, the system, device, and/or method initiates a first therapy 1206 (e.g., X1) based on the first system alert event 1204. In addition, a second system alert event 1208 (e.g., A2) occurs and a second therapy 1210 (e.g., X2) is initiated based on the second system alert event 1208. In addition, a third system alert event 1212 (e.g., A3) occurs and a third therapy (e.g., X3) 1214 is initiated based on the third system alert event 1212 (e.g., A3). In addition, a fourth system alert event 1216 (e.g., A4) occurs and a fourth therapy 1218 (e.g., X4) is initiated based on the fourth system alert event 1216 (e.g., A3). Further, a fifth therapy 1220 (e.g., X5) is initiated based on the effects of the fourth therapy 1218 (e.g., X4). In addition, a fifth system alert event 1222 (e.g., A5) occurs and a sixth therapy (e.g., X6) 1224 is initiated based on the fifth system alert event 1222 (e.g., A5). In addition, a sixth system alert event 1226 (e.g., A6) occurs and a seventh therapy (e.g., X7) 1228 is initiated based on the sixth system alert event 1226 (e.g., A6). In addition, a seventh system alert event 1230 (e.g., A7) occurs and an eighth therapy (e.g., X8) 1232 is initiated based on the seventh system alert event 1230 (e.g., A7). In addition, a first stop stimulation event 1234 (e.g., B1) occurs which turns off all therapies and/or system alerts may occur when the heart rate returns to the approximate starting heart rate and/or a target value. In these examples shown with FIG. 12, a rise over run heart rate calculation was completed to determine the one or more system alerts. However, it should be noted that any calculation (e.g., % increase, % decrease, etc. can be utilized). Further, all systems alerts and/or therapies may occur as independent events and/or examples. For example, the seventh system alert may be the first system alert in a specific example. In other words, no other events and/or therapies occurred before the seventh system alert. Therefore, the seventh system alert becomes the first system alert. In addition, one or more warnings may be transmitted to the patient, a caregiver, a doctor, a medical professional, and/or logged. In addition, there may be up to an Nth alerts, an Nth stop stimulation (and/or therapy) event, and an Nth therapy in any of the examples disclosed in this document.

Figure 13:
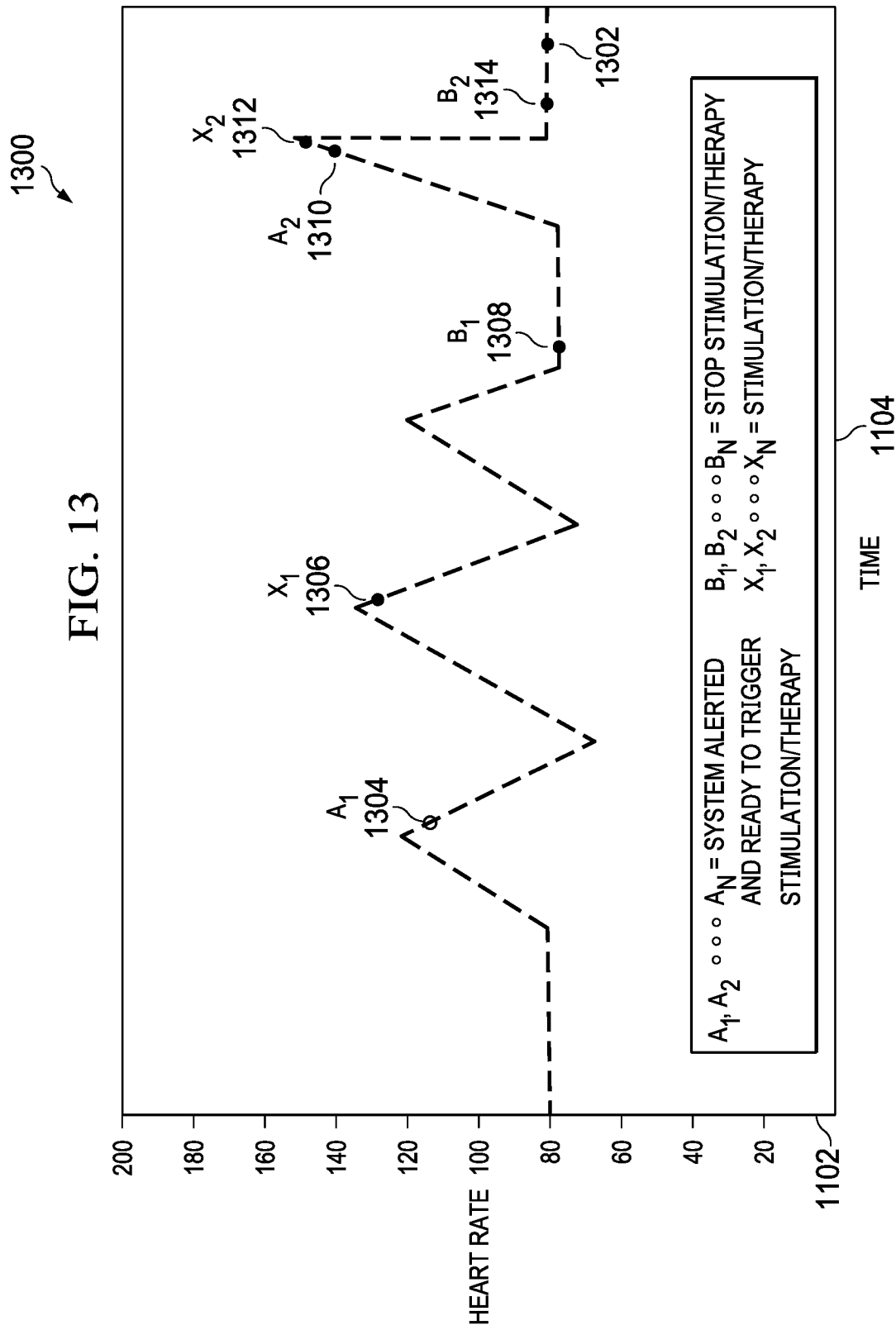
FIG. 13 is another graph of heart rate versus time, according to one embodiment.

In FIG. 13, another graph of heart rate versus time is shown, according to one embodiment. A third graph 1300 illustrating a third heart rate versus time line 1302 for the patient is shown. In this example, the patient's heart rate goes from 80 heart beats per minute to 116 heart beats per minute which creates a first system alert event 1304 (e.g., A1). Further, the system, device, and/or method initiates a first therapy 1306 (e.g., X1) based on the first system alert event 1304. In addition, a first stop stimulation event 1308 (e.g., B1) occurs which turns off all therapies and/or system alerts occurs when the heart rate returns to the approximate starting heart rate and/or a target value. Further, the patient's heart rate goes from 80 heart beats per minute to 123 heart beats per minute which creates a second system alert event 1310 (e.g., A2). Further, the system, device, and/or method initiates a second therapy 1312 (e.g., X2) based on the second system alert event 1310. In addition, a second stop stimulation event 1314 (e.g., B2) occurs which turns off all therapies and/or system alerts occurs when the heart rate returns to the approximate starting heart rate and/or a target value. In these examples shown with FIG. 13, a percentage change in heart rate calculation was completed to determine the one or more system alerts. However, it should be noted that any calculation (e.g., rise over run, etc. can be utilized). Further, all systems alerts and/or therapies may occur as independent events and/or examples. For example, the second system alert may be the first system alert in a specific example. In other words, no other events and/or therapies occurred before the second system alert. Therefore, the second system alert becomes the first system alert. In addition, one or more warnings may be transmitted to the patient, a caregiver, a doctor, a medical professional, and/or logged.

Figure 14:
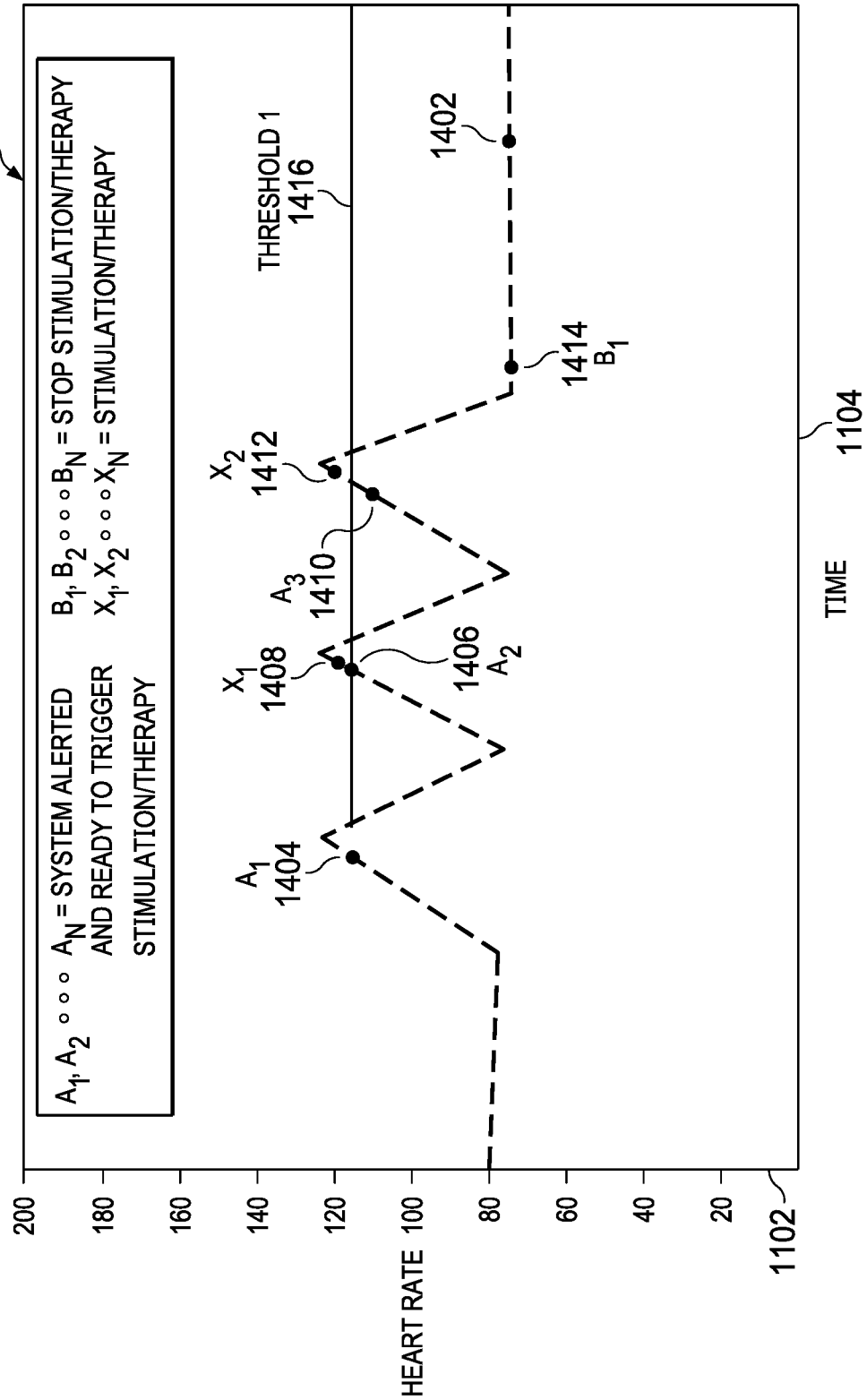
FIG. 14 is another graph of heart rate versus time, according to one embodiment.

In FIG. 14, another graph of heart rate versus time is shown, according to one embodiment. A fourth graph 1400 illustrating a fourth heart rate versus time line 1402 for the patient is shown. In this example, the patient's heart rate goes from 80 heart beats per minute to 120 heart beats per minute which creates a first system alert event 1404 (e.g., A1) because the 120 heart beats per minutes meets or exceeds a first threshold value 1416 (e.g., 115 heart beats per minute). In this example, a second system alert event 1406 (e.g., A2) is created because the heart beats of the patient meets or exceeds the first threshold value 1416 (e.g., 115 heart beats per minute). Further, the system, device, and/or method initiates a first therapy 1408 (e.g., X1) based on the first system alert event 1404 and the second system alert event 1406 occurring. The first system alert event 1404 and the second system alert event 1406 may be time dependent. For example, the first system alert event 1404 and the second system alert event 1406 may have to occur within a first time period for the initiation of the first therapy 1408. In another example, the first system alert event 1404 and the second system alert event 1406 may not be time dependent. Further, a third system alert event 1410 (e.g., A3) is created because the heart beats of the patient meets or exceeds (and/or within a specific rate of the threshold—in this example within 5 percent—heart rate is 110) the first threshold value 1416 (e.g., 115 heart beats per minute). Further, the system, device, and/or method initiates a second therapy 1412 (e.g., X2) based on the first system alert event 1404, the second system alert event 1406, and/or the third system event occurring. It should be noted that the second therapy 1412 has a time delay factor utilized with the second therapy 1412. In another example, no time delay is utilized. In addition, one or more time delays can be used with any therapy, any warning, and/or any alert in this document. The first system alert event 1404, the second system alert event 1406, and the third system alert event 1410 may be time dependent. For example, the first system alert event 1404, the second system alert event 1406, and the third system alert event 1410 may have to occur within a first time period for the initiation of the second therapy 1412. In another example, the first system alert event 1404, the second system alert event 1406, and the third system alert event 1410 may not be time dependent. Further, a first stop stimulation event 1414 (e.g., B1) occurs which turns off all therapies and/or system alerts occurs when the heart rate returns to the approximate starting heart rate and/or a target value. Further, all systems alerts and/or therapies may occur as independent events and/or examples. For example, the third system alert may be the first system alert in a specific example. In other words, no other events and/or therapies occurred before the third system alert. Therefore, the third system alert becomes the first system alert. In addition, one or more warnings may be transmitted to the patient, a caregiver, a doctor, a medical professional, and/or logged.

Figure 15:
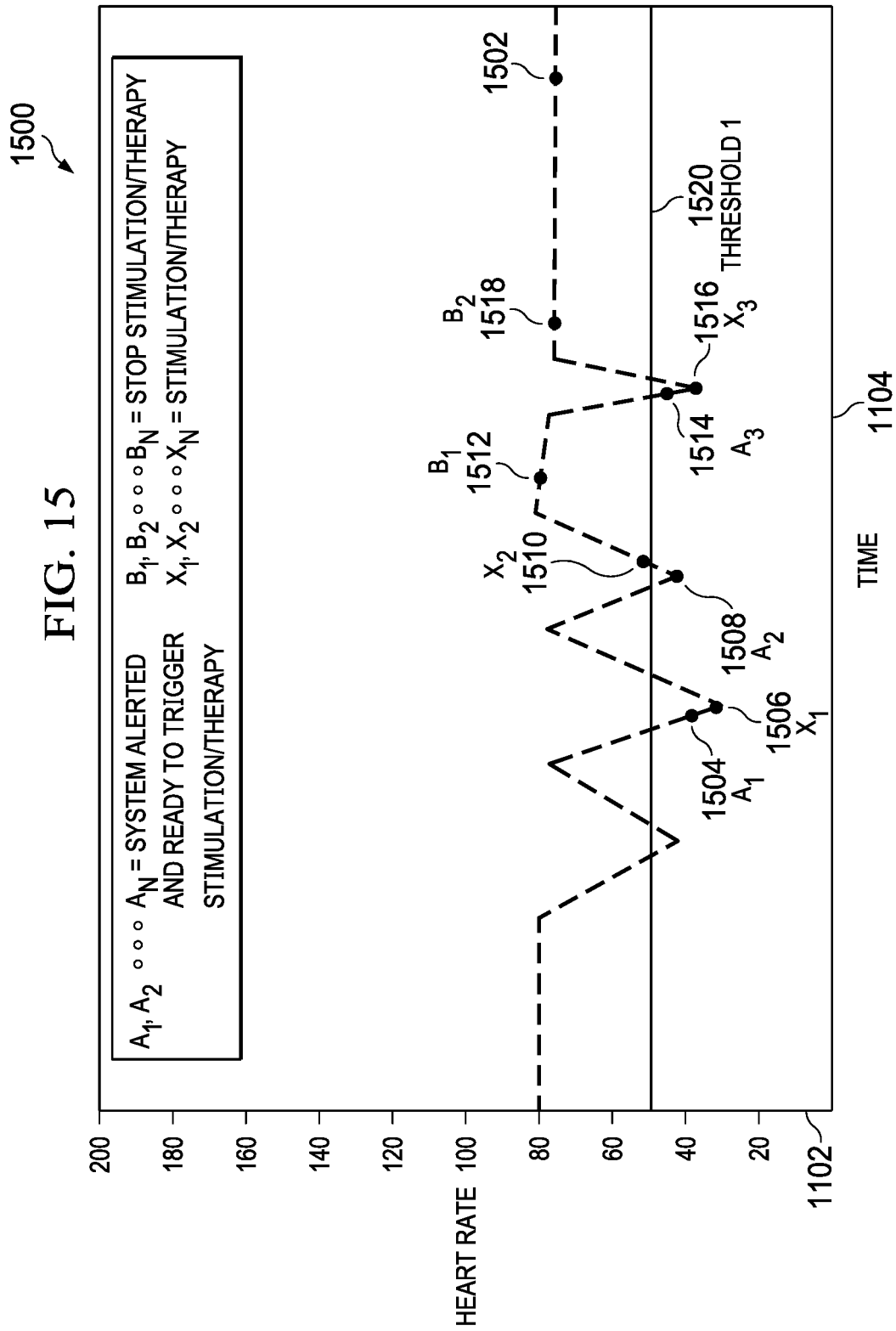
FIG. 15 is another graph of heart rate versus time, according to one embodiment.

In FIG. 15, another graph of heart rate versus time is shown, according to one embodiment. A fifth graph 1500 illustrating a fifth heart rate versus time line 1502 for the patient is shown. In this example, the patient's heart rate goes from 80 heart beats per minute to 40 heart beats per minute which creates a first system alert event 1504 (e.g., A1) because the 40 heart beats per minutes meets or exceeds a first threshold value 1520 (e.g., 50 heart beats per minute). It should be noted that no alert was generated when the heart rate fell to 52 heart beats per minute because 52 heart beats per minute is above the threshold value of 50 heart beats per minute. Further, the system, device, and/or method initiates a first therapy 1506 (e.g., X1) based on the first system alert event 1504 occurring. Further, the patient's heart rate goes from 80 heart beats per minute to 50 heart beats per minute which creates a second system alert event 1508 (e.g., A2) because the 50 heart beats per minutes meets or exceeds the first threshold value 1520 (e.g., 50 heart beats per minute). Further, the system, device, and/or method initiates a second therapy 1510 (e.g., X2) based on the second system alert event 1508 occurring. Further, a first stop stimulation event 1512 (e.g., B1) occurs which turns off all therapies and/or system alerts occurs when the heart rate returns to the approximate starting heart rate and/or a target value. In addition, the patient's heart rate goes from 80 heart beats per minute to 45 heart beats per minute which creates an nth system alert event 1514 (e.g., A3) because the 45 heart beats per minutes meets or exceeds the first threshold value 1520 (e.g., 50 heart beats per minute). Further, the system, device, and/or method initiates an Nth therapy 1516 (e.g., X3) based on the nth system alert event 1514 occurring. Further, an nth stop stimulation event 1518 (e.g., B2) occurs which turns off all therapies and/or system alerts occurs when the heart rate returns to the approximate starting heart rate and/or a target value. Further, all systems alerts and/or therapies may occur as independent events and/or examples. For example, nth system alert event 1514 alert may be the first system alert in a specific example. In other words, no other events and/or therapies occurred before nth system alert event 1514. Therefore, nth system alert event 1514 becomes the first system alert. In addition, one or more warnings may be transmitted to the patient, a caregiver, a doctor, a medical professional, and/or logged.

In regards to FIGS. 11-15 as related to this disclosure, the systems, devices, and/or methods may use a base line heart rate for the patient (e.g., a specific patient Bob, a general patient John Doe with a first health condition, a first age, etc.) over a first time period (e.g. one week, one month, one year, etc.), 50 percentile of all measured heart rates, an average of all heart rates, and/or any other method of determine a baseline heart rate. Further, the threshold level may be determined based on being the 40 percentile of the baseline, 39 percentile of the baseline, 38 percentile of the baseline, . . . , 10 percentile of the baseline, . . . , etc. In addition, the threshold level may be determined based on being the 75 percentile of the baseline, 76 percentile of the baseline, 77 percentile of the baseline, . . . , 90 percentile of the baseline, . . . , 99 percentile of the baseline, . . . , etc. In one example, the threshold value may be the 75 percentile of every recorded heart rate data. In another example, the oscillation does not matter whether the heart rate change is in an increasing direction or a decreasing direction. In various examples, the systems, devices, and/or method may reduce an amplitude of change (e.g., damping the change in heart rate) to enhance system performance and/or to reduce side effects. In addition, the determination of one or more side effects may initiate a reduction in therapy, a stoppage of therapy, a modification of therapy (e.g., changing a therapy that reduces heart rate to another therapy that increases heart rate), one or more warnings, and/or one or more logging of data.

Figure 16:
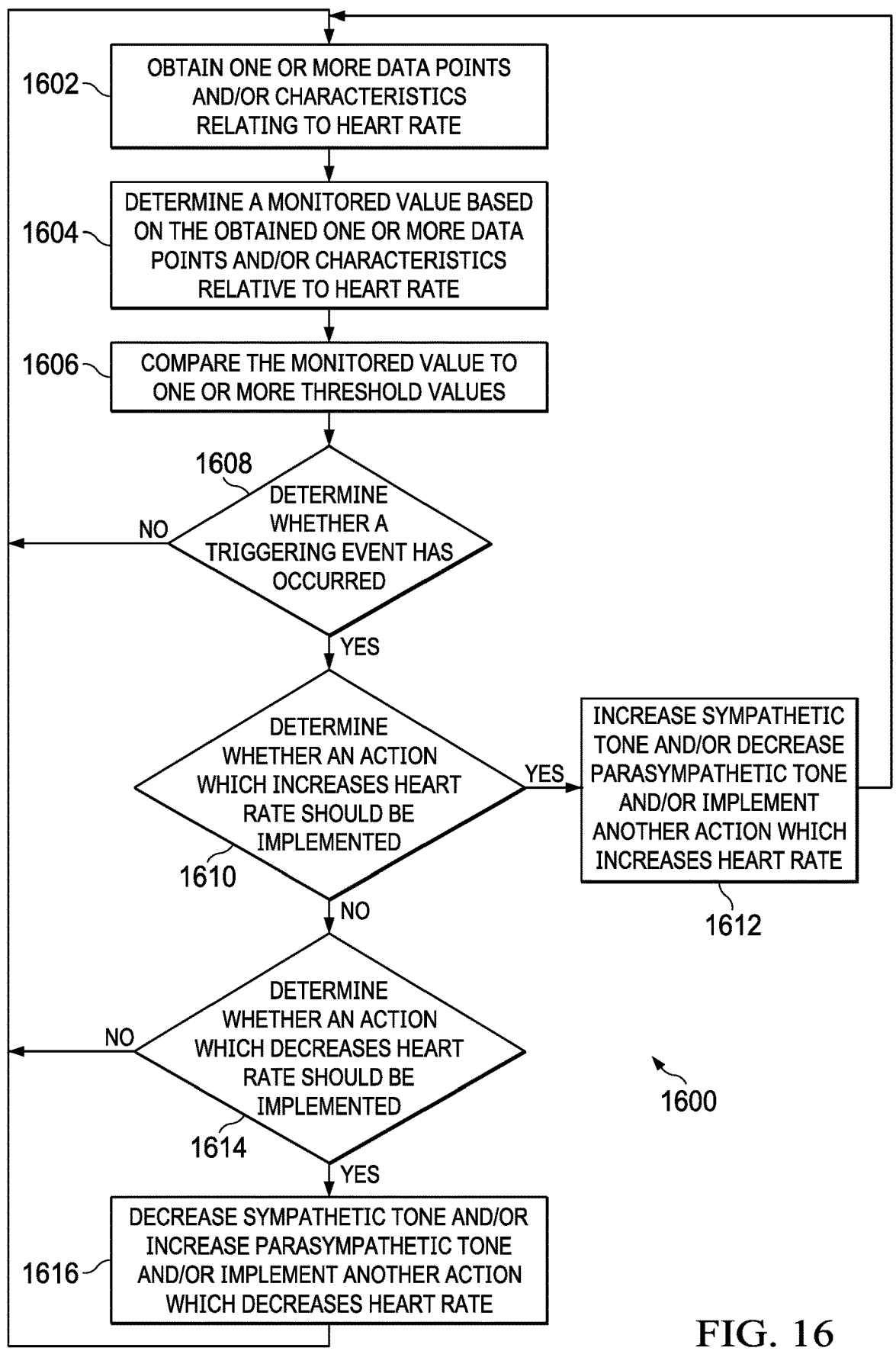
FIG. 16 is a flowchart of a therapy procedure, according to one embodiment.

In FIG. 16, a flowchart of a therapy procedure is shown, according to one embodiment. A method 1600 includes obtaining one or more data points and/or characteristics relating to heart rate of a patient (step 1602). The method 1600 may also include determining a monitored value based one the obtained one or more data points and/or characteristics relating to the heart rate (step 1604). The method 1600 may further compare the monitored value to one or more threshold values (step 1606). The method 1600 may via one or more processors (of a medical device(s) and/or medical device system) determine whether a triggering event has occurred (step 1608). If no triggering event has occurred, then the method 1600 moves back to step 1602. If a triggering event has occurred, then the method 1600 may determine via one or more processors (of a medical device(s) and/or medical device system) whether an action which increases heart rate should be implemented (step 1610). If an action which increases heart rate should be implemented, then the method 1600 may increase a sympathetic tone via one or more actions and/or decrease a parasympathetic tone via one or more actions and/or implement another action which increases heart rate (step 1612). After the implements of one or more actions, the method 1600 returns to step 1602. If an action which increases heart rate should not be implemented, then the method 1600 may determine via one or more processors (of a medical device(s) and/or medical device system) whether an action which decreases heart rate should be implemented (step 1614). If an action which decreases heart rate should be implemented, then the method 1600 may decrease a sympathetic tone via one or more actions and/or increase a parasympathetic tone via one or more actions and/or implement another action which decreases heart rate (step 1616). After the implements of one or more actions, the method 1600 returns to step 1602.

In one embodiment, a system for treating a medical condition in a patient includes: a sensor for sensing at least one body data stream; a heart rate unit capable of determining a heart rate of the patient based on the at least one body data stream; and a logic unit configured via one or more processors to compare a monitored value which is determined based on one or more data points relating to the heart rate to one or more threshold values, the logic unit further configured to determine a triggering event based on the comparison. Further, the one or more processors may initiate one or more actions to change the heart rate of the patient based on the determination of the triggering event.

In another example, the system includes at least one electrode coupled to a vagus nerve of the patient and a programmable electrical signal generator. In another example, the one or more processors may increase a sympathetic tone to increase the heart rate of the patient. In another example, the one or more processors may decrease a parasympathetic tone to increase the heart rate of the patient. In another example, the one or more processors may decrease a sympathetic tone to decrease the heart rate of the patient. In another example, the one or more processors may increase a parasympathetic tone to decrease the heart rate of the patient. In another example, the system includes a seizure detection unit which analyzes the at least one body data stream to determine an epileptic seizure status. In another example, the system includes at least one electrode coupled to a vagus nerve of the patient and a programmable electrical signal generator. Further, the one or more processors may apply an electrical signal to the vagus nerve of the patient based on a determination that a seizure is characterized by a decrease in the heart rate of the patient where the electrical signal is applied to block action potential conduction on the vagus nerve.

In another embodiment, a system for treating a medical condition in a patient, includes: a sensor for sensing at least one body data stream; at least one electrode coupled to a vagus nerve of the patient; a programmable electrical signal generator; a heart rate unit capable of determining a heart rate of the patient based on the at least one body data stream; and a logic unit configured via one or more processors to compare a monitored value which is determined based on one or more data points relating to the heart rate to one or more threshold values, the logic unit further configured to determine a triggering event based on the comparison. Further, the one or more processors may initiate one or more actions to change the heart rate of the patient based on the determination of the triggering event.

In another example, the one or more processors may increase a sympathetic tone to increase the heart rate of the patient based on a first triggering event. Further, the one or more processors may decrease a sympathetic tone to decrease the heart rate of the patient based on a second triggering event. Further, the one or more processors may decrease a parasympathetic tone to increase the heart rate of the patient based on a third triggering event. Further, the one or more processors may increase a parasympathetic tone to decrease the heart rate of the patient based on a fourth triggering event.

In another example, the one or more processors may increase the sympathetic tone to increase the heart rate of the patient based on a second triggering event. Further, the one or more processors may increase the sympathetic tone to increase the heart rate of the patient based on a third triggering event. Further, the one or more processors increase the sympathetic tone to increase the heart rate of the patient based on an nth triggering event.

In another example, the one or more processors decrease a sympathetic tone to decrease the heart rate of the patient based on a first triggering event. Further, the one or more processors decrease the sympathetic tone to decrease the heart rate of the patient based on a second triggering event. Further, the one or more processors may decrease the sympathetic tone to decrease the heart rate of the patient based on a third triggering event. In addition, the one or more processors decrease the sympathetic tone to decrease the heart rate of the patient based on an nth triggering event.

Cardio-protection in epilepsy is a rapidly growing field of vital importance. In this disclosure, systems, devices, and/or method of protecting the heart from standstill or fatal arhythmias are disclosed. Further in this disclosure, systems, devices, and/or methods of automated detections, warnings, reportings, treatments, controls and/or any combination thereof of ictal and peri-ictal chronotropic instability are shown.

Figure 17:
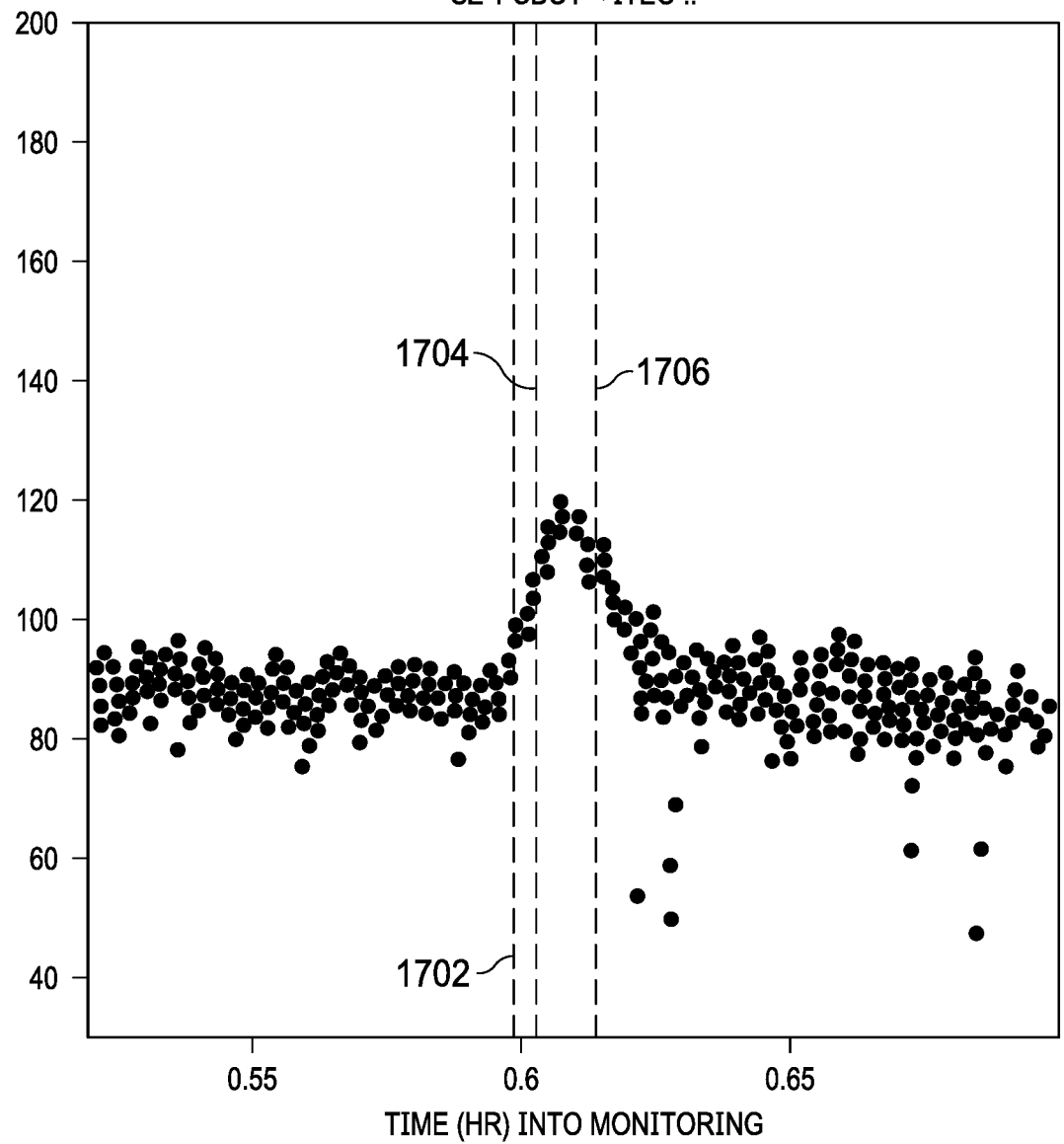
FIG. 17 is a graph relating to the automated detection and control of ictal and peri-ictal chronotropic instability, according to one embodiment.
Figure 18:
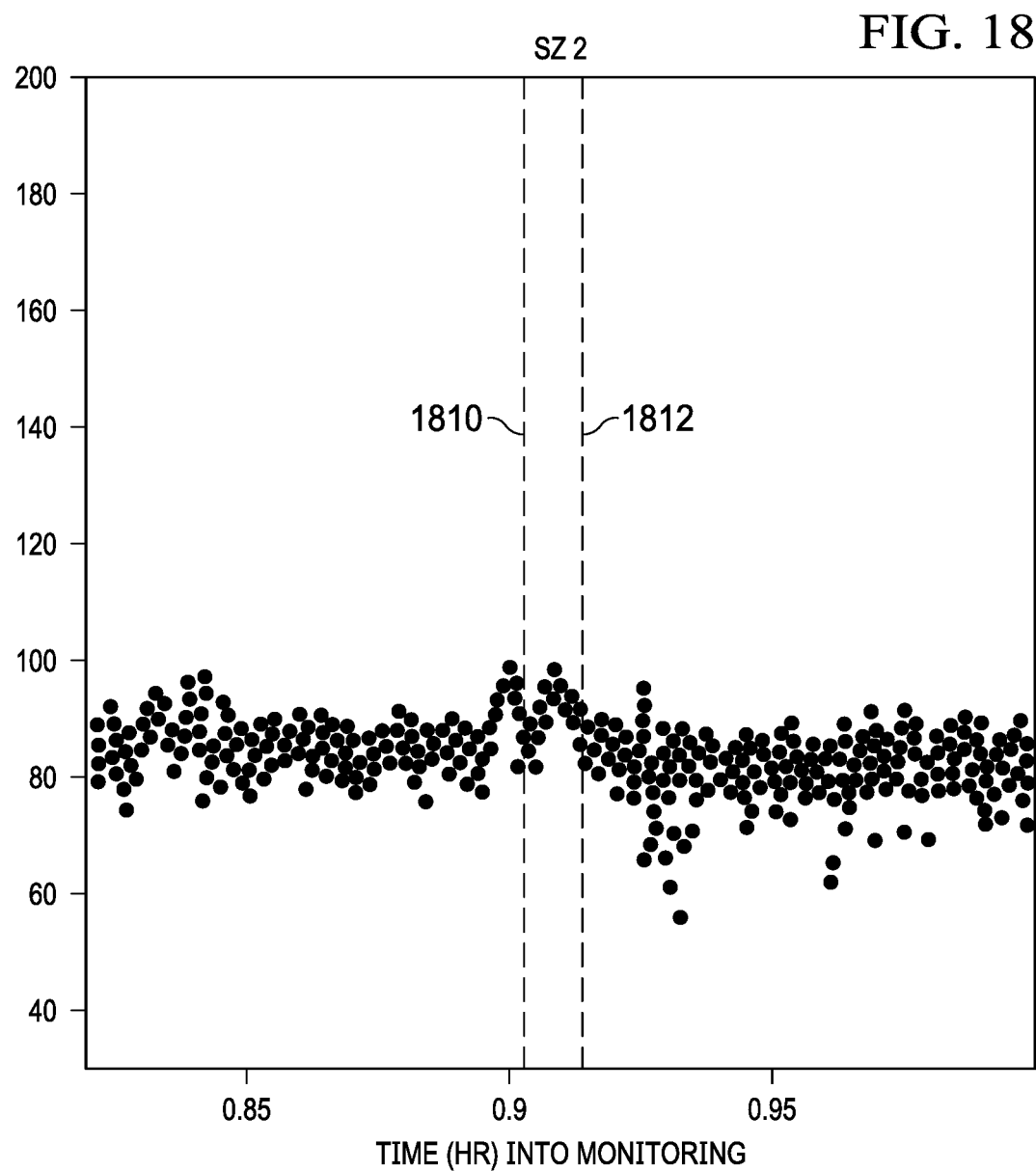
FIG. 18 is a graph relating to the automated detection and control of ictal and peri-ictal chronotropic instability, according to one embodiment.

In FIG. 17, a graph shows monotonic increase and decrease in heart rate. In FIG. 17, a first triggering event, a first warning event, and/or a first therapy event 1702 are shown. Further, a second triggering event 1704, a second warning event, and/or a second therapy event 1704 are shown. In addition, an Nth triggering event, an Nth warning event, and/or an Nth therapy event 1706 are shown. In FIG. 18, the heart rate of the patient increases which is followed by a decrease in heart rate, then an increase heart rate and a final decrease in heart rate. In this example, the first drop in heart rate crossed downwardly the detection threshold which would have temporarily disabled the warning system and the delivery of the therapy. While the first peak was not temporally correlated with paroxysmal activity on any of the intra-cranial electrodes used in this patient, it is likely that the first increase in heart rate was caused by epileptic discharges from a brain site that was not being investigated. In this example, the x-axis is time in hours and the y-axis is heart beats per minute. In this example, an electrographic onset in the brain 1810 is shown and an electrographic termination in the brain 1812 is shown.

Figure 19:
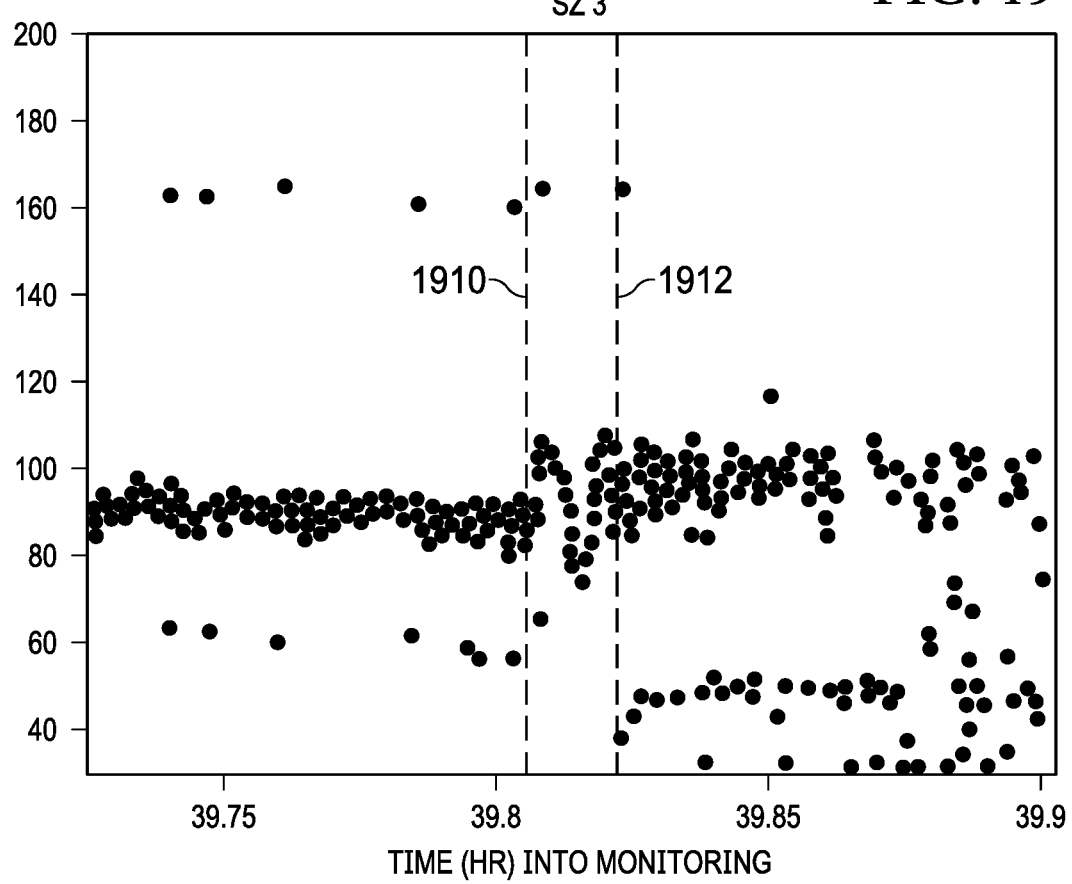
FIG. 19 is a graph relating to the automated detection and control of ictal and peri-ictal chronotropic instability, according to one embodiment.

In FIG. 19, a change in ictal heart rate is shown. In this example, the drop in heart rate during the seizure, is even more prominent that the one depicted in FIGS. 17-18, as it is below the inter-ictal baseline. It should be noted that the oscillations in heart rate during the post-ictal period are indicative of cardiac instability. In this example, a seizure onset point 1910 and a seizure termination point 1912 are shown.

Figure 20:
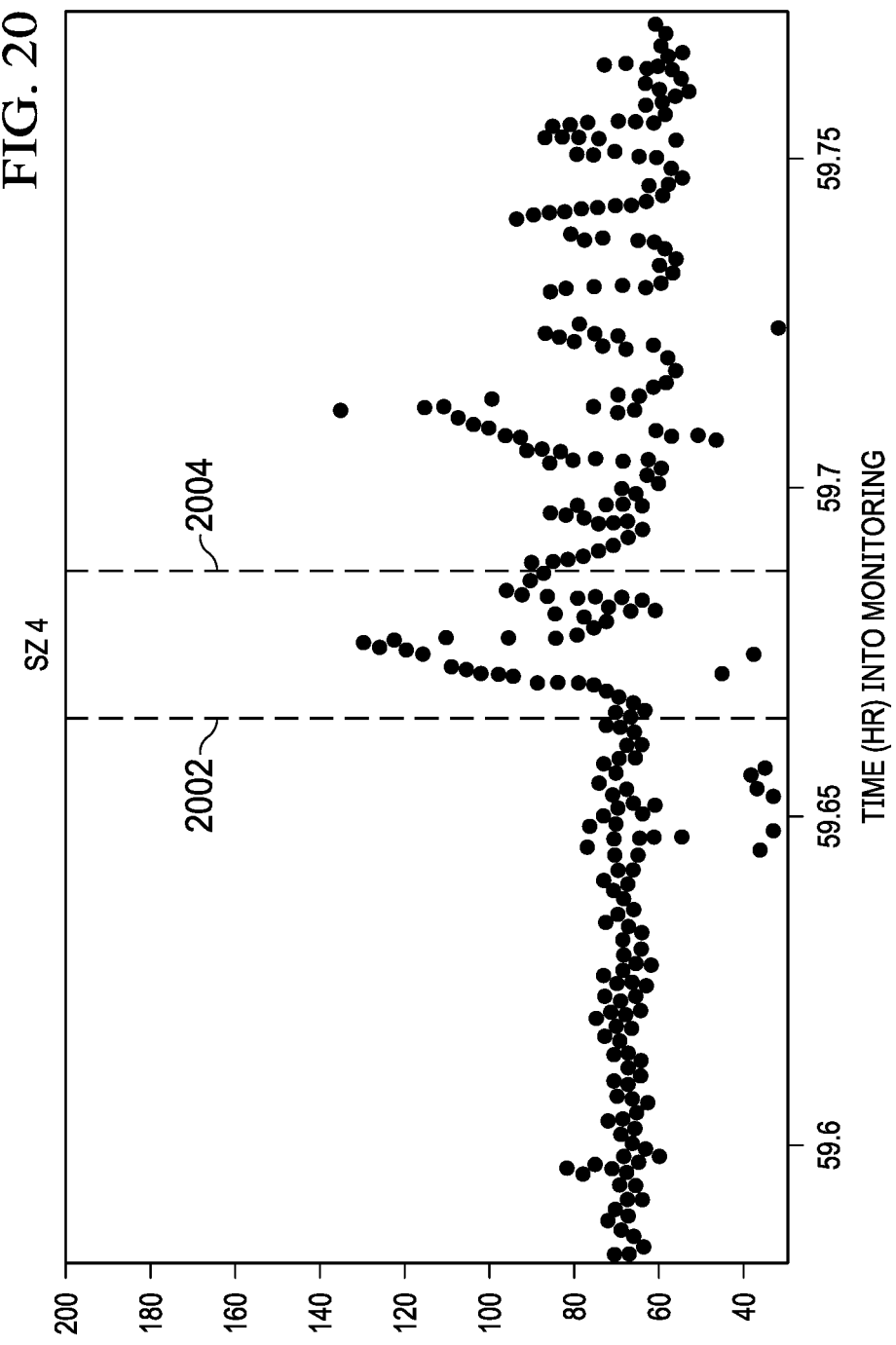
FIG. 20 is a graph relating to the automated detection and control of ictal and peri-ictal chronotropic instability, according to one embodiment.

In FIG. 20, large amplitude tachycardia cycles occurring quasi-periodically after termination of paroxysmal activity recorded with intra-cranial electrodes. While the mechanisms responsible for these oscillations are unknown, the probability that they are epileptic in nature cannot be excluded, since electrographic and imaging data used to guide intra-cranial electrode placement pointed to the existence of only one epileptogenic site.

Figure 21:
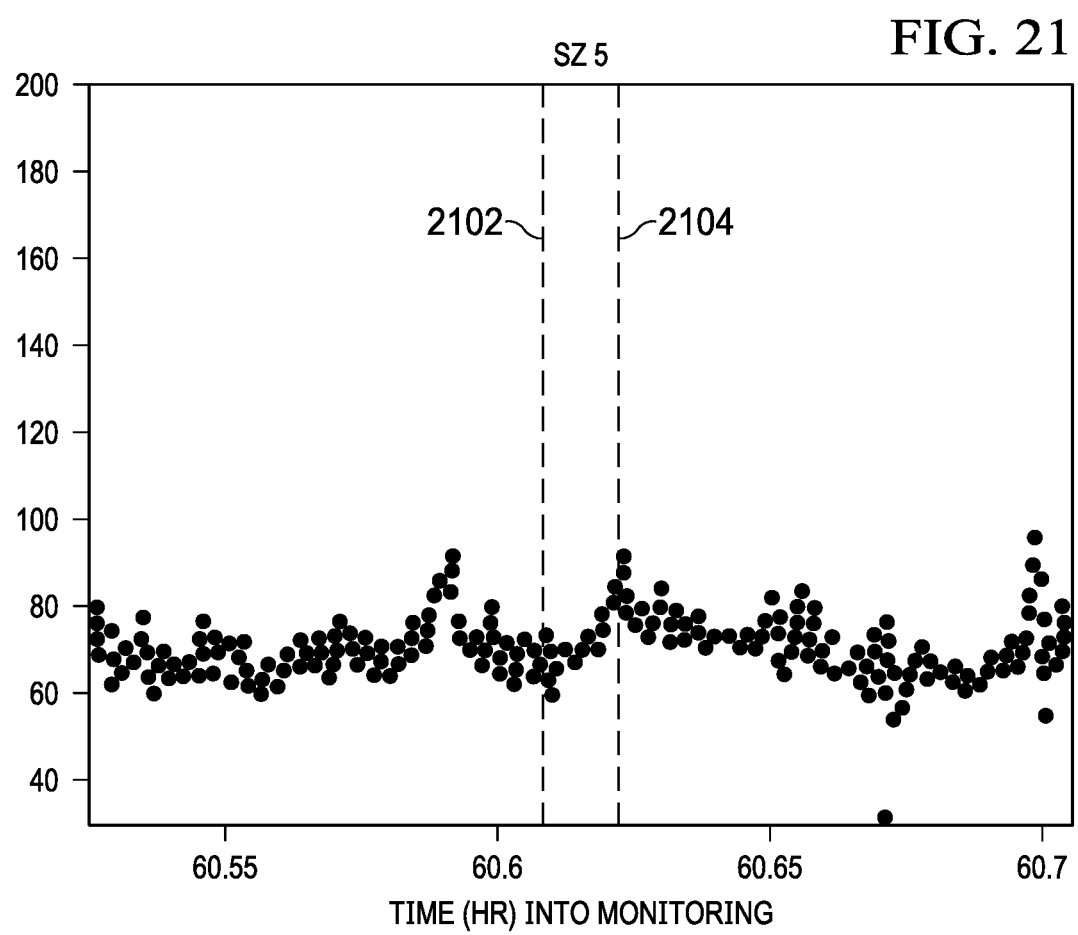
FIG. 21 is a graph relating to the automated detection and control of ictal and peri-ictal chronotropic instability, according to one embodiment.

In FIG. 21, small amplitude continuous quasi-periodic oscillations preceding and following a seizure recorded with intra-cranial electrodes (same patient as FIG. 20). In various embodiments, ictal and peri-ictal cardiac instability are shown. The mechanisms leading to SUDEP have not been elucidated, in part due to the inability to record data during the critical events that culminate in cardiac fibrillation or in standstill (or in respiratory arrest). In this example, a first triggering event, a first warning event, and/or a first therapy event 2102 are shown. Further, an Nth triggering event, an Nth warning event, and/or an Nth therapy event 2104 are shown.

The data obtained in intractable epileptics undergoing epilepsy surgery evaluation not only supports a cardiac mechanism (of course, not at the exclusion of catastrophic respiratory failure) but more specifically points to chronotropic instability as backdrop against which, lethal arrhythmias or cardiac standstill may ensue. Moreover, the instability is not restricted to the ictal period but, in certain cases, precedes and/or follows it for several minutes. FIGS. 17-21 illustrate the spectrum of instability in intractable epileptics. This phenomenon is referred herein to as Ictal and Pre-Ictal Chronotropic Instability.

The challenges that for accurate quantification and delivery of efficacious therapies, ictal chronotropic instability poses, were addressed and strategies to manage them are outlined. Here, the attention is focused on Ictal and Pre-Ictal Chronotropic Instability, a more prolonged and serious pathological phenomenon in intractable epileptics and on the vital issues of cardio-protection.

The aim of this disclosure is to contingently and adaptively dampen based on the slope, amplitude, duration and "direction" (positive or negative chronotropic and its magnitude relative to an adaptive baseline/reference heart rate) the heart oscillations present before, during or after epileptic seizures.

While several embodiments may be envisioned, on embodiment (for efficacy, practicality and cost-effectiveness) is to electrically stimulate/activate the trunk or a branch of the right vagus nerve in the case of elevations in heart (to reduce the heart rate, when there are more than 2 consecutive oscillations/cycles or 1 that is large and prolonged. The intensity and duration of stimulation as well as other parameters are determined by the slope, amplitude and duration of the oscillations, while ensuring adequate blood perfusion to all organs. In the case of negative chronotropic effects (decreases in heart rate) the trunk or a branch of the right vagus nerve may be "blocked" using certain electrical stimulation techniques or through cooling; the effect of this intervention is to increase heart rate.

In one embodiment, the "height" of the oscillation is the only feature considered. While obviously important, this embodiment does not take into consideration a possibly more important feature: the rate at which the oscillation occurs: the consequences of waiting to intervene until an oscillation reaches a certain height (e.g., 120 bpm) are different if it takes, 30 seconds for the heart rate to reach the value than if it takes 2 seconds to reach the value. Estimating the rate of change of the heart rate, provides life-saving information. Another aspect is the inter-maxima or inter-minima interval between oscillations. Having heart rate oscillation occur every 2-3 seconds is much more serious than every 1-2 hours. In one example, one benefit may be that the window to act is lengthen which can save lives. In one embodiment, a system for treating a medical condition in a patient includes: a sensor for sensing at least one body data stream; a heart rate unit which determines a heart rate and a heart rate oscillation of the patient based on the at least one body data stream; and a logic unit which compares via one or more processors a monitored value which is determined based on one or more data points relating to the heart rate and to the heart rate oscillation to a threshold value, the logic unit determines a triggering event based on the comparison where the one or more processors initiate one or more actions to change the heart rate of the patient based on the determination of the triggering event.

In another example, the system includes at least one electrode coupled to a vagus nerve of the patient and a programmable electrical signal generator. Further, the one or more processors may increase a sympathetic tone to increase the heart rate of the patient. In another example, the one or more processors may decrease a parasympathetic tone to increase the heart rate of the patient. In another example, the one or more processors may decrease a sympathetic tone to decrease the heart rate of the patient. Further, the one or more processors may increase a parasympathetic tone to decrease the heart rate of the patient. In addition, the system may include a seizure detection unit which analyzes the at least one body data stream to determine an epileptic seizure status. The system may include at least one electrode coupled to a vagus nerve of the patient and a programmable electrical signal generator where the one or more processors apply an electrical signal to the vagus nerve of the patient based on a determination that a seizure is characterized by a decrease in the heart rate of the patient and where the electrical signal is applied to block action potential conduction on the vagus nerve. In addition, the heart unit may determine an inter-maxima interval and an inter-minima interval between a first oscillation and a second oscillation. Further, the logic unit may compare the inter-maxima interval and the inter-minima interval to an interval threshold. In addition, the one or more processors may initiate one or more actions based on the interval threshold being reached.

The particular embodiments disclosed above are illustrative only as the disclosure may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the disclosure. Accordingly, the protection sought herein is as set forth in the claims below. In addition, all examples, embodiments, and/or elements may be combined in any manner that are disclosed in this document. In other words, an element from a first example (paragraph [0088]) can be combined with any other element, such as, a second element from an Nth example (paragraph [0163]). For brevity, all these examples are not written out but are part of this document.

Embodiments disclosed herein provide for detecting an epileptic seizure based upon an ictal component or content of a body signal value of a patient. The ictal component may be determined based upon the body signal value, a reference value of the body signal, and a work level of the patient. One or more body signals of a patient may be acquired in a time series, from which a current body index value is determined and a work level of the patient may be determined based on the body index value relative to one of a body index reference value, a temporal fiducial or an activity level. The ictal component of the current body index value may be determined based upon the work level, as well as the current body signal value and the reference value. The magnitude of the ictal component may then be used to determine whether or not an epileptic seizure has occurred. If a seizure has occurred, a seizure detection may be issued. In response to issuing the seizure detection, a responsive action may be taken. The responsive action may include providing a warning, logging the epileptic event, providing a therapy, and/or providing a warning.

Figure 22:
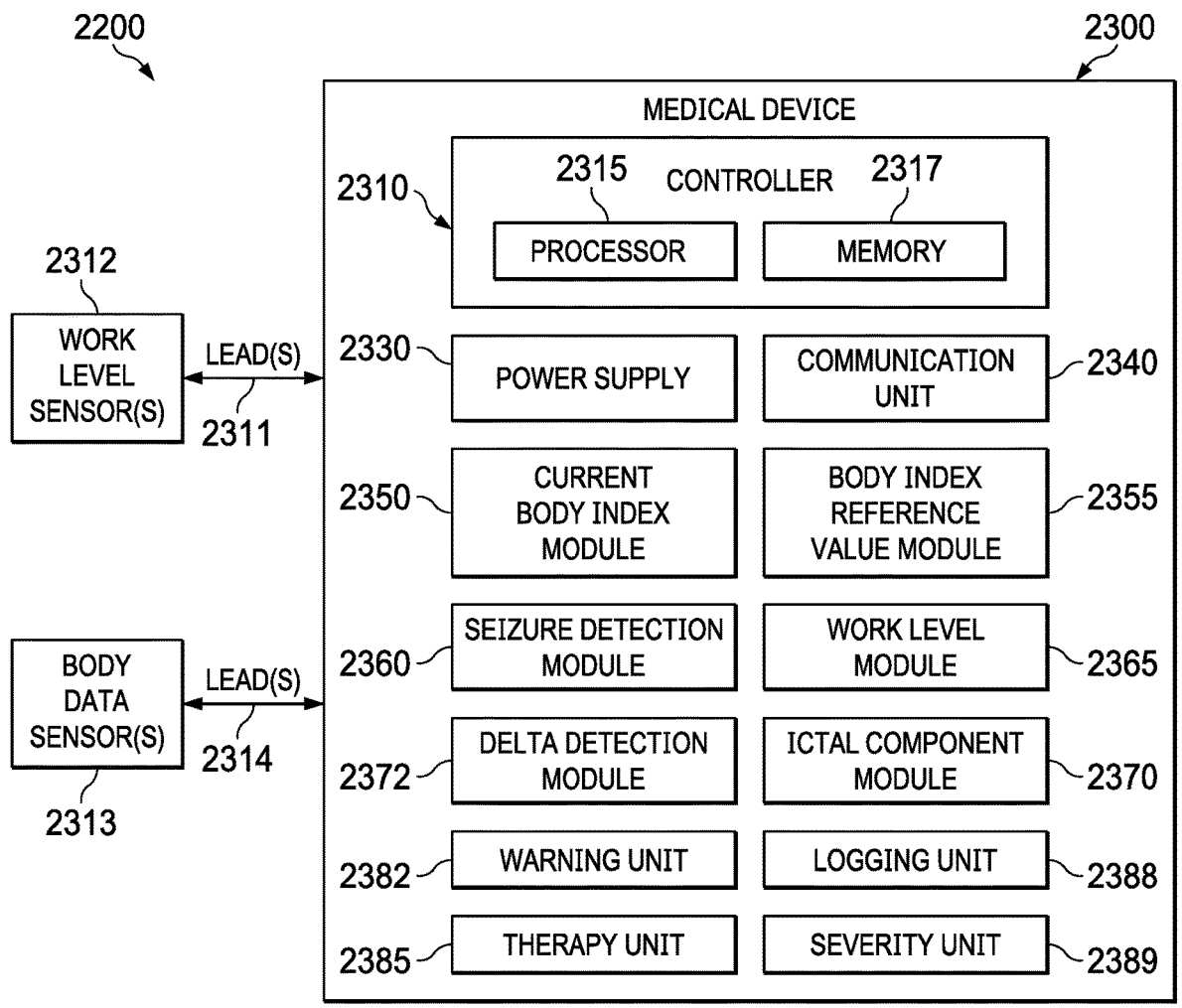
FIG. 22 shows a schematic diagram of a medical device system, in accordance with some embodiments of the present disclosure.

FIG. 22 shows a schematic representation of a medical device system, according to some embodiments of the present disclosure. The medical device system 2200 may comprise a medical device 2300, sensor(s) 2312, and lead(s) 2311 coupling the sensor(s) 2312 to the medical device 2300. In one embodiment, sensor(s) 2312 may each be configured to collect at least one body signal (e.g., kinetic activity, differences in arterial and venous blood oxygen levels, etc.) from a patient relating to a work level of the patient. Generally, work level refers to a patient's energy consumption for any action/behavior performed by the patient, which may conveniently be measured, directly or indirectly, from body movement, oxygen consumption, brain activity, or the like. The classical definition of work (e.g., W=force×distance) is not excluded by this definition, but is only one (indirect) way of establishing the patient's energy consumption.

In one embodiment, the current body signal value (e.g., HR=82 bpm) may be considered a dependent variable and the work or activity level may be considered an independent variable. The value of the dependent variable (e.g., respiratory rate) may be plotted as function of the value of the independent variable (e.g., patient is jogging) and deviations from their physiological relationship (that are indicative of a pathological state) may be determined and used to take various responsive actions.

In another embodiment, the work or activity level may be the dependent variable and the body signal used as proxy (e.g. oxygen consumption; kinetic activity) to determine their values may be the independent variable. In some embodiments, each sensor(s) 2312 may be selected from an accelerometer, an inclinometer, an electromyography (EMG) sensor, a muscle temperature sensor, an oxygen consumption sensor, a lactic acid accumulation sensor, a sweat sensor, a neurogram sensor, a force transducer, or an ergometer. In some embodiments, oxygen sensors, in/on the superior vena cava, in/on the jugular veins in/on the left ventricle, in/on the right ventricle, in/on the aorta or in/on one of its main branches, on the inferior vena cava or on the pulmonary arteries and veins may provide sufficient data to calculate total body (or brain) oxygen consumption, by measuring the difference in oxygen saturation or concentration between structures on the arterial compared to the venous side and based on said difference determine work level. Energy consumption by the patient may be derived from the oxygen consumption levels in some embodiments, while in other embodiments the oxygen consumption may be used as a measure of energy expenditure.

Various components of the medical device 2300, such as controller 2310, processor 2315, memory 2317, power supply 2330, communication unit 2340, warning unit 2382, therapy unit 2385, logging unit 2388, and severity unit 2389 have been described in other patent applications assigned to Flint Hills Scientific, LLC or Cyberonics, Inc., such as, U.S. Ser. No. 12/896,525, filed Oct. 1, 2010; U.S. Ser. No. 13/288,886, filed Nov. 3, 2011; U.S. Ser. No. 13/449,166, filed Apr. 17, 2012; U.S. Ser. No. 13/554,367, filed Jul. 20, 2012; U.S. Ser. No. 13/554,694, filed Jul. 20, 2012; U.S. Ser. No. 13/559,116, filed Jul. 26, 2012; and U.S. Ser. No. 13/598,339, filed Aug. 29, 2012; and U.S. Ser. No. 13/678, 339, filed Nov. 15, 2012. Each of the patent applications identified in this paragraph is hereby incorporated herein by reference.

The medical device system 2200 may further comprise at least one body data sensor 2313, which may be coupled to medical device 2300 by at least one lead 2314, or wirelessly in some embodiments. The body data sensor(s) 2313 may be configured to collect data from the patient relating to a time series of body signal values. The body signal may be selected from a cardiac signal (which may be used to determine one or more heart indices such as heart rate or heart rate variability), a blood pressure signal, a respiratory signal, a dermal signal, or a blood oxygen saturation signal, among others. The body signal may be processed to determine one or more body index values based upon the time series of body signal values.

In some embodiments, data relating to both a body signal (such as one of those listed above) and a work level may be collected by a single sensor or sensor type, i.e., in some embodiments, sensor(s) 2312 and body data sensor(s) 2313 may both refer to the same structure. In other embodiments, separate sensing elements may be used to sense patient work level and the patient body signal.

The medical device 2300 may comprise a current body index module 2350 configured to receive a time series of body data from the body data sensor(s) 2313. The current body index module may process or use the time series of body data to determine (e.g., by calculation) one or more body indices from the time series of data. The current body index value may be based on a most recent time period of said time series comprising from about 1 sec (e.g., an instantaneous body signal value) to about 60 sec. In one example, a cardiac signal may be received from sensor(s) 2313 and used to determine a short-term heart rate (e.g., a median heart rate in a time or number-of-beats window).

The medical device 2300 may comprise a work level module 2365 configured to determine a work level of the patient, based at least in part on a signal from work level sensor(s) 2312. The work level signal may be at least one of a neurologic signal (e.g., a kinetic signal or a brain activity signal), a metabolic signal an endocrine signal, an autonomic signal, or a tissue stress signal. The work level determination may, in some embodiments, take into account one or more of a time of day, an indicator of the patient's overall health, an indicator of the patient's overall fitness, an indicator of the patient's level of consciousness (e.g., wakefulness v. sleep), an indicator of the patients activity level (e.g., walking at a certain pace on a level surface or on a 15° incline), the ambient temperature, the ambient humidity, altitude, or other patient or environmental conditions.

The medical device 2300 may comprise a body index reference value module 2355. The body signal reference value module 2355 may be configured to determine at least a first body index reference value. The first body index reference value may correspond to a value of the first body index that would indicate a transition from a non-pathological state to a pathological state at a particular patient work level, as determined by the work level module 2365. Where the reference value is specific to a particular work level, it may provide a pathological/non-pathological boundary for a particular patient state, e.g., resting while awake, asleep, exercising, etc., and may indicate an upper or lower current body index value boundary associated with a change from a non-pathological to a pathological state (e.g., an epileptic seizure). If the first body index reference value is a limit above which the patient would be expected to be in a pathological state (e.g., an upper epileptic seizure boundary), a current body index value exceeding the first body index reference value would be said to have an ictal component equal to the amount by which the current body index value exceeds the first body index reference value. A current body index value less than or equal to the first body index reference value would not have an ictal component. In some embodiments, the body signal reference value module 2355 may be additionally configured to determine a second body index reference value, which may comprise, for example, a lower limit for a current body index, below which the patient would again be expected to be in a pathological state (e.g., a lower epileptic seizure boundary). In this case, a current body index value less than the second (lower) body index reference value would an ictal component equal to the amount by which the current body index value is less than the second body index reference value, arising from the current body index being pathologically low.

In addition to a patient work level, the first and/or second body index reference value(s) may further be based on one or more of a body signal, a time of day, the prevailing environmental conditions (e.g., temperature, humidity) an indicator of the patient's overall health, an indicator of the patient's overall fitness, or an indicator of the patient's wakefulness. The at least a first body index reference value may be determined for a first time period that is the same as, shorter than, or longer than a time period associated with the current body index value determined by the current body index module 2350.

The medical device 2300 may comprise an ictal component module 2370 configured to determine whether the current body index value comprises an ictal component, based on a comparison of the current body index value and the body index reference value. The ictal component module 2370 may be configured to determine whether the current body index value has an ictal component by determining whether a current body index value is above an upper non-pathological reference value or below a lower non-pathological reference value. The ictal component module 2370 may further determine whether a current body index value comprises an ictal component based on one or more of a time of day, an indicator of the patient's overall health, an indicator of the patient's overall fitness, an indicator of the patient's wakefulness, a time since a most recent previous seizure, an average inter-seizure interval, a severity of a most recent previous seizure, or an average seizure severity.

The medical device 2300 may comprise a seizure detection module 2360 configured to detect a seizure, based on an output of the ictal component module 2370 indicating that the current body index value comprises an ictal component.

Figure 23:
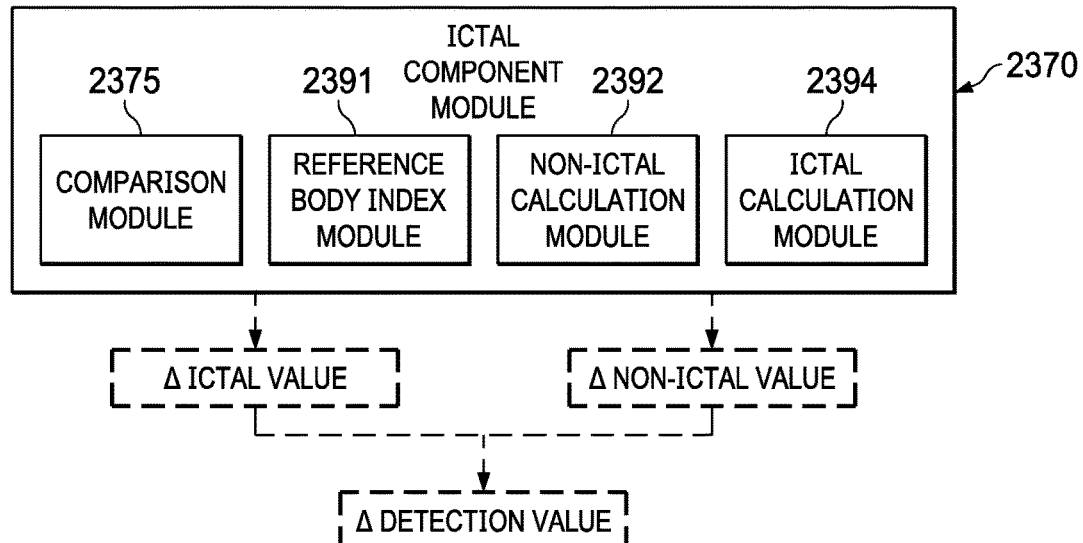
FIG. 23 shows a schematic diagram of a ictal component module of a medical device system, in accordance with some embodiments of the present disclosure.

FIG. 23 shows a schematic representation of the ictal component module 2370 in greater detail, according to some embodiments of the present disclosure. The ictal component module 2370 may comprise a reference body index module 2391 configured to receive body index reference values from body index reference value module 2355 and provide the reference values to other components of the ictal component module 2370. The reference body index values may be specific for a particular non-pathological work level or state of the patient (e.g., sleeping, waking & ambulatory, vigorous exercise). The reference body index values may comprise, e.g., a measure of central tendency (e.g., median, quartile or some other statistical measure) for a microscopic (e.g., 1-10 sec.), mesoscopic (e.g., 11 sec.-24 hr) or macroscopic (e.g., >24 hr) time scale, and may optionally take into account patient or environmental conditions.

The ictal component module 2370 may comprise a comparison module 2375 configured to compare the current body signal value and the at least a first body signal reference value.

The ictal component module 2370 may comprise a non-ictal calculation module 2392 and an ictal calculation module 2394. The non-ictal calculation module 2392 may be configured to determine a non-ictal component of the patient's current body index value from information provided by the current body index module 2350 and/or the reference body data table 2391. The ictal calculation module 2394 may be configured to determine an ictal component of the patient's body data from other information provided by the current body index module 2350 and/or the reference body data table 2391.

The ictal component module 2370, as a result of operations of the non-ictal calculation module 2392 and the ictal calculation module 2394, may provide outputs comprising a ΔIctal (e.g., seizure) value and a ΔNon-Ictal (e.g., physical, cognitive or emotional activity) value, for use by the seizure detection module 2360. Also, from the ΔIctal value and the ΔNon-Ictal value, a ΔDetection value may be determined.

Figure 24A:
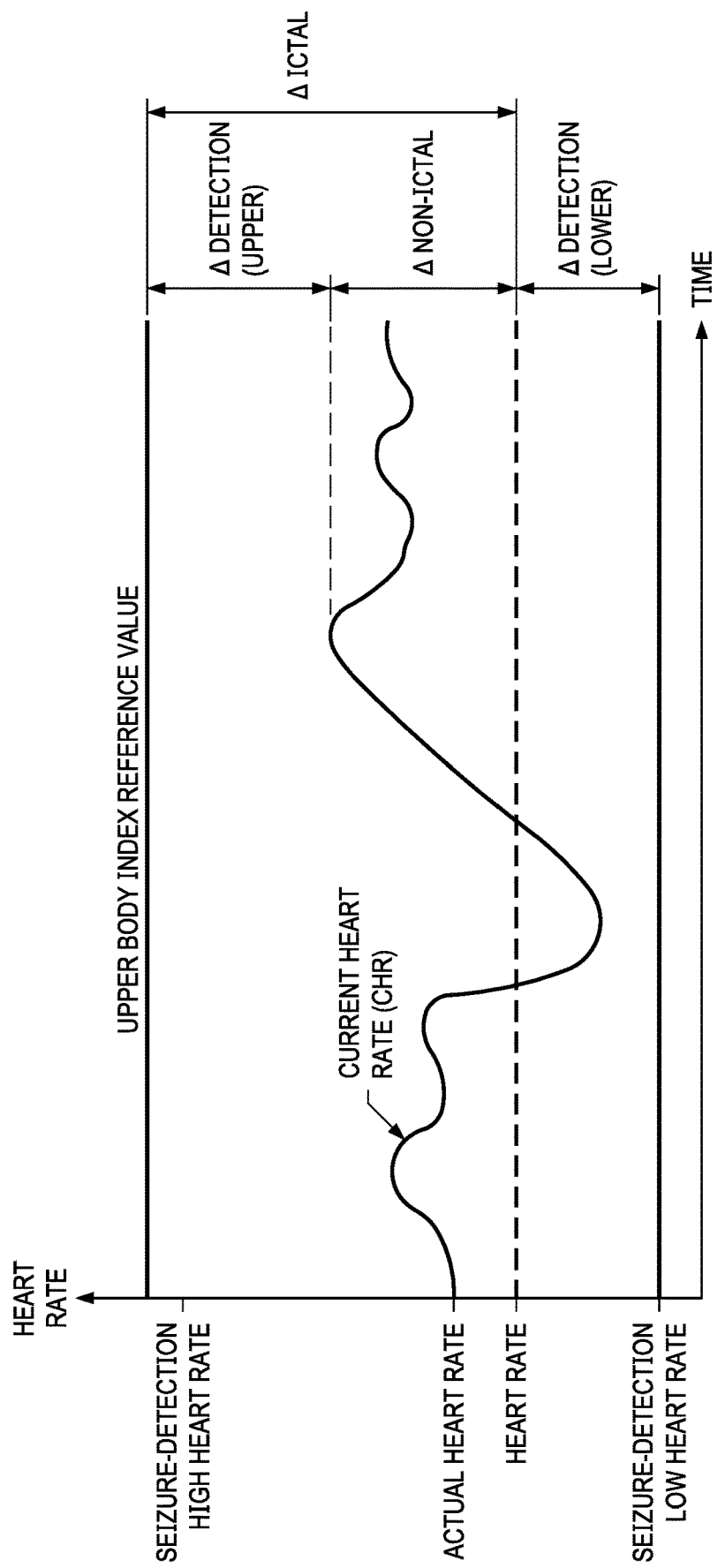
FIG. 24A shows an example of the ΔDetection, ΔNon-Ictal, and ΔIctal components of heart rates, according to some embodiments of the present disclosure.

FIG. 24A provides a simplified diagram of heart rate and seizure detection thresholds to illustrate certain concepts in connection with some embodiments of the present disclosure. FIG. 24A shows an exemplary reference heart rate (the patient's resting heart rate), a current ("actual") heart rate, a high (upper) seizure detection threshold (for seizures that increase the heart rate), a low (lower) seizure detection threshold (for seizures that decrease the heart rate), along with differences between the various heart rate and threshold values known as ΔDetection, ΔNon-Ictal, and ΔIctal, according to some embodiments of the present disclosure. The x-axis shows time, and the y-axis shows heart rate. The dashed line shows a resting heart rate (RHR) as an exemplary reference heart rate. Different or additional reference heart rates may also be used in certain embodiments. The non-resting heart rate (or other reference heart rate) is used as a fixed parameter for purposes of determining ΔNon-Ictal, and ΔIctal values. In some embodiments, RHR may be periodically updated to reflect longer-term changes in the patient's condition.

More information on measures of central tendency and time windows for determining body data values from a time series of body data can be found in U.S. Ser. No. 12/770,562, filed Apr. 29, 2010; U.S. Ser. Nos. 12/771,727; and 12/771,783, both filed Apr. 30, 2010, all three of which are hereby incorporated herein by reference.

In one embodiment, a patient's current heart rate (CHR) while at rest or physically active, and an upper seizure detection threshold heart rate (USDTHR) may be used to determine a value, ΔIctalU, that indicates an increase in heart rate associated with the onset of a seizure characterized by elevated heart rate according to the formula:

$$\Delta \text{Ictal}U = \text{USDTHR} - \text{CHR},$$

where the ictal component in CHR is either absent or the non-ictal component has been determined.

Depending on various factors, such as the level of motor activity (e.g., motionless, tonic or clonic activity or other movements) during a seizure, the increase in heart rate may be solely or primarily (e.g., in the case of seizures causing motionless tachycardia) attributable to the brain's abnormal electrical activity (e.g., the neurogenic component). With tonic-clonic seizures, on the other hand (which are the other end of the movement/kinetic spectrum from motionless seizures), heart or respiratory rate changes have neurogenic, exertional and metabolic components. It should be noted that the seizure detection threshold may or not represent the maximal increase in heart or respiratory rate caused by a seizure, but is instead an exogenous value that is selected based on clinical or safety considerations. For example, if seizure warning and blockage must (for therapeutic efficacy and/or safety considerations) take precedence over accuracy of detection, the detection threshold may be set at a level in which the ictal component is still low. The seizure detection threshold is different from the endogenous separatrix or threshold between body functions or signals without and with an ictal/seizure component (e.g., a change in their value or function caused by or associated with a seizure.

FIG. 24A illustrates the upper seizure detection threshold (USDTHR) as a fixed heart rate value, although in other embodiments (such as that shown in FIG. 24B) the seizure detection threshold may be dynamically adjusted. The patient's resting heart rate (RHR) value may be an instantaneous (e.g., present beat) rate or an average or median heart rate for a time window or a number-of-beats window, determined from data while the patient is at rest. Percentiles or deciles of resting heart rate data may be also used as RHR values in some embodiments.

A similar value, ΔIctalL ("delta ictal lower",) may be calculated to indicate a decrease in heart rate associated with a seizure characterized by reduced heart rate, according to the formula:

$$\Delta \text{Ictal}L = \text{CHR} - \text{LSDTHR},$$

where the ictal component in CHR is either absent or the non-ictal component has been determined to indicate the value in the reduction in heart rate solely attributable to the onset (e.g., the neurogenic component) of a seizure characterized by reduced heart rate for a resting patient. LSDTHR is a lower seizure detection heart rate threshold.

From the patient's current heart rate (CHR), and the resting heart rate (RHR), a difference referred to as ΔNon-Ictal defined in one embodiment as any increase in the current heart rate not caused by a seizure. More generally, the ΔNon-Ictal is defined as any change (positive or negative and of any magnitude or rate) in the value of a signal, caused by physiological activity.

This value corresponds to the magnitude of the increase in the patient's current heart rate above the resting heart rate, and indicates how much of the patient's heart rate is attributable to non-pathological physical activity (e.g., standing up from a sitting position, walking up stairs, exercising), cognitive activity (e.g., mental effort such as problem solving), and/or emotional activity (e.g., exposure to a fearful situation), by subtracting out the contribution of the RHR.

In one embodiment, the ΔNon-Ictal and the ΔIctal may be computed in reference to the resting heart rate or to other reference value as taught in in co-pending application Ser. No. 14/170,389, filed Jan. 31, 2014 entitled "Parametric Seizure Detection," which is hereby incorporated by reference herein in its entirety.

From the current heart rate (CHR) and one of: a) an upper seizure detection threshold USDTHR and/or b) a maximal change in the value (positive or negative) of a body signal caused by or associated with a seizure (ΔIctalmax), differences referred to as an upper ΔDetection (ΔDetectionU) may be calculated as:

$$\Delta \text{Detection}U = \text{USDTHR} - \text{CHR};$$

$$\Delta \text{Detection}U\text{max} = \Delta \text{Ictalmax} - \text{CHR}$$

As seen from FIG. 24A, ΔDetectionU is a measure of how far the patient's current heart rate (CHR) is below a (fixed or dynamic/adaptable) upper seizure detection threshold, USDTHR or the ΔDetectionL=CHR−LSDTHR. The greater the distance, the lower the probability of false negative detections. and the greater the probability of false positive detections. The smaller the distance, the higher the probability of false negative detections and the lower the probability of false positive detections. Thus, the magnitude of ΔDetectionU is an approximate measure of the likelihood (e.g., low) or of the probability (e.g., 60%) that an event may be missed (e.g., false negative detection) or that CHR values caused solely by physical or mental activity (ΔNon-Ictal) may be detected as a seizure (false positive detection).

The minimal possible heart rate may or may not be the same as the resting heart rate and the maximal possible heart rate may or may not be the same as the maximal ictal heart rate. The resting, ictal and exertional heart rates may vary as a function of multiple factors, making the ΔDetection variable in magnitude. In general, the lower the non-ictal heart (non-ictal heart rate encompasses resting and exertional heart rates) and the higher the ictal component, the larger the ΔDetection. A probability index for ictal detections may be estimated based on the values of the non-ictal components of a body signal and a correction or normalization may be introduced to decrease the number of FN detection when the non-ictal component is high or the ΔIctal is low.

A lower "ΔDetection" value may be determined from the CHR and a lower seizure detection heart rate threshold (LSDTHR) for seizures characterized by a decrease in heart rate that are often below the lower range of normal heart rate (e.g., the seizure may cause the heart rate to be lower than the normal resting heart rate). This value may be referred to as a lower delta detection or ΔDetectionL, and may be calculated as:

$$\Delta DetectionL = CHR - LSDTHR;$$

$$\Delta DetectionLmax = CHR + (-\Delta Ictalmax)$$

The magnitude of ΔDetectionL indicates how far the CHR is above the lower seizure detection threshold LSDTHR or the (−ΔIctalmax). The greater the distance, the lower the probability of false negative detections and the greater the probability of false positive detections. The smaller the distance, the higher the probability of false negative detections and the lower the probability of false positive detections. Thus, like ΔDetectionU, the magnitude of ΔDetectionL may be used to assess the likelihood (e.g., high or low) or of the probability (e.g., 20%) that an event may be missed (e.g., false negative detection) or incorrectly detected (false positive detection). The rate of the change in the value (positive or negative) of a body signal caused by a seizure may also indicate the likelihood or probability of false positive or false negative detections and provide insight into the time available for a detection.

Figure 27A:
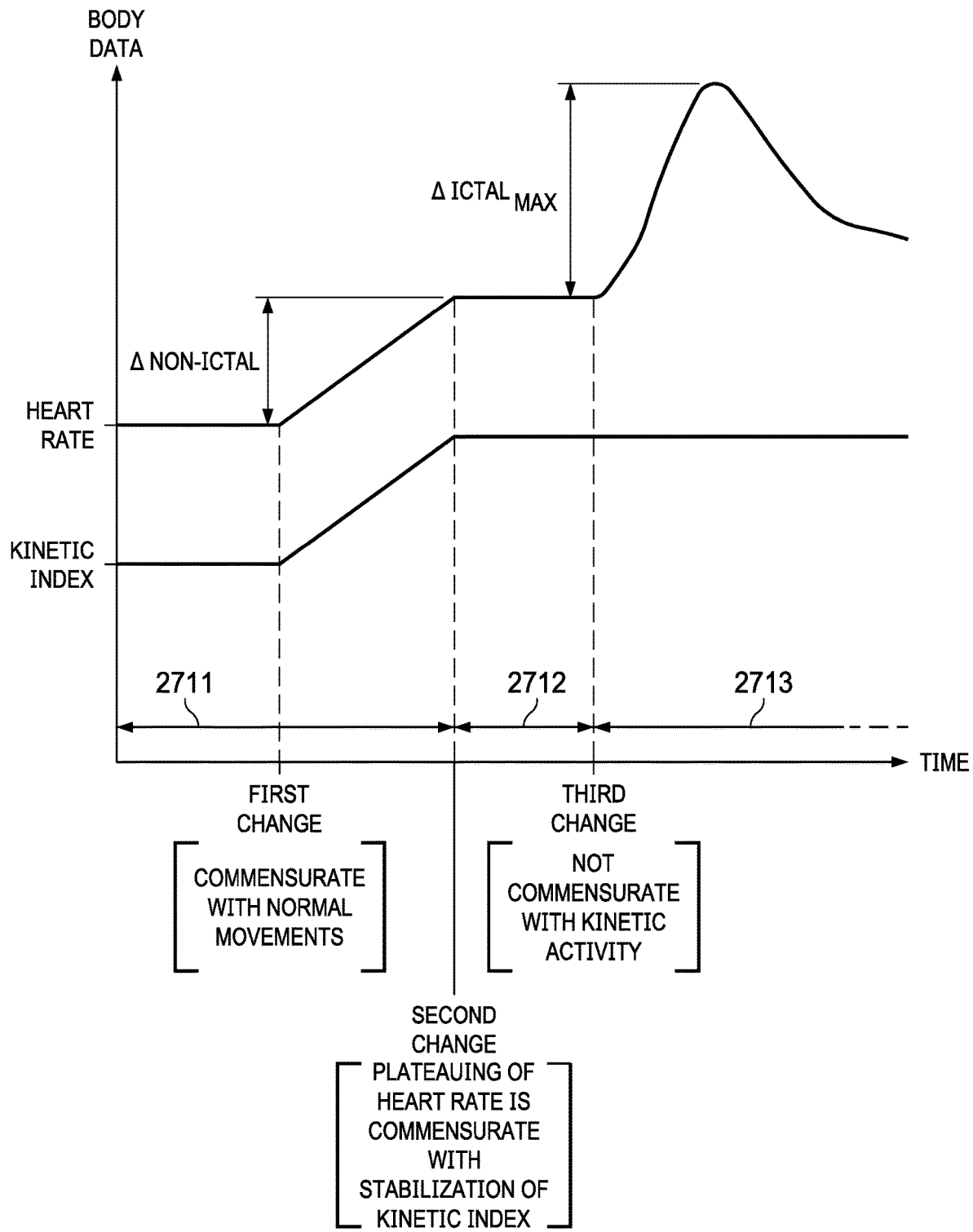
FIG. 27A shows a stylized depiction of a heart rate change in conjunction with a kinetic index, in accordance with a first embodiment.

As may be seen graphically in FIG. 27A, the value of upper or lower maximal change in signal value caused by or associated with a seizure (ΔIctalmax), may be determined by the equation:

$$\Delta Ictalmax = |Maximal\ signal\ value - \Delta Non-Ictal|.$$

If ΔNon-Ictal=0, then ΔIctalmax=|Maximal signal value−CHR|, CHR as used in this embodiment indicates a value that remains stable and has not been subject to a physiological or pathological change immediately before or at onset of a seizure.

The magnitude of the difference in the value of a signal between its current value and the ΔIctalmax impacts the performance of any detection algorithm in terms of false positives, false negatives, and speed of detection. This difference, referred to herein as ΔDetectionmax, may be computed as $$\Delta Detectionmax = |\Delta Ictalmax - CHR|.$$

ΔDetection may be a function of the value of the signal change at which detections are issued (based on a detection threshold value), and is referred to herein as ΔDetectionT, as shown by:

$$\Delta DetectionT = |USDTHR - CHR|;$$

$$\Delta DetectionT = |LSDTHR - CHR|.$$

Figure 27B:
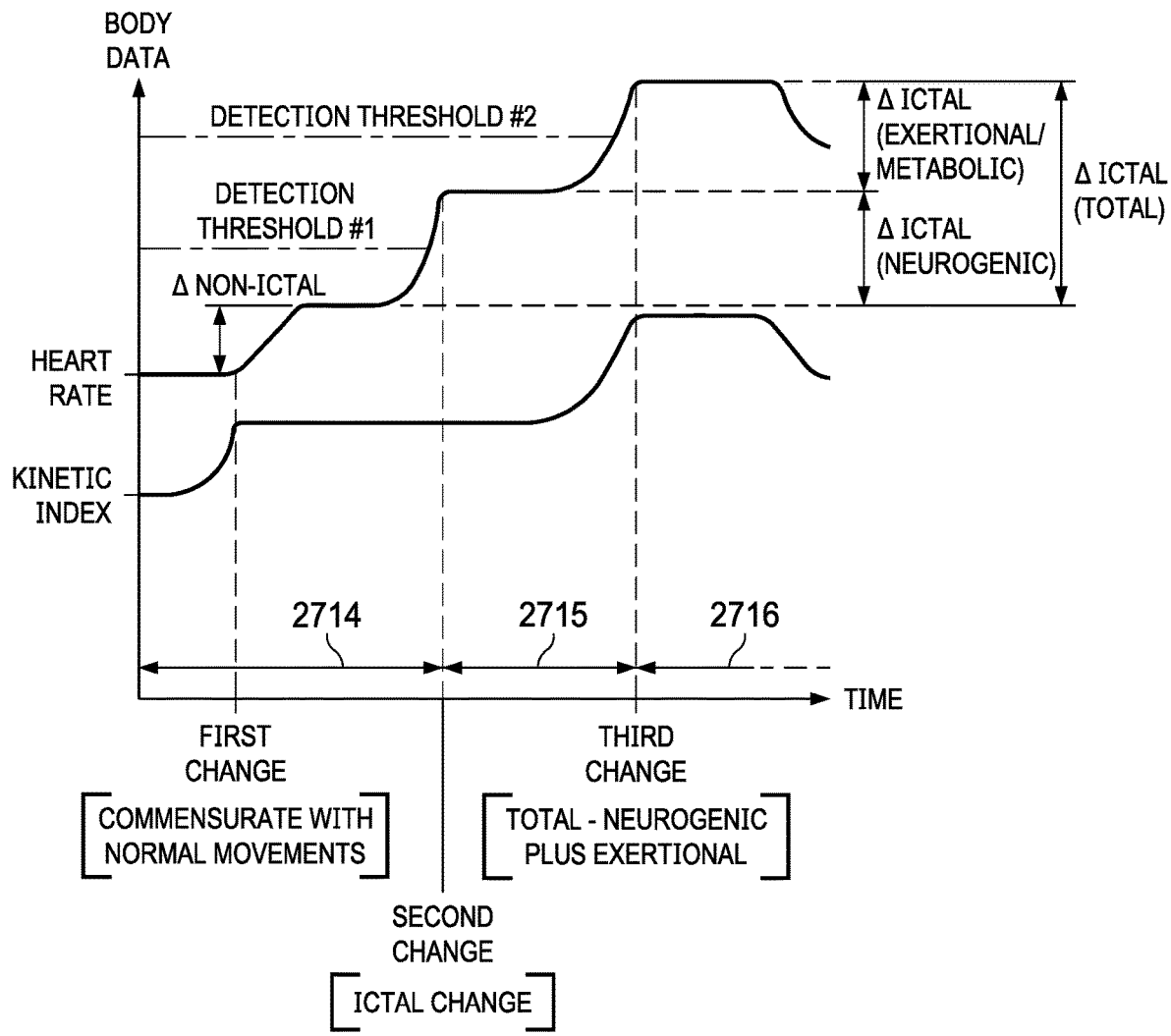
FIG. 27B shows a stylized depiction of a heart rate change in conjunction with a kinetic index, in accordance with a second embodiment.
Figure 27C:
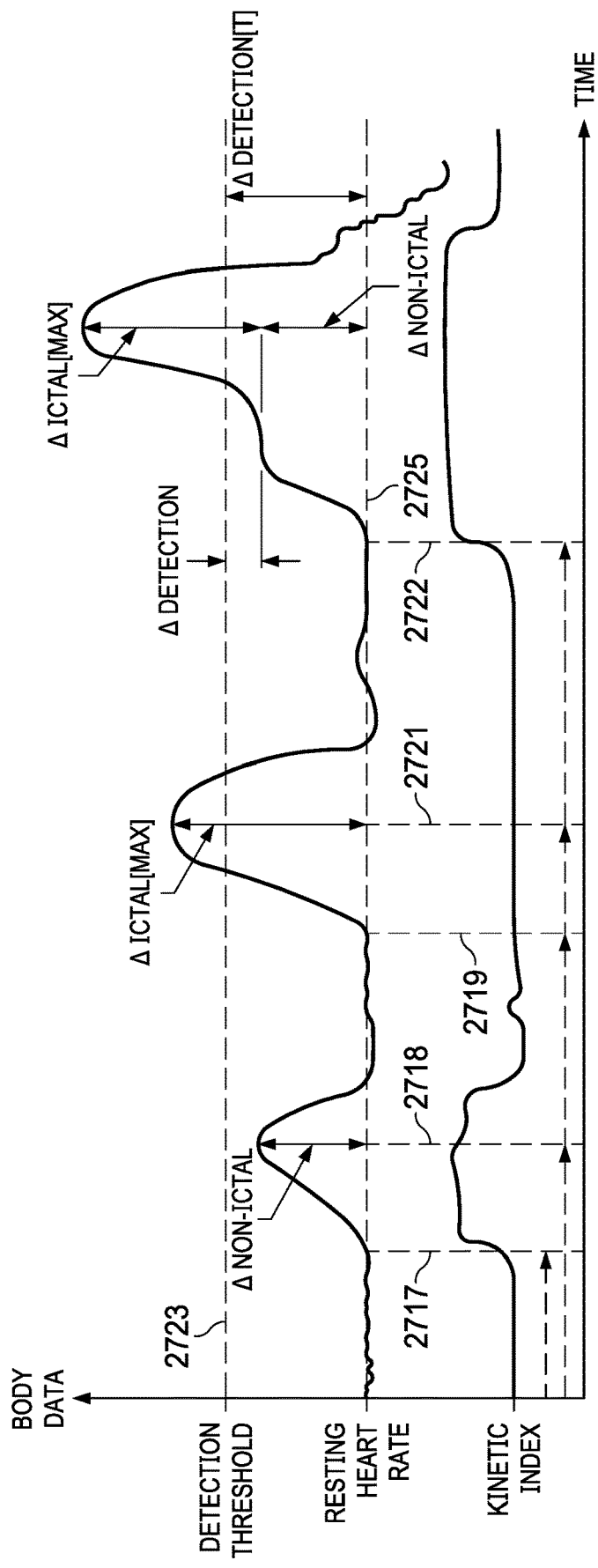
FIG. 27C shows a stylized depiction of a heart rate change in conjunction with a kinetic index, in accordance with a third embodiment.

Values of ΔDetectionU and ΔDetectionL may be computed as an arithmetical or algebraic, or absolute difference according to the foregoing formulae, and may be a valuable indicator or prognosticator of the performance (e.g., sensitivity, specificity, speed of detection) of seizure detection algorithms, and may be used to shape the performance of seizure detection methods. Moreover, knowledge of the changes or alterations in the magnitudes or patterns or rates of ΔDetectionmax or ΔDetectionT may be used to estimate in advance, the probability of correctness of event detections (for certain seizures using certain detection parameters) for optimization performance purposes. For the avoidance of confusion, ΔDetectionmax is the maximal increase in a body signal (e.g., from the pre-ictal body signal value) caused by a seizure and ΔDetectionT is the magnitude of the change between the pre-ictal body signal value and the detection threshold. For example, in the case of ΔDetectionmax=+35 bpm, the ΔDetectionT may be anywhere between +1 bpm and +35 bpm. Note that ΔDetectionmax is equal to ΔIctalmax. Changes in the value of a body signal may be classified as either physiological/non-ictal (ΔNon-Ictal) or pathological/ictal (ΔIctal) by cross-referencing the body signal value (e.g., heart rate) used for detection with at least one different feature (e.g., EKG morphology) of the same body signal (e.g., cardiac) or with at least one different signal (e.g., kinetic activity, respirations, EEG, etc.). For example, FIGS. 27A-C show that, in a patient with epilepsy, heart rate is the signal used for seizure detection, the classification of changes in its value as either or non-ictal may be accomplished by concurrently/simultaneously monitoring kinetic activity (body movements, posture, etc.) with a suitable device such as an accelerometer. FIGS. 27A-C illustrate how the dynamic interrelation between ΔNonictal, ΔIctal, ΔDetection, their magnitudes and rates of occurrence, and the value at which the detection threshold is set.

Although shown as a constant value in FIG. 24A, seizure detection thresholds need not be constant (e.g., the same value regardless of the patient's physical, cognitive or emotional activity levels, conditions, etc.), nor comprise a single value; multiple thresholds may be set, each corresponding to a certain probability of correctness of detection or positive predictive value or speed of detection. In some embodiments, a seizure detection threshold may vary on a preprogrammed basis according to a predetermined protocol. Alternatively, a seizure detection threshold may be dynamically adjusted based at least in part on one or more of patient work levels or activity levels, a time of day, an indicator of the patient's overall health, an indicator of the patient's overall fitness, level of consciousness, the magnitude of changes of ictal and non-ictal components (as explained hereinafter) of a body signal, a time since a most recent previous seizure, an average, variance or some other measure of inter-seizure interval, a severity of a most recent previous seizure, or an average or some other measure of seizure severity.

In alternative embodiments, a detection threshold (or declarations of a detected seizure) may be altered based at least in part on ΔDetection values. For example, if heart rate is the signal being used for seizure detection, the CHR immediately before seizure onset was 80 bpm, and the magnitude of a ΔDetectionmax is +35 bpm, a seizure would be declared only when the heart rate increased sufficiently to reduce the value of ΔDetectionmax to 0 (which occurs when the CHR reaches the maximum ictal value. However, in some embodiments, seizures may be declared well before (e.g., in this example when ΔDetectionT=+5 bpm) the heart rate reaches the ΔDetectionmax, for safety and/or therapeutic efficacy reasons. For example, if a patient who has seizures that render the patient unaware and/or unresponsive is operating a motor vehicle, early warning (before loss of cognitive and other brain functions results in unawareness or unresponsiveness) is desirable for safety reasons. Under this circumstance, a detection may be issued for ΔDetectionT=+5 bpm to provide a margin of safety to protect the patient and/or others. On the other hand, in other embodiments, e.g., if the same patient is lying down in bed so safety risks are minimal and automated therapy is associated with certain adverse effects, a seizure detection may be issued (or therapy or a warning provided) only when ΔDetectionT=+25 bpm to minimize the probability of false positive detections and the anxiety to the patient or caregivers associated with an erroneous detection.

Figure 24B:
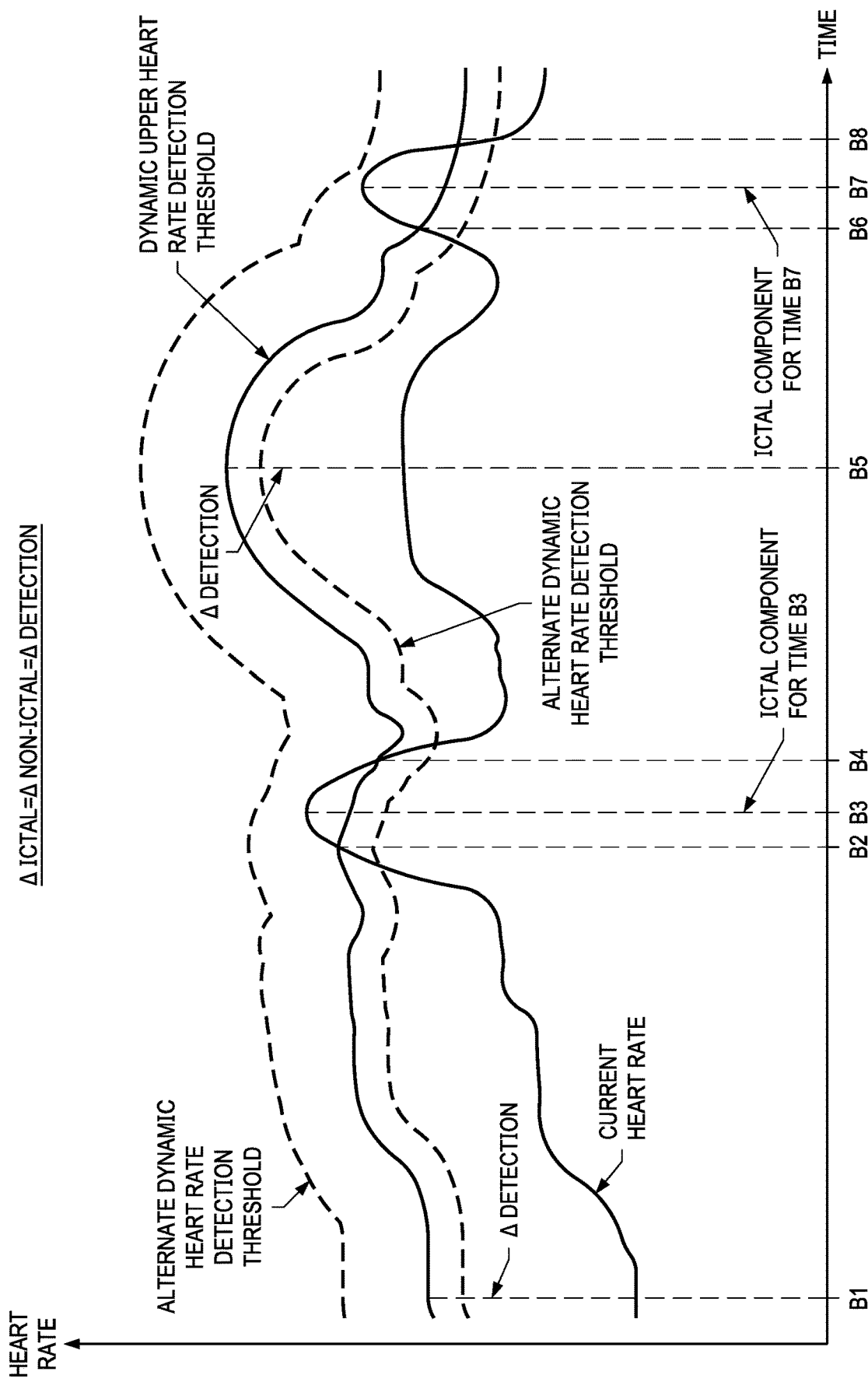
FIG. 24B shows an example of the ΔDetection, ΔNon-Ictal, and ΔIctal components of heart rates, according to some embodiments of the present disclosure.

Referring to FIG. 24B, in one embodiment, dynamic upper and lower seizure detection thresholds (e.g., USDTHR and LSDTHR, although for illustrative purposes only USDTHR curves are illustrated in FIG. 24B) may be established as the patient's non-pathological work level changes over time. For example, at point B1 in FIG. 24B, the ΔDetectionU is relatively large, as the ΔNon-ictal is small as it would correspond to a period of rest or reduced motor activity. Conversely, at point B5, the ΔDetectionU is smaller relative to point B1, which corresponds to a period of exercise.

In some embodiments, seizure detection thresholds may vary on a preprogrammed basis based at least in part on time of day, activity/work level and/or other considerations. In some embodiments, seizure detection thresholds may be dynamically adjusted based at least in part on one or more of an indicator of the patient's overall health, an indicator of the patient's overall fitness, an indicator of the patient's wakefulness, a time since a most recent previous seizure, an average inter-seizure interval, a severity of a most recent previous seizure, or an average seizure severity.

Various thresholds for issuing a seizure detection may be set according to the clinical application and the patient's characteristics. In general, the larger the ΔDetection (defined as the difference between the current body signal/index value and one of the maximal change in the signal/index caused by a seizure, or the maximal value (e.g., in the case of HR: 220 bpm-age) attainable by a seizure. More than one threshold may be set and each threshold may be associated with a qualitative statement of likelihood (e.g., low, high) or with a probability estimate (e.g., 60%) based on historical data about the performance (false positive, false negative, speed of detection) of a certain threshold. When HR is the signal/index used for seizure detection, the ictal threshold HRic may be set as low as ΔNon-ictal+1 or as ΔNonictal+ non-integer value. In addition, a seizure detection signal may be generated and a seizure event may be logged.

In FIG. 24B, the CHR has an ictal component 1) from point B2, at which the current heart rate first crosses the heart rate's non-ictal component, to point B4, at which the current heart rate falls back below the non-ictal component of the HR and 2) from point B6 to point B8. At a specific point B3 between points B2 and B4, or B7 between points B6 and B8, the magnitude of the ictal component may be determined by the formula ΔIctal=CHR−ΔNon-Ictal.

The ictal component of heart rate may provide an indication of the severity of a detected seizure. In some embodiments, epileptic seizures may be characterized by the magnitude and/or rate (e.g., slopes) of the ictal component changes from the onset of the seizure until the end of the seizure. In particular, one or more of the shape, duration, and magnitude of the ictal component may be used to characterize and/or classify the seizure event. For example, in FIG. 24B, the seizures associated with points B2-B4 and B6-B8 may be characterized by the shape (e.g., area under the curve or height×base) of the ictal component envelope.

In some embodiments, more than one threshold may be set. Each such threshold may be associated with a qualitative statement of likelihood (e.g., low, high), or with a probability or a percentile value (e.g., 80th) of the particular threshold among a plurality of threshold values associated with similar activity levels, times of day, or historical data about the performance (false positive, false negative, speed of detection) associated with each threshold value.

Figure 24C:
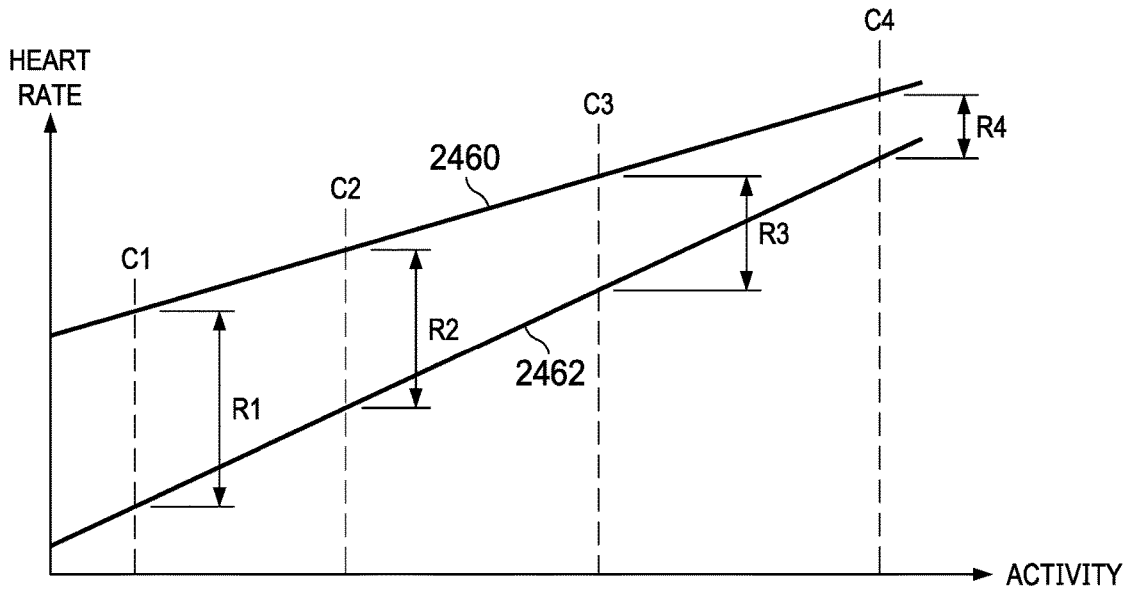
FIG. 24C shows an example of the ΔDetection, ΔNon-Ictal, and ΔIctal components of heart rates, according to some embodiments of the present disclosure.

FIG. 24C shows an idealized dynamic relationship between non-pathological/non-ictal patient activity levels (e.g., as determined from a tri-axial accelerometer) on the x-axis and an exemplary body index (heart rate) on the y-axis. It should be appreciated that in other embodiments, different body indices may be used instead of, or in addition to, heart rate to detect seizures, and dynamic relationships similar to that show in FIG. 24C may be provided. Although non-pathological activity level is shown in FIG. 24C as a single continuous parameter along the x-axis, a plurality of discrete activity levels or states (e.g., resting lying down, resting sitting, working sitting, walking slowly, walking briskly, running, etc.) may also be used to correlate heart rate (or another body index) to activity levels in some embodiments of the invention. Because current heart rate is a variable that may be influenced by many different factors besides activity levels (e.g., the patient's age, sex, body mass index, fitness level, hydration status, environmental conditions such as temperature, humidity, emotional activity, etc.) a particular activity level may correspond to a current heart rate anywhere within the associated non-pathological/non-ictal heart rate range.

As used interchangeably herein, two body signal values (the dependent and independent variables) may be deemed to be "correlated," "coupled," or "commensurate" with one another if under physiological conditions the direction (e.g., increase or decrease), latency, magnitude, rate, and/or duration of the dependent variable as a function of the independent variable are preserved or maintained. For example, if heart rate (HR) increases at a certain rate and by a certain magnitude each time a healthy subject performs the same physical activity (a positive correlation) under physiological conditions, the expected changes in certain body signals for a certain activity type and level are commensurate with those observed. In certain cases, the value of the dependent and independent variables may change in opposite direction (e.g., as one increases, the other decreases). For example, as luminance decreases, the size of the pupils increases.

FIG. 24C shows one embodiment of an activity-based, non-pathological heart rate range, (y-axis), corresponding to a certain activity level (x-axis) bounded by an upper HR boundary line 2460 and a lower HR boundary line 2462. Upper heart rate boundary line 2460 may separate, with satisfactory specificity, certain seizure classes (e.g., convulsions) with signal values above line 2460 at the highest levels (e.g., C3-4) and partial seizures, also with satisfactory specificity, at low-to-mid activity levels (e.g., C1-2) from certain physiological states or activity levels (below the line). The lower heart rate boundary line 2462 separates seizures associated with a certain degree of bradycardia (heart rates below line 2462) from resting (non-pathological) states (above the line 2462 and below line 2460). Thus, in one embodiment, both upper and lower boundary lines 2460, 2462 may be considered as ictal threshold for a given activity level (i.e., a given point along the x-axis). In the case of epileptic seizures, upper HR boundary line 2460 may be considered as an ictal heart rate threshold for seizures having a pathological increase in heart rate, and lower HR boundary line 2462 may be considered as an ictal heart rate threshold for seizures characterized by an abnormal or pathological decrease in heart rate.

The region between the upper and lower boundary lines 2460, 2462 defines a region in which the patient's heart rate may be considered as non-pathological under normal/non-extreme patient and environmental conditions. Both the upper and lower ictal boundaries 2460, 2462 of the non-ictal heart rate region increase as activity level increases (e.g. from a sleep state to a resting, awake state, or from left to right on the x-axis) and reach their highest values for strenuous activity (e.g., strenuous exercise, point C4). In addition, the width of the non-pathological heart rate range (the area between the upper and lower ictal heart rate thresholds 2460, 2462 narrows as activity levels and heart rates increase, which is consistent with the known reduction in heart rate variability at high levels of exertion.

When the patient is in a non-pathological state (e.g., when an epileptic patient is not having a seizure), for a particular activity level the patient's short-term heart rate should fall within a non-pathological heart rate range associated with that activity level. Referring to FIG. 24C, at a particular activity level C1—corresponding, for example, to a sleeping activity level—a non-pathological HR range R1 may be determined between upper and lower ictal heart rate thresholds 2460 and 2462. Another non-pathological heart rate range R2 may be established by upper and lower boundaries 2460 and 2462 for, e.g., resting awake activity level C2. At activity levels C3 and C4, corresponding to moderate and strenuous exercise, respectively, corresponding non-pathological HR ranges R3 and R4 may be determined from upper boundary 2460 and lower boundary 2462. As noted, the width of the non-pathological heart rate ranges decrease as activity levels increase, and thus R1>R2>R3>R4.

Figure 24D:
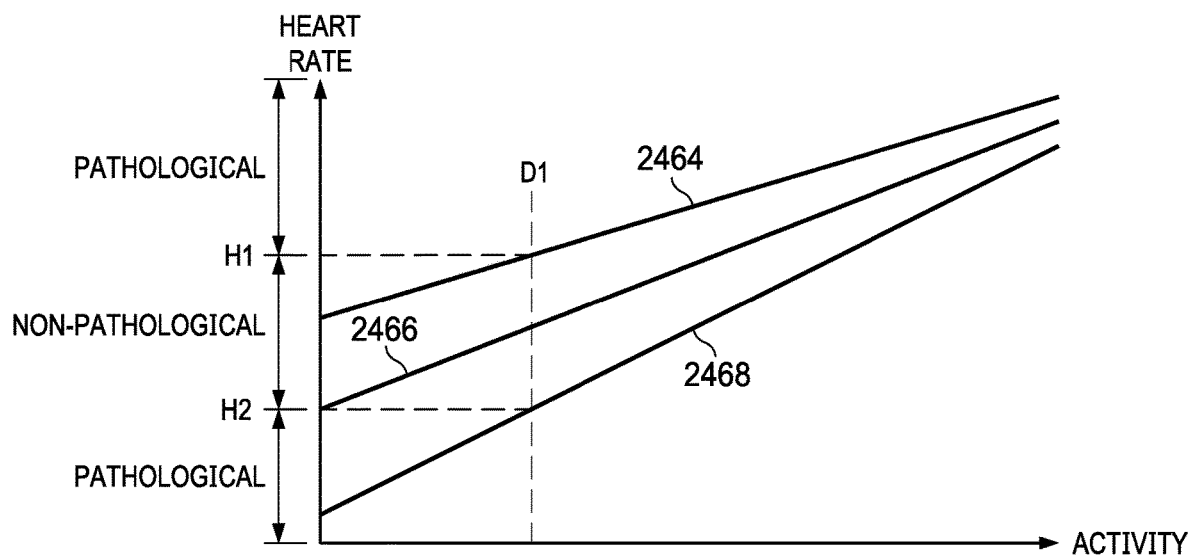
FIG. 24D shows an example of the ΔDetection, ΔNon-Ictal, and ΔIctal components of heart rates, according to some embodiments of the present disclosure.

Referring to FIG. 24D, in another embodiment, non-pathological heart rate ranges as a function of activity level are determined by upper and lower boundaries 2464 and 2468. For a particular activity level D1, the non-pathological range lies between heart rate H1 and H2. At heart rates above H1, the patient's heart rate may be pathologically high (e.g., when the patient is having a seizure characterized by elevated heart rate), while at heart rates below H2, the patient's heart rate may be pathologically low (e.g., when the patient is having a seizure characterized by reduced heart rate).

Upper and lower non-pathological heart rate boundaries 2464, 2468 may be determined from a given patient or from patient population data (taking into account, in some embodiments, age, gender, health status, fitness level, etc.) and stored in a memory of a remote, or implantable or body-worn medical device. For convenience, boundaries 2464, 2466, and 2468 are shown as straight lines. The person of ordinary skill in the art would appreciate that in an actual embodiment these boundaries may be non-linear. When needed, the heart rate data may be retrieved from the memory for use by the medical device to determine whether the patient's heart rate is within a non-pathological range appropriate in view of the patient's activity level. Alternatively, heart rate ranges may be determined by calculation from a formula based on the patient's activity level (e.g., kinetic or based on oxygen consumption), which may optionally take into account one or more additional endogenous factors such as the patient's age, sex, fatigue level, hydration level, general health, and physical fitness, or exogenous factors such as the time of day, humidity, temperature, altitude, etc.

Upper and lower boundaries 2464, 2468 may in some embodiments be determined empirically from patient-specific data collected over time for a variety of activity levels. For example, the patient may be subjected to one or more tests such as a walking test on a treadmill, with heart rates determined at each of a variety of different activity levels (e.g., as determined from one or more of a three-dimensional accelerometer, an electromyogram, gyroscope, and/or imaging devices such as a camera). Other activity level tests may be performed to determine upper and lower boundaries 2464, 2468. In one embodiment, upper non-pathological boundary 2464 may be determined as an upper percentile value (e.g., the 90th, 95th, or 99th percentile) of the non-pathological heart rates measured at a number of different times corresponding to the particular activity level. Thus, a linear or a polynomial may be fitted through the target upper percentile values over a range of activity levels to obtain the upper boundary 2464. Similarly, another polynomial may be fitted through a target percentile value (e.g., 5th, 2nd, 1st) to obtain the lower boundary 2468.

Additional curves may be determined by fitting polynomials to additional target percentile values of the activity level/HR data. Referring again to FIG. 24D, a median boundary line 2466 may be determined by fitting a polynomial through, for example, the 50th percentile values of heart rate across a range of activity levels. Additional percentile values (e.g., an upper quartile or 75th percentile, a lower quartile or 25th percentile, etc.) may be determined similarly (not shown in FIG. 24D). In one hypothetical example, the region between median boundary line 2466 and upper ictal threshold line 2464 may be considered as a hypothetical ΔDetectionU region, since for each activity level it is defined by the difference between the upper ictal threshold and an expected (median) nonictal value of heart rate (although not an actual ΔDetectionU region because median boundary line 2466 is not an actual (current) heart rate as required of true ΔDetectionU values). Similarly, the region between median boundary line 2466 and lower ictal threshold line 2468 may be considered as a hypothetical ΔDetectionL region, since it is defined by the difference between the lower ictal threshold and an expected (but not an actual) nonictal value of heart rate.

In some embodiments of the present invention, upper and lower boundaries of physiological body signal values may be determined so that a value above or below said boundaries indicates the transition into one or more pathological states. For example, separate upper and lower heart rate boundaries of physiological body signal values as a function of activity level and/or other factors may be determined for simple partial seizures, complex partial seizures, or generalized tonic-clonic seizures, among others. Without being bound by theory, these upper and lower boundaries for each seizure type may be determined as specific percentile value curves for a specific body index used to detect seizures as a function of activity levels from a population of values at each activity level or state, as described above. For example, in one embodiment a pathological upper boundary for a simple partial seizure may be above the 90th percentile value for a particular activity level, while a pathological upper boundary for a complex partial seizure may be above the 95th percentile value for a particular activity level.

In some embodiments, upper and lower ictal threshold boundaries for simple partial and complex partial seizures may be determined based on activity levels, oxygen consumption or the results of a responsiveness or awareness test. For example, where the awareness test indicates that the patient has not lost awareness, the heart rates measured while the patient remains aware may be used (along with activity levels) as data to determine upper and lower heart rate boundaries for simple partial seizures. When and if the patient loses awareness, the data of heart rate and activity level may be used to determine upper and lower activity level heart rate boundaries for seizures associated with loss of awareness, such as complex partial, complex partial with secondary generalization, or generalized seizures.

Figure 24E:
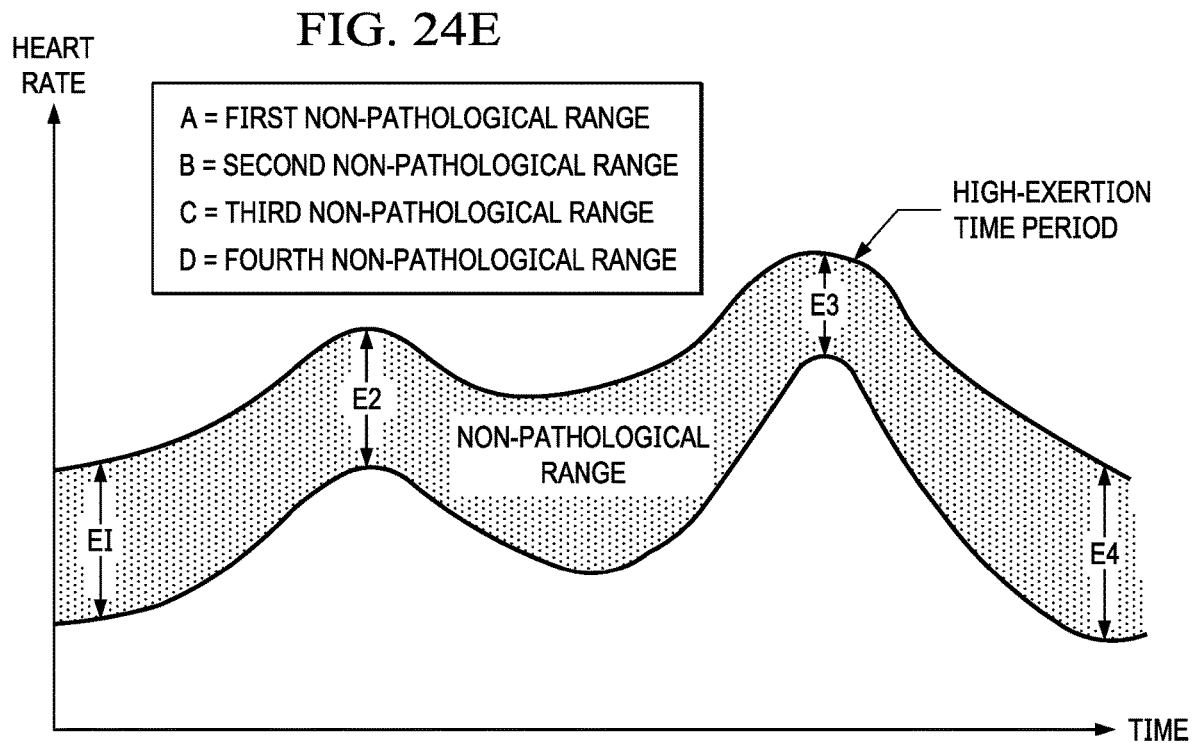
FIG. 24E shows an example of the ΔDetection, ΔNon-Ictal, and ΔIctal components of heart rates, according to some embodiments of the present disclosure.
Figure 24F:
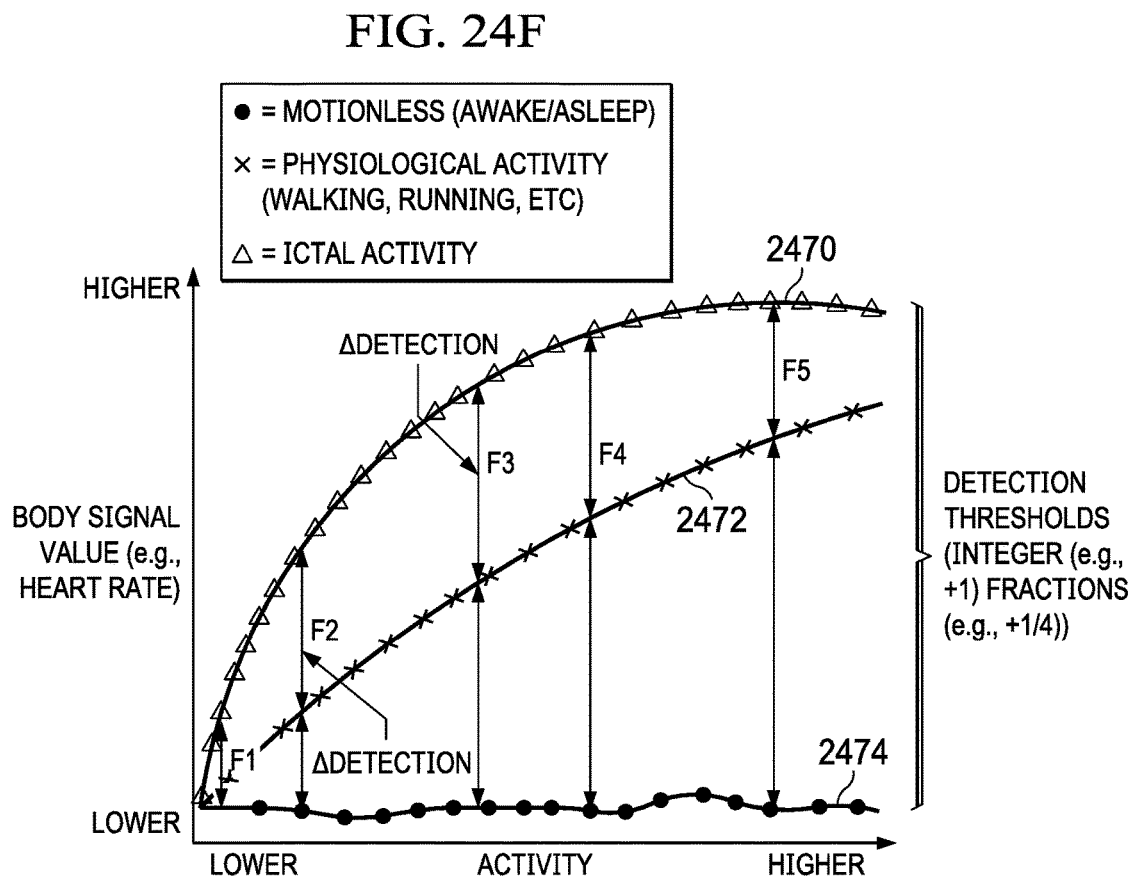
FIG. 24F shows an example of the ΔDetection, ΔNon-Ictal, and ΔIctal components of heart rates, according to some embodiments of the present disclosure.
Figure 24G:
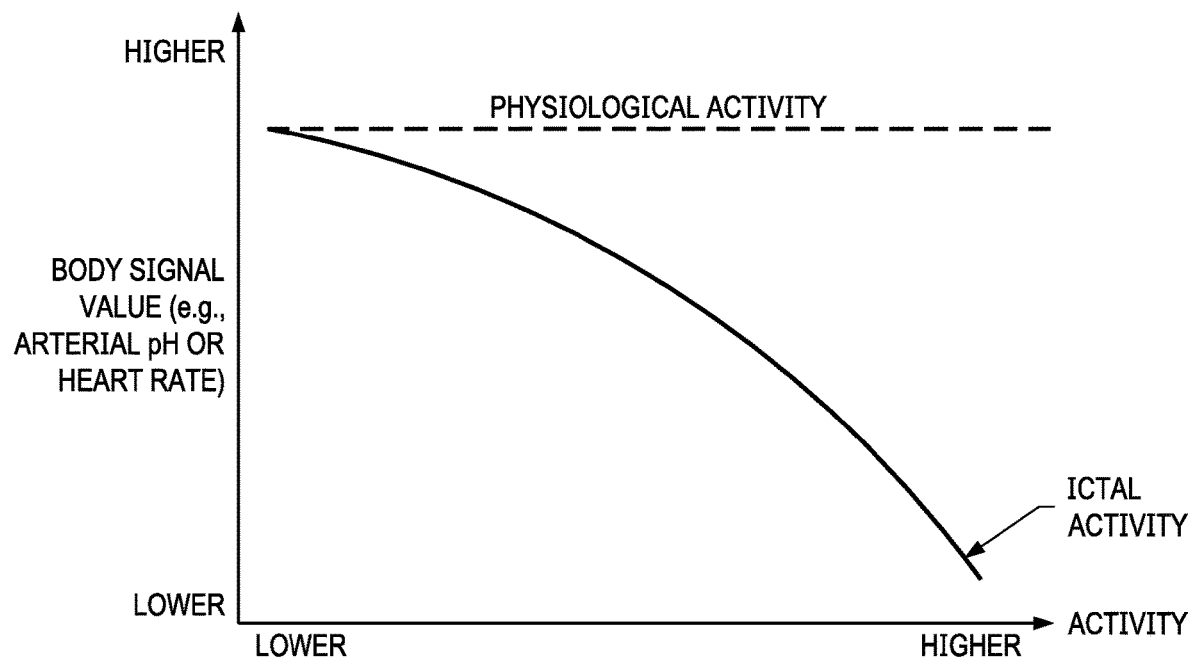
FIG. 24G shows an example of the ΔDetection, ΔNon-Ictal, and ΔIctal components of heart rates, according to some embodiments of the present disclosure.

FIGS. 24C and 24D together show that a non-pathological heart rate (or other body index such as respiratory rate, blood oxygen saturation, etc.) range may be established for a given activity level of the patient. In some embodiments, the range may be a unique range based on historical data for the patient, while in other embodiments data for patient populations may be used, at least until patient-specific data can be obtained. For simplicity, FIGS. 24C and 24D depict the upper and lower boundaries as being linear. It will be appreciated, however, that the boundaries for an actual patient would not necessarily be linear, particularly where additional factors may be considered. FIGS. 24F and 24G illustrate heart rate boundaries that vary in a nonlinear manner with increasing activity levels.

The dynamic relationship between non-pathological heart rates and activity levels may be exploited to detect pathological states such as epileptic seizures by determining when the patient's heart rate is incommensurate with the patient's activity level. By monitoring the patient's activity level and heart rate, it is possible to determine when the patient's heart rate is outside the non-pathological ranges as the patient's activity levels change over time, resulting in improved accuracy (i.e., sensitivity and specificity) in detecting pathological states such as seizures. FIG. 24E shows the patient's heart rate and the dynamically changing non-pathological heart rate range as the patient's activity levels change over time, with time shown on the x-axis and heart rate (HR) and non-pathological heart rate range shown on the y-axis. As patient activity levels change over the course of time (e.g., over the course of a day), commensurate non-pathological HR ranges may be determined and utilized to detect the onset of pathological states. A non-pathological range E1 provides a relatively low range that may correspond to sleeping or resting. A slightly higher (and narrower) range E2 may correspond to higher activity levels of the patient, and a significantly higher (but narrower still) range E3 may correspond to an exercise period, which returns to a lower (and broader) range E4 after the patient stops exercising.

FIG. 24E indicates that the width of a non-pathological body index range may change based on activity levels, optionally in view of additional factors (patient age, sex, fitness level, time of day, etc.) as discussed above. For example, at points E1 and E4, the range may relatively broad, reflecting relatively low activity levels. In contrast, at point E3, corresponding to strenuous exercise, the range may be relatively narrow, arising from the patient's heart rate approaching his or her maximum heart rate. Periods of elevated heart rate due to exertion may be highly correlated with activity level as measured by, e.g., an accelerometer.

Another example of how body signals such as heart rate may be affected by the patient's activity level is illustrated in an exemplary fashion in FIG. 24F. The upper curve 2470 (Δ) delineates ictal heart rate changes partially as a function of seizure intensity, duration and extent of brain/body spread and the lower curve 2472 (x) illustrates a representative curve for non-ictal (i.e., non-seizure) heart rates corresponding to various activity levels of the patient. Both upper curve 2470 and lower curve 2472 may change over short or long time periods based on changes in patient-specific or environmental factors; the examples provided here are for illustrative purposes. For a particular activity level (e.g., any of activity levels F1-F5 in the FIG. 24F), the distance between the ictal heart rate threshold curve 2470 and the non-ictal heart rate curve 2472 indicates an expected or hypothetical value of ΔDetectionmax for that activity level, since it is the difference between the patient's non-ictal heart rate for that activity level (curve 2472) and the ictal heart rate threshold (curve 2470). The lowest curve 2474 represents heart rate value during sleep and resting wakefulness; the magnitude of the ΔDetectionmax for seizures that occur during these states is greater than for those in which the patient is active. These differences in the magnitude of ΔDetectionmax impact detection performance: The larger the ΔDetectionmax, the greater the potential for false positive and for earlier detections and the smaller the ΔDetectionmax, the greater the potential for false negative and late detections.

For patients whose heart/activity relationship resembles FIG. 24F, it may be difficult to distinguish between seizures and non-ictal heart rate changes at both high activity levels and low seizure intensities. At activity levels near the middle of the curve, the distance between the two curves may increase to a maximum value and at this point the ability to discriminate between seizure and non-seizure states may be greatest. Embodiments of the present invention may provide improved accuracy in distinguishing pathological and non-pathological states at high and low activity levels by adjusting threshold values based on activity levels.

FIG. 24G provides simplified diagram illustrating how arterial pH decreases in otherwise healthy patients during convulsions (e.g., generalized tonic-clonic seizures) and how it remains stable during physiological work or activity levels. While ictal decreases in heart rate are well documented, arterial pH (y-axis) is used in this example. Convulsions or generalized tonic-clonic seizures are associated with transient lowering of the arterial pH to an extreme value (e.g., 7.1). Other values may be established for different seizures or pathological states. For this, as well as for any other autonomic, neurologic or endocrine signals a ΔNon-Ictal, ΔIctal or ΔDetectionmax may be computed and a ΔDetectionT may be chosen.

Figure 24H:
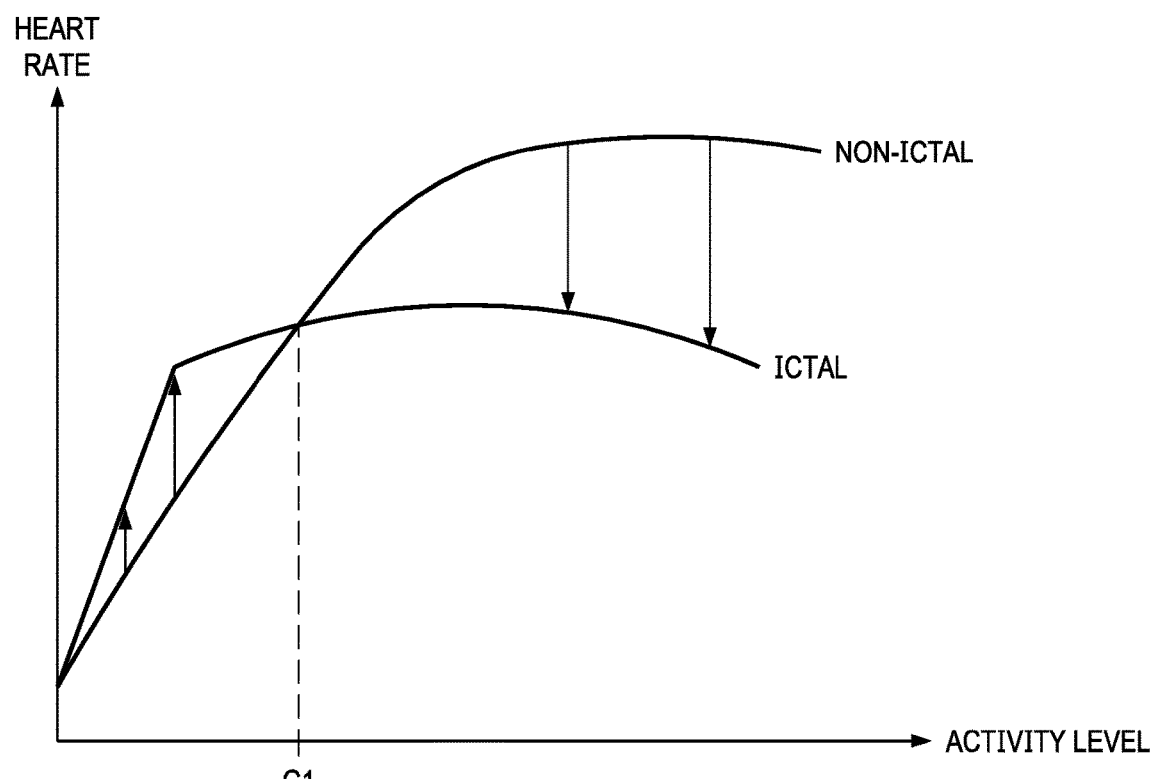
FIG. 24H shows an example of the ΔDetection, ΔNon-Ictal, and ΔIctal components of heart rates, according to some embodiments of the present disclosure.

A further example of how body signals such as heart rate may be affected by the patient's activity level and seizures is illustrated in FIG. 24H. In this figure, the heart rate represented by curve 2474 and corresponding to a seizure, shows a steep initial increase (compared to that of curve 2476 that shows heart rate changes as a function of activity level (x-axis)) that rapidly levels off. In this example, due to the short duration or low intensity of the seizure, the ΔIctalmax (shown by the portion of FIG. 24H in which the ictal HR exceeds the non-ictal HR for a particular activity level) was short-lived, falling below values attainable at certain physiological activity levels, making state-of-the art detection adaptation strategies such as threshold and duration constraint, potentially counterproductive. If either of the threshold (the magnitude of the change in the value of the body signal required to issue a detection) or duration constraint (time that must elapse after a signal value reached a threshold before a detection is issued) are increased beyond certain values in this case, this will result in larger numbers of false positive detection. By inherently taking into account each patient's seizures and physiological changes in signal values, seizure type or severity, and environmental conditions, embodiments of the present disclosure avoid certain state-of-the art seizure detection pitfalls. In this example, accuracy of seizure detection will be highest, as the value of ΔDetection is maximal at point H1.

At point H1, however, the slope of the ictal heart rate curve flattens, such that the non-ictal heart rate curve 2476 has a higher slope (and absolute value) than the ictal heart rate threshold curve 2474. Thus, at higher non-pathological increases in HR values (to the right of H1), the ictal threshold values may fall below the non-ictal heart rate thresholds. When the patient's heart rate is already elevated by exercise, the sympathetic activity may already be relatively high, and parasympathetic activity may be reduced, such that a seizure may have no further effects on sympathetic/parasympathetic balance. Consequently, the heart rate of a patient having a seizure during exercise or exertion may not increase during the seizure, and in some instances may actually decrease. By taking into account these factors and incorporating them into a detection strategy, this invention advances the state-of-the art. In short, unlike the conventional approach that attempts to optimize performance by blindly increasing the threshold and/or duration constraints, this invention may in some embodiments decrease in an informed/intelligent manner, threshold and duration constraints whenever appropriate.

For patients having seizures characterized by decreases in heart rate, the approach or strategy described for ictal HR increase may be reversed. Seizures with reduced heart rate may be associated with ictal-driven reduced sympathetic drive and/or increased parasympathetic drive. For such patients, the ictal heart rate threshold curve may lie below the non-ictal heart rate curve at lower activity levels. For detection purposes, seizures that reduce the heart rate may be easier to detect at higher activity levels than at lower activity levels. While it may not be feasible (for safety/medical reasons and due to current technological limitations) to increase activity level immediately prior to the onset seizures associated with bradycardia, use of certain physiological parameters such as maximal heart rate, resting heart rate or reserve heart rate as reference values, may overcome this inherent limitation. Additional details regarding the use of reference or fiducial heart rates to detect seizure are provided in co-pending application Ser. No. 14/170,389, filed Jan. 31, 2014, entitled "Parametric Seizure Detection, which is hereby incorporated by reference herein in its entirety. In some embodiments, the patient's heart may be paced to avoid decreases in heart rate caused by seizures associated with reduced heart rat Patient-specific seizure-detection algorithms may be developed in which seizure detection is based upon activity levels. For patients having increased heart rate associated with seizures, in whom, for example, the ability to discriminate ictal from non-ictal increases in heart rate is highest at moderate activity levels, and less reliable at low and high activity level, cardiac-based algorithms may be replaced by or complemented with algorithms that use other body signals such as movement, responsiveness/awareness, blood oxygen saturation, skin resistivity, respiration, etc. For patients having reduced heart rate during seizures, in whom, for example, the ability to discriminate ictal from nonictal decreases in heart rate is best at higher activity levels, other body signals may be used.

FIGS. 24C, 24D, and 24F provide examples of how a seizure detection index, such as heart rate, may be affected by work or activity levels of a patient, and demonstrate that activity levels may be used to dynamically adjust heart rate seizure detection thresholds to improve the accuracy of cardiac-based seizure detection algorithms. Other seizure detection indices may also be correlated to activity levels to provide improved seizure detection when cardiac-based algorithms are inapplicable or inaccurate.

Additional details as to how dynamic seizure detection thresholds may be determined for a first body data stream (such as a cardiac data stream) based on activity level or another second body data stream are provided in U.S. patent application Ser. No. 14/084,513, filed Nov. 19, 2013, to which the present application claims priority (See, e.g., FIGS. 24-26 and discussion thereof).

Figure 25:
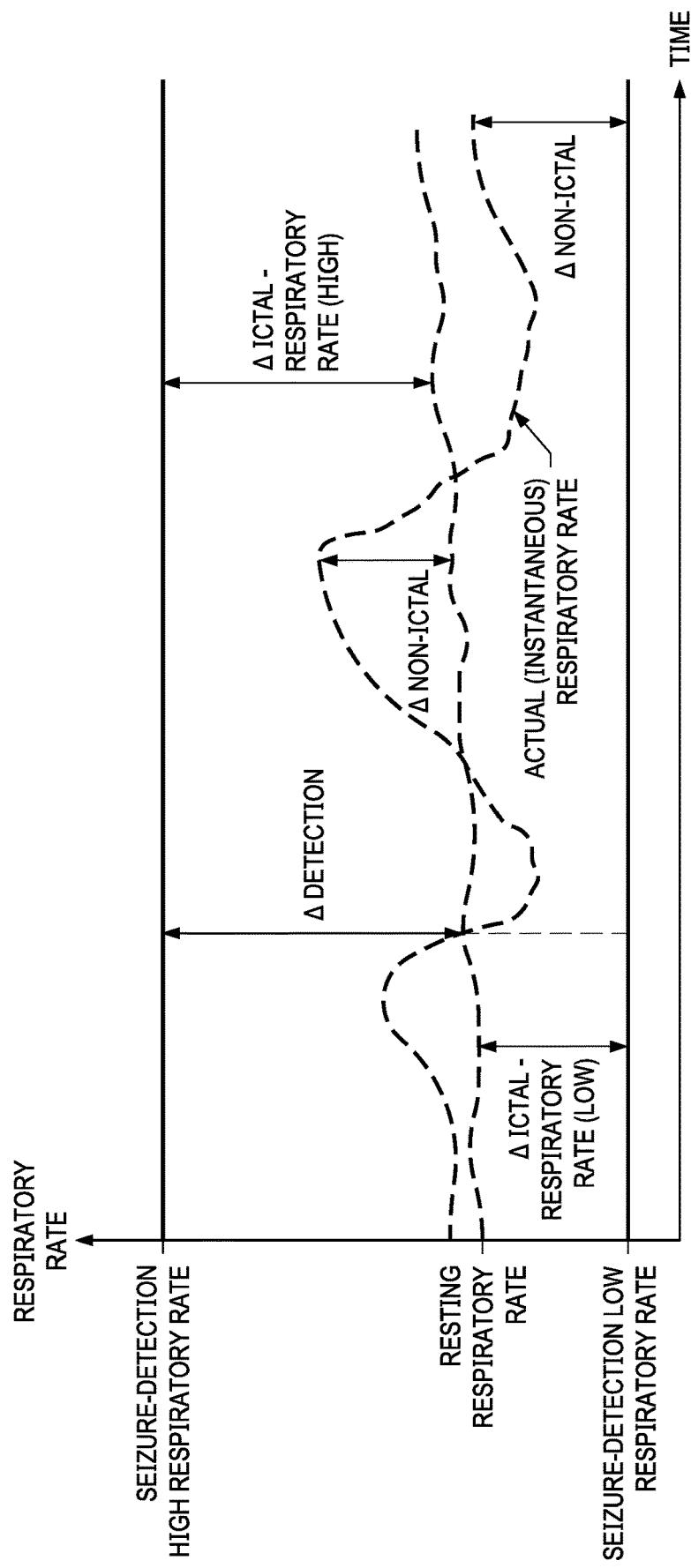
FIG. 25 shows an example of the ΔDetection, ΔNon-Ictal, and ΔIctal components of respiratory rates, according to some embodiments of the present disclosure.

FIG. 25 shows a simplified diagram of the dynamic nature of an exemplary reference respiratory rate, a current (actual or instantaneous) respiratory rate (CRR), ΔNon-Ictal, and ΔIctal components of increases in respiratory rate, and ΔDetection values, according to some embodiments of the present disclosure. The various relationships generally parallel those shown for heart rate in FIGS. 24A and 24B.

Figure 26:
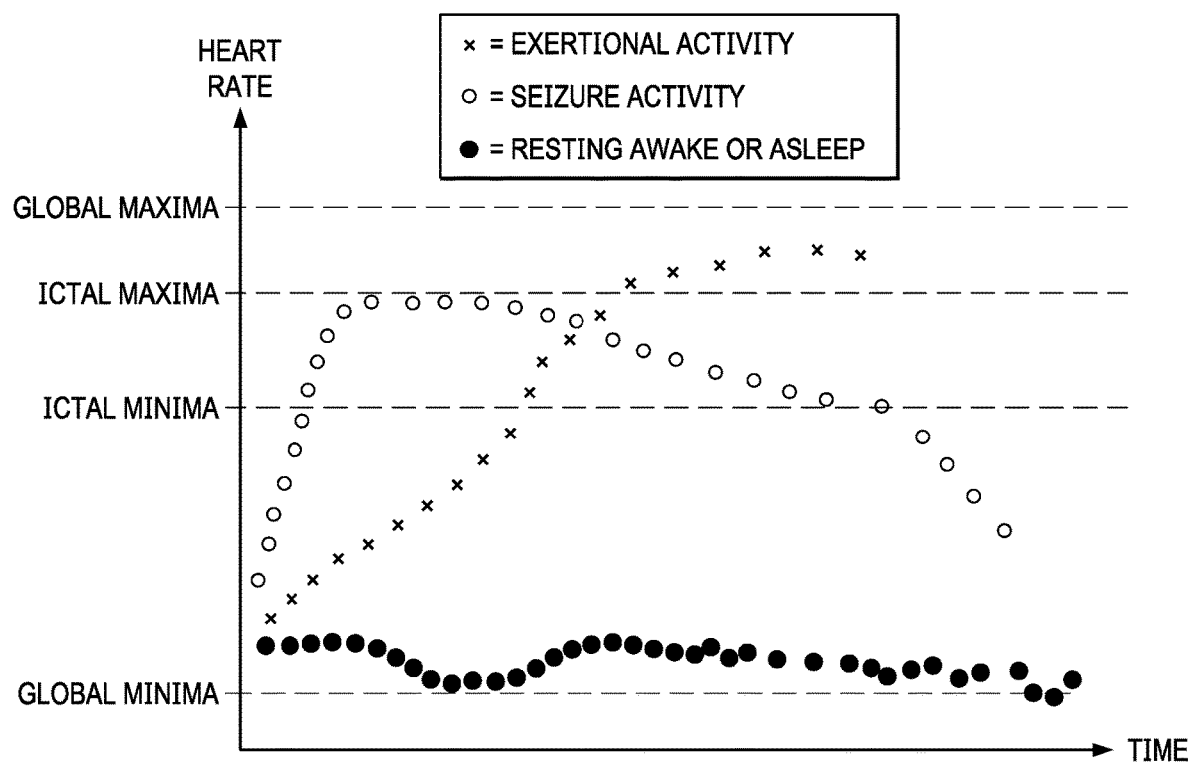
FIG. 26 shows an example of the ΔDetection, ΔNon-Ictal, and ΔIctal components of body data, according to some embodiments of the present disclosure.

FIG. 26 is an idealized representation of heart rate changes (y-axis) during sleep and resting wakefulness ●), exertional activity of various degrees of intensity (X) (x-axis) and seizures/ictal (+). Lines in dash ○) depict the lowest heart rate (global minima, such as that during certain sleep), the minimal increase in heart rate a seizure may cause (ictal minima), the maximal increase in heart rate a seizure may cause (ictal maxima) and the maximal heart rate (global maxima) given by the formula 220–age. The ictal maxima (for HR) may in convulsive seizures be equal to the global HR maxima. These curves serve as the basis for calculating increases in heart rate due to: a) exertional/physiological activity (ΔNon-Ictal); seizures (ΔIctal); and the magnitude of the detection margin (ΔDetection=ΔNon-Ictal−ΔIctal).

The minimal possible heart rate may or may not be the same as the resting heart rate and the maximal possible heart rate may or may not be the same as the maximal ictal heart rate. The resting, ictal and exertional heart rates may vary as a function of multiple factors, making the ΔDet variable in magnitude. In general, the lower the non-ictal heart (non-ictal heart rate encompasses resting and exertional heart rates) and the higher the ictal component, the larger the ΔDet. A probability index for ictal detections may be estimated based on the values of the non-ictal components of a body signal and a correction or normalization may be introduced to decrease the number of FN detections when the non-ictal component is high or the ΔIctal is low.

Although FIGS. 24A-26 are directed to heart rate or respiratory rate, other signal features, such as heart rate variability, blood pressure, respiratory rhythm, or other body signals such dermal activity, or oxygen saturation, catecholamine concentrations, brain signals (electrical, chemical, thermal, etc.) among others would also be expected to have ictal and non-ictal components of their changes, which may be identified and used to compute a delta detection.

Turning now to FIG. 27A, a stylized depiction of a heart rate change in conjunction with a kinetic index, in accordance with some embodiments herein, is shown. Those skilled in the art would appreciate that the heart rate and the kinetic index values shown in FIG. 27A are illustrated in an idealized fashion, and values of the both axes may vary and remain within the scope of the present embodiments.

FIG. 27A illustrates that initially, a patient's heart rate is relatively stable until the time 2711, where the heart rate begins to rise to a second level. The medical device 2300 may detect a change in the HR, wherein this detection may trigger an acquisition of another set of body data, such as a kinetic index. The medical device 2300 may then perform a correlation function to determine whether the changes in the HR correlate with the changes in the kinetic index. In the example of FIG. 27A, at the time 2711, at approximately the time of the change in the HR, an increase in the kinetic index is also observed. Based upon an analysis of the HR change and the increase in the kinetic index, the medical device 2300 may determine that there is a correlation between the changes in these two parameters. In one embodiment, the strength of this correlation may be qualitative (e.g., low, medium, high) or quantitative (e.g., −0.8, −0.2, 0.3, 0.9). In the example of FIG. 27A, at time 2711, which corresponds to the time marker labeled "1st change," the medical device 2300 may determine that the change in the HR has a satisfactory correlation (e.g., is commensurate) with the corresponding change in the kinetic index. That is, the medical device 2300 may determine that the change in HR is physiological in nature and has substantially no ictal component.

At the time 2712, the rise in the HR levels off, as indicated in FIG. 27A. Upon detection of a change (e.g., an increase, a decrease, or a leveling off) in HR, the medical device 2300 may acquire other body data to determine if the change is physiological and/or pathological. At the time 2712, when the HR levels off (which corresponds to another change in the signal), the medical device 2300 may acquire kinetic index data, which in this example, also levels off, indicating that the change in HR is physiological. The rise in the HR from the time period prior to the time 2711, to the HR at the time 2712 is the Δnon-ictal value for HR at that time (i.e., the change in the HR value is of a primarily a non-ictal component, caused by non-pathological causes).

At time 2713, the HR again rises, as shown in FIG. 27A. Upon the detection of the change in HR at time 2713, the medical device 2300 may check the behavior of the kinetic index. In the example of FIG. 27A, the kinetic index does not change at time 2713. At time 2713, the medical device 2300 may determine that the rise in HR is not associated with a corresponding increase in the kinetic index. Accordingly, the medical device 2300 may determine that change in the rise of HR at time 2713 is pathological. Therefore, the rise in the HR during time period 2713, from the HR during the time 2712 is the ΔictalMax value for HR (i.e., the change in the HR value is of a primarily an ictal component, and as such, is pathological in a patient with epilepsy).

Turning now to FIG. 27B, a stylized depiction of a heart rate change in conjunction with a kinetic index during a seizure with prominent motor activity, in accordance with another embodiment herein, is shown. In the example of FIG. 27B, the HR and a corresponding kinetic index value remain stable during time 2714. During time period 2714, the HR increases, however, this increase is commensurate with the change in the kinetic index. Therefore, the rise in HR at time 2714 is primarily non-pathological (Δnon-ictal).

At the beginning of time period 2715, the HR rises with no corresponding change in the kinetic index. In this case, the medical device 2300 may determine that this change in HR is pathological (Δictal in a patient with epilepsy). In this case, since a pathological rise in HR is detected with no contribution from kinetic activity of the patient, the medical device 2300 may determine that the rise in HR (during time period 2715) is primarily neurogenic (Δictal[neurogenic]).

At the beginning of time period 2716, the HR further increases, albeit with a corresponding change in the kinetic index. In this case, the further increase in HR is associated with an increase in kinetic activity, and the further increase in HR may be construed as having an exertional component (if the demand for oxygen is met) and a respiratory/metabolic component (if the demand for oxygen is not met, such as is the case in a convulsion) (Δictalexertional/metabolic). In this example, Δictal total is the sum of both Δictalneurogenic and Δictalexertional/metabolic. That is, when the patient has a seizure, the increase in HR may be primarily based upon neurogenic factors, and after a certain time period, contributions from exertion and respiratory/metabolic changes caused by the ictal state may contribute to a further rise in the HR (if the seizure spreads). In an alternative embodiment, upon detection of a change in a body signal (e.g., HR) that may be suggestive of a seizure, the medical device 2300 may acquire one or more other body signals (e.g., kinetic, respiratory/metabolic, or other signals) in order to determine the various contributions to Δictal and/or to confirm that a detection is accurate. Those skilled in the art having benefit of the present disclosure would appreciate that other body data indexes may be applied to the analysis relating to FIGS. 27A-27C.

Turning now to FIG. 27C, a stylized depiction of a heart rate change in conjunction with a kinetic index for illustrating a Δdetection, in accordance with embodiments herein, is provided. FIG. 27C illustrates a resting HR 2725 and a detection threshold HR 2723. In some embodiments, the detection threshold HR 2723 may be programmable, may be adjustable, or both. In this example, if the HR value rises above the detection threshold HR 2723, an ictal state may be declared by the medical device 2300. The difference between the detection threshold HR and the resting HR is Δdetection[T] (delta detection threshold). Therefore, once a HR increase crosses the detection threshold 2723, the medical device 2300 may issue a detection of a pathological state. Upon this issuance, a responsive action may be taken, such as those described elsewhere herein. The maximum available Δdetection[T] may be used to define the threshold [T] for issuing a detection when a change in HR is incommensurate with the kinetic index. If the increase in HR resulting in crossing of the detection threshold is non-ictal, e.g., the change in HR is commensurate with the kinetic index, a detection may not be issued. However, in certain situations, if the HR exceeds a maximum detection threshold, a detection may be issued regardless of any non-ictal component of HR.

In the example of FIG. 27C, the HR and a corresponding kinetic index value remain stable up to time 2717. At time 2717, the HR increases, wherein this increase is commensurate with a corresponding change in the kinetic index, as shown in FIG. 27C. The rise in HR due to the kinetic activity corresponding to time 2717 peaks at time 2718 and is deemed to be non-pathological (Δnon-ictal).

At time 2719, the HR increases substantially, and ultimately rises above the detection threshold HR. Moreover, the rise in HR at time 2719 fails to coincide with a rise in the kinetic index. As such, the medical device 2300 may determine that this rise in HR (at time 2719) is due to a pathological condition. The rise in HR continues to a maximum HR value at time 2721, after which the HR decreases. The rise in HR from the baseline value to the peak value at time marker 2721 is Δictal[max]. In some embodiments, where the detection threshold is set relative to Δictal[max] may vary based on the clinical application, wherein in some clinical applications the detection threshold may be set at a higher level than in other clinical applications. For example, if rapid detection or high sensitivity is more desirable, the detection threshold may be set at a lower level, than in cases where accuracy of detection is more desirable.

In the example of FIG. 27C, the patient's HR remains relatively stable until time 2722, where a rise in kinetic index appears immediately prior to this time. At time 2722, the HR rise is commensurate with the rise in the kinetic index (Δnon-ictal). In this example, the HR continues to rise incommensurately (Δictal) with the kinetic index, which indicates a pathological state. The difference between this maximum HR value and the Δnon-ictal value is Δictal[max]. In other words, when during this time period, the HR crosses the detection threshold and comprises an ictal component, the system may declare a seizure.

Moreover, after a decline in the kinetic index in time period 2722, the HR decreases below the resting HR. In some examples, at least a portion of this decline may be due to a non-pathological cause, and another portion may be the result of a pathological event. In some embodiments, the medical device 2300 may determine a −Δnon-ictal and a −Δictal. The analysis described above with respect to crossing the detection threshold above the resting HR may be applied to crossing a second detection threshold below the resting HR (not shown). Other body data indexes (e.g., respiratory index, endocrine index, neurologic index, etc.) may also be used in analyses similar to those exemplified in FIGS. 27A-27C.

Figure 27D:
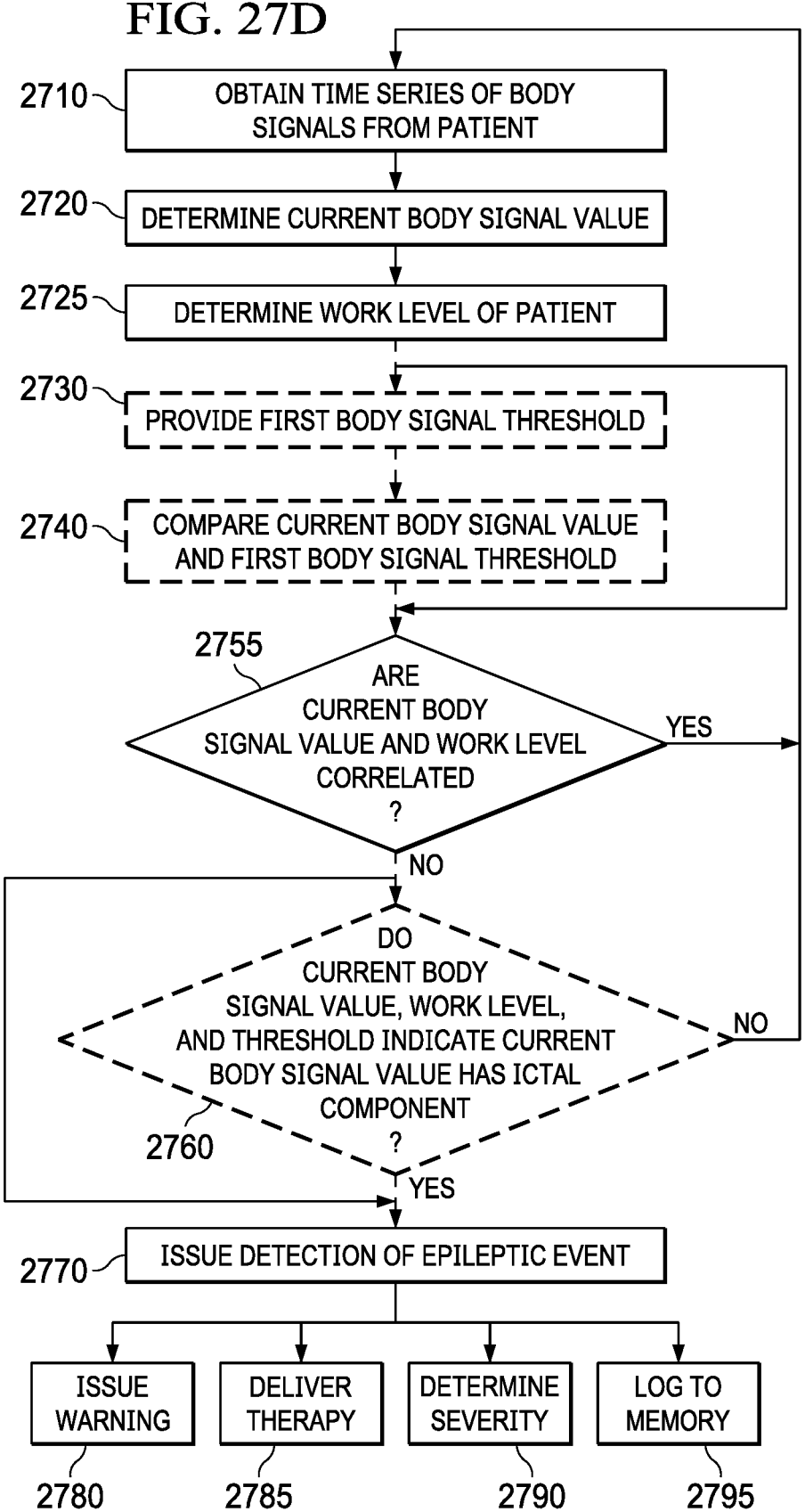
FIG. 27D shows a flowchart depiction of a method, according to some embodiments of the present disclosure.

FIG. 27D shows a flowchart representation of a method 2700, according to some embodiments of the present disclosure. A time series of body data from a patient may be obtained (block 2710). The time series of body data may comprise one or more body data streams suitable for detection of seizures, such as a cardiac signal, a respiratory signal, a blood oxygen saturation signal, etc. A current body signal value may be determined (block 2720) from said time series. The current body data value may comprise one or more of a current heart rate, a current respiratory rate, a current blood oxygen saturation, etc. A work level of the patient may be determined (block 2725). The work level determination may take into account at least in part one or more of a time of day, an indicator of said patient's overall health, an indicator of said patient's overall fitness, an indicator of said patient's level of consciousness (e.g., wakefulness v. sleep), the ambient temperature, the ambient humidity, or other patient or environmental conditions.

In some embodiments, upon the determination of work level (block 2725), the method may proceed to a determination (block 2755) whether the current body signal value and the work level are commensurate. (This determination will be described in more detail below). Optionally, upon the determination of work level (block 2725), the method may comprise providing at least a first body signal threshold (generally, a pathological threshold, e.g., an ictal threshold) (block 2730). In one embodiment, the first body signal threshold may be set based on the current body signal value. The current body signal value may be compared (block 2740) with the first body signal threshold. For example, the comparison (block 2740) may comprise a determination that the current body data value exceeds an ictal threshold.

Regardless of whether the optional embodiments at blocks 2730 and 2740 are performed, the method 2700 may comprise a determination whether the current body signal value and the work level are commensurate (block 2755). If they are commensurate, then it can reasonably be concluded that the patient is not currently undergoing a pathological state, e.g., an epileptic event, e.g., a seizure. Upon a finding of commensurateness (block 2755), the method 2700 may return to obtaining the time series of body signals (block 2710).

On the other hand, a finding of a lack of commensurateness (block 2755) may, but does not necessarily, indicate the patient is currently suffering a pathological state, e.g., an epileptic event, e.g., a seizure. Thus, optionally, a determination may be made (block 2760) as to whether the current body signal value comprises an ictal component. In one embodiment, the current body signal value may be considered to have an ictal component if its value is in a range that, based on the current work level and a threshold provided at block 2730, indicates an ictal component. At minimum, the current body signal only has an ictal component if its value is incommensurate with work level. In one embodiment, the current body signal value has an ictal component if it exceeds an ictal threshold for the body signal value for a given activity or work level. In an alternative embodiment, the current body signal value has an ictal component if it exceeds one of the exertional component or a ΔNon-Ictal value of the body signal value. For resting states (sleep or awake) the non-exertional component to certain body signals such as heart or respiratory rate is negligible. For other body signals such as neuronal electrical signals, the exertional component is negligible. The determination (block 2760) as to whether the current body signal value comprises an ictal component may be based on the work level (determined block 2725) and the comparing (block 2740). In one embodiment, ictal and non-ictal components and ΔDetection values may be calculated and used to estimate the accuracy of a detection. Based on the probability of detection accuracy, corrections or normalizations may be performed that may result in the issuance or non-issuance of a seizure detection.

If the determination (block 2760) is that the current body signal value comprises the ictal component, then a detection of an epileptic event, (e.g., a seizure) may be issued (block 2770), subject in at least one embodiment to the ictal component having a certain magnitude for a certain time period. Thereafter, at least one further action may be taken, such as issuing (block 2780) a warning of the epileptic seizure to the patient, a caregiver, or a physician; delivering (block 2785) a therapy, such as a vagus nerve electrical stimulation therapy using an implantable neurostimulator commercially available from Cyberonics, Inc., among other therapy modalities known to the skilled artisan; quantifying (block 2790) a severity of the epileptic seizure; and logging to memory (block 2795) one or more of the date and time of occurrence of the epileptic seizure, the severity of the epileptic seizure, a type of therapy delivered, or at least one effect of the therapy. Thereafter, flow may return (not shown) to obtaining (block 2710).

If the determination (block 2760) is that the current body signal value lacks the ictal component, then flow may return to obtaining (block 2710).

Therefore, in one embodiment, method 2700 may comprise seizure detection based on a correlation (or lack thereof) between the current body signal value (which may be considered a dependent variable) and work level (which may be considered an independent variable).

FIG. 28A shows a flowchart representation of providing a body signal threshold (block 2730) according to some embodiments. At least one time series of body data may be received (block 2810). Signals usable in embodiments of the present invention may include a cardiac signal, a respiratory signal, etc., which may be tested for the presence of an ictal component in (and thus for decorrelation or incommensurateness with) a work or activity level. In some embodiments, previously received and/or processed reference body data, such as that previously collected from the patient over a period of days, months or years, may also be looked up in a table (block 2820). In some embodiments, the table look up (block 2820) may comprise correlating the time series of body data with looked-up reference body data from block 2820. For example, it may be found that a current time series of body data received (block 2810) is poorly correlated with the looked-up reference body data (block 2820), thus suggesting that the patient's condition may have changed or the detection apparatus may be malfunctioning. (The reference data may be at least in part a function of the activity level and/or other factors). In some embodiments, the table look up (block 2820) may be based at least in part on the patient's work level (determined at FIG. 27, block 2725).

A reference body signal value may be determined (block 2840). In some embodiments, the reference body signal value may comprise an ictal threshold function, or an ictal value for a body data signal value. The first body signal reference value may be determined from one or more of the at least one time series of body data received (block 2810), or the looked-up reference body day from block 2820.

Turning now to FIG. 28B, a stylized depiction of a table for providing a reference value for the dependent variable (e.g., HR), that should correspond to a certain work or activity level (the independent variable) as indicated in FIG. 28A, in accordance with some embodiments, is illustrated. In one embodiment, upon determining the work level of the patient, the medical device 2300 may perform a look up of body data values in a table (e.g., such as the table of FIG. 28B) in order to provide a physiological reference value (e.g., mean, median, range (max.-min)) for the algorithm described in FIG. 27D. The table exemplified in FIG. 28B comprises work level values that each correspond with activity types. For each work level and activity type, the table may provide reference body data values obtained from a given patient or from a group of patients under physiological conditions. The endosomatic (e.g., level of consciousness, etc.) and exosomatic (e.g., ambient temperature) conditions under which the body data values were obtained may be documented in the look-up table to allow valid comparisons. These body data values may be used by the algorithm exemplified in FIG. 27D to perform comparisons. Those skilled in the art having benefit of the present disclosure would appreciate that additional work levels, activity types, and body data values may be provided in the table of FIG. 28B.

In the example of FIG. 28B, the work level (work level 1, 2, 3, etc.) may be used to select an activity type (activity type A, B, C, etc.) that corresponds to the work level. In one embodiment, the medical device 2300 may make a determination of the type of activity that the patient is engaged in based upon the detected work level. For example, for a particular patient, as shown in FIG. 28B, "work level-3" may correspond to "activity type-C" (walking). In an alternative embodiment, based upon sensed body signal(s), the medical device 2300 may determine the type of activity (e.g., REM sleep, walking, running, etc.) in which the patient is engaging. In one embodiment, this may be used as a verification function in order to determine that the work level corresponds to the activity type. In some embodiments, determination of the activity level may allow determination of the work level.

The medical device 2300 may look up the value of a particular body data (1st body data value, 2nd body data value, etc.) for the determined work level and the corresponding activity level. For example, if the medical device 2300 determines that the value of the work level is substantially equal to "work level-3," the medical device 2300 may make an assumption that the patient is walking ("activity type-C"). In some embodiments, the medical device 2300 may verify the activity type. This verification may be based upon detected body signal(s) and/or input received from an external source, e.g., an observer or caregiver. The corresponding reference body data value ("1st body data value") in this example is a heart rate of 82 beats per minute (BPM). This heart rate value may be used as a reference value to determine whether the current body signal is commensurate with the patient's activity or work level.

As another example, if the detected work level has a value of "work level-2," the medical device 2300 may make an assumption that the patient is in a non-REM sleep state ("activity type-B"). In some embodiments, the medical device 2300 may verify the activity type. The reference 3rd body data value corresponding to this example is a respiratory rate (RR) of 8 breaths per minute (BrPM). This respiratory rate value may be used as a reference or threshold value to determine whether the work level is commensurate with patient activity. Similarly, a plurality of body data values may be used as a threshold value to determine whether the detected work level is commensurate with patient activity. In some embodiments, the table may contain data about mental (e.g., cognitive, emotional) activity so that determination of an ictal content (if any) in the current body signal (e.g., the dependent variable) value may be accurately made.

Those skilled in the art having benefit of the present disclosure would appreciate that other types of look-up tables may be used to determine reference or threshold body data values and remain within the spirit and scope of the embodiments disclosed herein.

The methods depicted in FIGS. 27D-28A and described above may be governed by instructions that are stored in a non-transitory computer readable storage medium and that are executed by, e.g., a processor 2317 of the medical device 2300. Each of the operations shown in FIGS. 27D-28A may correspond to instructions stored in a non-transitory computer memory or computer readable storage medium. In various embodiments, the non-transitory computer readable storage medium includes a magnetic or optical disk storage device, solid state storage devices such as flash memory, or other non-volatile memory device or devices. The computer readable instructions stored on the non-transitory computer readable storage medium may be in source code, assembly language code, object code, or other instruction format that is interpreted and/or executable by one or more processors.

In other embodiments (not shown), the present disclosure relates to a method for detecting an epileptic seizure based upon a comparison between at least two time series of body signals from a patient, comprising: obtaining a first body signal time series from said patient; determining a current body signal value from said first body time series; obtaining a second body signal time series from said patient; determining a current body signal value from said second body time series; comparing said current first body signal value and said at least a second body signal value; determining based on said comparing whether or not the change between first and said first body signal is commensurate or is correlated; determining whether said current body signal value comprises an ictal component, based on a determination that said change in said first body signal value is incommensurate or uncorrelated with said value in said second body signal; issuing a detection of an epileptic seizure in response to said determination that said current body signal value comprises an ictal component; and taking at least one responsive action to said issuing, wherein said responsive action is selected from issuing a warning of said detection, delivering a therapy, determining a severity of the detected epileptic seizure, and logging to memory one or more of the date and time of occurrence of the detection of the epileptic seizure, a severity of the detected epileptic seizure, a type of therapy delivered to treat the epileptic seizure, or at least one effect of a therapy delivered to treat the epileptic seizure. In one embodiment, the strength and direction of the correlation between said at least first body signal time series and said at least second body signal time series may be determined. By way of example, the strength of the correlation may be determined to be low, medium or high or quantified and expressed as value [0-1] and the direction may be positive or negative. For a first body signal (e.g., heart rate) whose values move in the same direction as those of the second body signal (e.g., kinetic activity), that is when one increase the other also increase, and a decrease in one is accompanied by a decrease in the other, the correlation is positive and for those for which one value decreases while the other increases (e.g., vagus nerve activity and heart rate)

the correlation is negative. The absolute magnitude of the value of a correlation may be used to determine if there is an ictal component (see [004]) or a change in their pattern may be sufficient to make this determination. In one embodiment, the at least first and at least second body signals are different.

In some embodiments, this disclosure provides a method for identifying and using natural or innate body signal thresholds for identifying transitions between a non-pathological and pathological and the transition back to normalcy by determining using at least two body signals, the contribution to changes in said signal value of physiologic or non-pathologic factors versus those of non-physiologic or pathologic factors. In a patient with epilepsy in which heart rate increases due to non-pathologic factors such as jogging and also to seizures, parsing out the contributions from each physiologic and each pathologic factor contributing to changes in body signals values, allows for accurate determination of the transition from one state to the other. Coming back to epileptic seizures, classification of changes in a body signal (e.g., HR) into non-ictal (i.e., caused by exercise) and into ictal (caused by a seizure) and their quantification (for example, in beats/min for HR) leads to the identification of non-ictal body signal thresholds that among other factors, depend on level and type of physical activity. Let us say that the HR of a patient with epilepsy walking at speed $v_1$ on a level surface increases by an average of 20 bpm compared to when the patient is standing still. The +20 bpm may be used in this case as the seizure detection threshold each time the patient walks at speed $v_1$ on a level surface, all other things equal. In this patient a seizure detection may then be issued if and when the HR exceeds the ΔNon-ictal (+20 bpm) by an integer (e.g., 25 bpm−20 bpm=5) or non-integer value n, an increase over the reference value (+20 bpm) in this case that is referred herein to as ΔIctal.

In some embodiments, the present disclosure relates to one or more of the following numbered numbers: 51. A non-transitory computer readable program storage unit encoded with instructions that, when executed by a computer, perform a method for detecting an epileptic seizure based upon a time series of a patient's body data, comprising: determining a reference body data value; determining a short-term body data value; determining at least one body data delta value, based on at least a difference between said reference body data value and said short-term body data value; and detecting said epileptic seizure, based on said at least one body data delta value. 52. The non-transitory computer readable program storage unit of number 51, wherein determining said reference body data value comprises: receiving a reference time series of said body data; looking up a prior reference body data in a table; comparing said reference time series and said prior reference body data; and setting said reference body data value, based on said comparing. 53. The non-transitory computer readable program storage unit of number 51, wherein said short-term body data value is determined based upon a foreground time series of body data. 54. The non-transitory computer readable program storage unit of number 51, said method further comprising: determining an occurrence of an epileptic seizure, in response to said short-term body data value exceeding a seizure detection threshold; performing at least one further action selected from treating the seizure, issuing a warning regarding the seizure, or logging the seizure or the severity thereof, in response to said epileptic seizure being determined to have occurred; and providing said short-term body data value to a unit to said determining said at least one body data delta value, in response to said epileptic seizure being determined not to have occurred. 101. A non-transitory computer readable program storage unit encoded with instructions that, when executed by a computer, perform a method for detecting an epileptic seizure based upon a time series of beats of a patient's heart, comprising: obtaining said time series of heart beats; determining a reference heart rate value from said heart beats in a first time window; determining a second heart rate value from said heart beats in a second time window, wherein said second time window is shorter than said first time window; determining a third heart rate value from said heart beats in a third time window, wherein said third time window is shorter than said second time window; determining a non-ictal component of said patient's heart rate value, wherein said non-ictal component equals said second heart rate value minus said reference heart rate value; determining an ictal component of said patient's heart rate value, wherein said ictal component equals said third heart rate value minus said reference heart rate value; determining a seizure detection delta, wherein said seizure detection delta equals said ictal component minus said non-ictal component; and detecting said epileptic seizure, based at least in part on said seizure detection delta exceeding a seizure detection threshold. 102. The non-transitory computer readable program storage unit of number 101, wherein said first time window comprises from about 60 sec to about 24 hr. 103. The non-transitory computer readable program storage unit of number 101, wherein said second time window comprises from about 1 sec to about 60 sec. 104. The non-transitory computer readable program storage unit of number 101, wherein determining said non-ictal component comprises measuring a body signal relating to a work level of said patient, wherein said measuring is performed by one or more of an accelerometer, an inclinometer, an electromyography (EMG) sensor, a muscle temperature sensor, an oxygen consumption sensor, a lactic acid accumulation sensor, a sweat sensor, a neurogram sensor, a force transducer, or an ergometer. 105. The non-transitory computer readable program storage unit of number 101, wherein determining said non-ictal component is based at least in part on one or more of a time of day, an indicator of said patient's overall health, an indicator of said patient's overall fitness, or an indicator of said patient's wakefulness. 106. The non-transitory computer readable program storage unit of number 101, further comprising dynamically adjusting said seizure detection threshold based at least in part on one or more of a time of day, an indicator of said patient's overall health, an indicator of said patient's overall fitness, an indicator of said patient's wakefulness, a time since a most recent previous seizure, an average inter-seizure interval, a severity of a most recent previous seizure, or an average seizure severity. 201. A medical device system, comprising: at least one first sensor configured to collect data relating to a time series of beats of a patient's heart; at least one second sensor configured to collect data relating to said patient's work level; and a medical device, comprising: a current body signal module configured to obtain a time series of heart beats from said collected body data; to determine a reference body data value from said heart beats in a first time window; and to determine a short-term body data value from said heart beats in a second time window, wherein said second time window is shorter than said first time window; a ictal component module configured to determine a non-ictal component of said short-term body data value, based at least in part on said data relating to said work level; to determine an ictal component of said short-term body data value, wherein said ictal component equals said short-term body data value minus said reference body data value; and to determine a seizure detection delta, wherein said seizure detection delta equals said ictal component minus said non-ictal component; and a seizure detection module configured to detect an epileptic seizure, based at least in part on said seizure detection delta exceeding a seizure detection threshold. 202. The medical device system of number 201, wherein said at least one second sensor is selected from an accelerometer, an inclinometer, an electromyography (EMG) sensor, a muscle temperature sensor, an oxygen consumption sensor, a lactic acid accumulation sensor, a sweat sensor, a neurogram sensor, a force transducer, or an ergometer. 203. The medical device system of number 201, further comprising an additional factor module configured to determine at least one additional factor selected from a time of day, an indicator of said patient's overall health, an indicator of said patient's overall fitness, or an indicator of said patient's wakefulness; and wherein said ictal component module is configured to determine a non-ictal component of said short-term body data value, based at least in part on said at least one additional factor. 204. The medical device system of number 201, wherein said epileptic seizure detection module is configured to dynamically adjusted said seizure detection threshold based at least in part on one or more of a time of day, an indicator of said patient's overall health, an indicator of said patient's overall fitness, an indicator of said patient's wakefulness, a time since a most recent previous seizure, an average inter-seizure interval, a severity of a most recent previous seizure, or an average seizure severity. 205. A method for detecting an epileptic seizure based upon a time series of beats of a patient's heart, comprising: obtaining said time series of heart beats; determining a current heat rate from said time series of heart beats; providing a first reference heart rate value, providing a second reference heart rate value, determining at least one of a non-ictal component of said patient's heart rate value, wherein said non-ictal component equals said current heart rate value minus said second reference heart rate value; a delta detection component of said patient's heart rate value, wherein said delta detection component equals said first reference heart rate value minus said current heart rate value; and a delta ictal value, wherein said delta ictal value equals said first reference heart rate value minus said second reference heart rate value; and determining at least one of a risk of a false positive detection, a risk of a false negative detection, and the occurrence of an epileptic seizure, wherein said determining is based on at least one of said delta non-ictal value, said delta detection value, and said delta ictal value. 206. The method of number 205, wherein said first reference heart rate value is an ictal threshold of heart rate as a function of patient activity level. 207. The method of number 205, wherein said second reference heart rate value is a resting heart rate of the patient. 301. A method for detecting an epileptic seizure based upon a time series of body signals from a patient, comprising: determining a current body signal value from a time series of body data from said patient; determining a work level of said patient; and determining whether said current body signal value comprises an ictal component, based on said work level; issuing a detection of an epileptic seizure in response to said determination that said current body signal value comprises an ictal component; and taking at least one action selected from issuing a warning of said detection, delivering a therapy, determining a severity of the detected epileptic seizure, and logging to memory one or more of the date and time of occurrence of the epileptic seizure, a severity of the epileptic seizure, a type of therapy delivered to treat the epileptic seizure, or at least one effect of a therapy delivered to treat the epileptic seizure. 302. A method for detecting an epileptic seizure based upon a time series of body signals from a patient, comprising: receiving a time series of a first body signal from the patient; receiving a time series of a second body signal from the patient; determining if there is a change in said time series of said first body signal; determining if there is a change in said time series of a second body signal that correlates to a change in said time series of a first body signal, in response to determining that there is a change in said time series of a first body signal, detecting an epileptic seizure in response to determining that there is no change in said time series of a second body signal that correlates to a change in said time series of a first body signal; performing a responsive action in response to detecting an epileptic seizure, wherein said responsive action comprises at least one of delivering a therapy, providing a warning, and logging data relating to said epileptic seizure. 303. The method of number 302, wherein performing a responsive action is selected from delivering a therapy comprising at least one of an electrical therapy to a target nerve structure and a drug therapy; providing a warning comprises a warning to the patient or a caregiver, wherein the warning is at least one of an auditory warning, a visual warning, a tactile warning, an email, a text message, and telephone call; and logging at least one of the date and time of occurrence of the epileptic seizure, a severity of the epileptic seizure, a type of therapy delivered to treat the epileptic seizure, or at least one effect of a therapy delivered to treat the epileptic seizure. 304. The method of number 303, further comprising determining an ictal component of said change in said first body signal in response to detecting an epileptic seizure, wherein said ictal component is based upon a different between a value of said first body signal prior to detecting an epileptic event and a value of said first body signal after detecting said epileptic event. 305. The method of number 304, wherein said ictal component comprises the difference between the value of said first body signal prior to determining that there is no change in said time series of a second body signal that correlates to a change in said time series of a first body signal, and a value of said first body signal after determining that there is no change in said time series of a second body signal that correlates to a change in said time series of a first body signal. 306. The method of number 302, further comprising determining a first body index time series from said time series of said first body signal, determining a second body index time series from said time series of said second body signal; wherein determining if there is a change in said time series of said first body signal comprises determining if there is a change in said first body index time series; and wherein determining if there is a change in said time series of a second body signal that correlates to a change in said time series of a first body signal comprises determining whether there is a change in said second body index time series that correlates to a change in said first body index time series. 401. A method for detecting an epileptic seizure based upon a comparison between at least two time series of body signals from a patient, comprising: obtaining a first body signal time series from said patient; determining a current body signal value from said first body time series; obtaining a second body signal time series from said patient; determining a current body signal value from said second body time series; comparing said current first body signal value and said at least a second body signal value; determining based on said comparing whether or not the change between first and said first body signal is commensurate or is correlated; determining whether said current body signal value comprises an ictal component, based on a determination that said change in said first body signal value is incommensurate or uncorrelated with said value in said second body signal; issuing a detection of an epileptic seizure in response to said determination that said current body signal value comprises an ictal component; and taking at least one responsive action to said issuing, wherein said responsive action is selected from issuing a warning of said detection, delivering a therapy, determining a severity of the detected epileptic seizure, and logging to memory one or more of the date and time of occurrence of the detection of the epileptic seizure, a severity of the detected epileptic seizure, a type of therapy delivered to treat the epileptic seizure, or at least one effect of a therapy delivered to treat the epileptic seizure. 402. The method of number 401, further comprising determining the strength and direction of the correlation between said at least first body signal time series and said at least second body signal. 403. The method of number 402, further comprising determining a presence of an ictal component based at least in part on the absolute magnitude of the change in the value of the correlation. 404. The method of number 402, further comprising determining a presence of an ictal component based at least in part on a change in a pattern of the correlation. 405. The method of number 401, wherein the at least first and at least second body signals are different. 501. A method for identifying and using natural or innate body signal thresholds for identifying a transition from a non-pathological to a pathological state or a transition from a pathological to a non-pathological state, comprising: determining at least two body signals, and determining a first contribution to changes in the value of each said body signal from physiologic or non-pathologic factors and a second contribution from non-physiologic or pathologic factors.

In some embodiments, the present disclosure relates to a method for detecting an epileptic seizure based upon a time series of a patient's body data, comprising: determining a reference body data value; determining a present body data value; determining at least one body data delta value, based on at least a difference between said reference body data value and said body data value; and detecting said epileptic seizure, based on said at least one body data delta value.

In other embodiments, the present disclosure relates to a method for detecting an epileptic seizure based upon a time series of beats of a patient's heart, comprising: obtaining said time series of heart beats; determining a first, reference heart rate value from said heart beats in a first, long-term time window; determining a second heart rate value from a measure of central tendency of heart beats in a second, second, time window, wherein said second time window is shorter than said first time window; determining a third heart rate value from a measure of central tendency of said heart beats in a third, short-term, time window, wherein said third time window is shorter than said second time window; determining a non-ictal component of said patient's heart rate value, wherein said non-ictal component equals said second heart rate value minus said reference heart rate value; determining an ictal component of said patient's heart rate value, wherein said ictal component equals said third heart rate value minus said reference heart rate value; determining a seizure detection delta, wherein said seizure detection delta equals said ictal component minus said non-ictal component; and detecting said epileptic seizure, based at least in part on said seizure detection delta exceeding a certain value and/or a seizure detection threshold.

What is claimed:

1. A method for detecting an epileptic event in a patient's body via one or more medical devices, comprising:
    receiving a first body signal during a first time period;
    receiving a second body signal during the first time period;
    determining a work level;
    determining whether there is a change in at least one of a direction, a latency, a magnitude, a rate, and a duration of the first body signal during the first time period;
    determining a change in the work level;
    determining whether there is a change in at least one of the direction, the latency, the magnitude, the rate, and the duration of the second body signal during the first time period that, based on the change in the work level, is commensurate with the change in the first body signal, in response to determining that there is the change at least one of the direction, the latency, the magnitude, the rate, and the duration of in the first body signal during the first time period;
    detecting the epileptic event in response to determining that there is the change in the second body signal that based on the change in the work level is incommensurate with the change in the first body signal;
    performing a responsive action in response to detecting the epileptic event, the responsive action being delivering a therapy where the therapy includes:
    initiating a first electrical signal to the first cranial nerve structure of the patient using a first polarity configuration in which the first electrode functions as a cathode and the second electrode functions as an anode, the first electrical signal is configured to induce action potentials in the first cranial nerve structure, wherein a charge accumulates at the anode and the cathode as a result of the first electrical signal;
    switching from the first polarity configuration to a second polarity configuration upon termination of the first electrical signal where the first electrode functions as the anode and the second electrode functions as the cathode in the second polarity configuration; and
    providing a second electrical signal to the second cranial nerve structure in the second polarity configuration, the second electrical signal is configured to induce action potentials in the second cranial nerve structure where at least a portion of the second electrical signal comprises the accumulated charge from the first electrical signal.

2. The method of claim 1, wherein detecting the epileptic event comprises:
    determining a non-ictal component of the change in the first body signal based upon a contribution by a physiological or non-pathological activity in the patient's body that relates to the change in the second body signal; and
    determining an ictal component of the change in at least one of: the first body signal and the second body signal based upon a difference between an entirety of the change in the first body signal, and a non-ictal component.

3. The method of claim 1, further comprising determining an ictal component of the change in at least one of: the first body signal and the second body signal, in response to detecting the epileptic event, wherein the ictal component is based upon a difference between a value of the first body signal prior to the detecting the epileptic event and a value of the first body signal during the detecting the epileptic event.

4. The method of claim 1, wherein determining whether there is a change in the second body signal during the first time period that is commensurate with the change in the first body signal comprises
    determining a commensurate index between the first body signal and the second body signal, and
    comparing the commensurate index with at least a first commensurate threshold; and
    wherein determining that there is a change in the second body signal that is commensurate with the change in the first body signal comprises determining that the commensurate index is at or above the first commensurate threshold;
    wherein the commensurate determination is based on a value being reached.

5. The method of claim 1, wherein determining whether there is the change in the second body signal during the first time period that is commensurate with the change in the first body signal comprises determining an occurrence of a commensurate state between the first body signal and the second body signal;
    wherein the commnsurate state determination is based on a value being reached.

6. The method of claim 5, wherein determining the commensurate state between the first body signal and the second body signal is based on an emergence of an ictal component in the first body signal and the second body signal.

7. The method of claim 1, further comprising determining an ictal component of the first body signal in response to a determination that there is the change in the second body signal that is commensurate with the change in the first body signal, wherein the ictal component is based on a value of the first body signal prior to the determination that there is the change in the second body signal that is commensurate with the change in the first body signal.

8. The method of claim 1, further comprising determining there is an ictal component to the change in the first body signal in response to a determination that the change in the second body signal that is incommensurate with the change in a physiologic work level, wherein the ictal component is based on a difference between 1) a value of the first body signal after the determination that the change in the second body signal that is incommensurate with the change in the physiologic work level and 2) a value of the first body signal prior to the determination that there is no change in the second body signal.

9. The method of claim 1, further comprising determining a first body index from the first body signal and determining a second body index from the second body signal.

10. The method of claim 1, further comprising quantifying a commensurate level of the change in the first body signal and the change in the second body signal.

* * * * *